(12) United States Patent
Chen et al.

(10) Patent No.: US 8,629,243 B2
(45) Date of Patent: Jan. 14, 2014

(54) VARIANT SUCROSE TRANSPORTER POLYPEPTIDES THAT ENABLE FASTER SUCROSE UTILIZATION IN BACTERIA

(75) Inventors: Qi Chen, Wallingford, PA (US); Qiong Cheng, Wilmington, DE (US); Jian Ping Lai, Wallingford, PA (US); Kristin Ruebling-Jass, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 234 days.

(21) Appl. No.: 13/210,488

(22) Filed: Aug. 16, 2011

(65) Prior Publication Data

US 2013/0045518 A1 Feb. 21, 2013

(51) Int. Cl.
*C07K 14/245* (2006.01)

(52) U.S. Cl.
USPC .......................................... 530/350; 536/23.7

(58) Field of Classification Search
None
See application file for complete search history.

(56) References Cited

U.S. PATENT DOCUMENTS

| 6,960,455 B2 | 11/2005 | Livshits et al. |
| 2011/0136190 A1 | 6/2011 | Eliot et al. |

FOREIGN PATENT DOCUMENTS

| WO | 2009078687 | 6/2009 |
| WO | 2010051849 | 5/2010 |

OTHER PUBLICATIONS

Olson et al., "Production of tyrosine from sucrose or glucose achieved by rapid genetic changes to phenylalaine-producing *Escherichia coli* strains", Appl. Microbiol. Biotechnol. (2007) vol. 74, pp. 1031-1040.

Jahreis et al., "Adaptation of sucrose metabolism in the *Escherichia coli* wild-type strain EC3132", J. Bacteriol., Oct. 2002, pp. 5307-5316.

Lee et al., "Development of sucrose-utilizing *Escherichia coli* K-12 strain by cloning β-fructofuranosidases and its application for L-threonine production", Appl. Microbiol. Biotechnol. (2010) vol. 88, pp. 905-913.

U.S. Appl. No. 12/960,634, filed Dec. 6, 2010.
U.S. Appl. No. 12/960,646, filed Dec. 6, 2010.
U.S. Appl. No. 13/210,550, filed Aug. 16, 2011.

*Primary Examiner* — Rebecca Prouty

(57) ABSTRACT

Variant sucrose transporter polypeptides that enable faster sucrose utilization in bacteria are described. Additionally, variant or recombinant bacteria comprising these variant sucrose transporter polypeptides, and methods of utilizing the bacteria to produce products such as glycerol and glycerol-derived products are provided.

1 Claim, No Drawings

VARIANT SUCROSE TRANSPORTER POLYPEPTIDES THAT ENABLE FASTER SUCROSE UTILIZATION IN BACTERIA

FIELD OF THE INVENTION

The invention relates to the fields of microbiology and molecular biology. More specifically, variant sucrose transporter polypeptides that enable faster sucrose utilization in bacteria, variant or recombinant bacteria comprising these variant sucrose transporter polypeptides, and methods of utilizing such bacteria to produce products such as glycerol and glycerol-derived products are provided.

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of sucrose and mixed feedstocks containing sucrose and other sugars as carbohydrate sources for microbial production systems would be more commercially desirable because these materials are usually readily available at a lower cost.

A production microorganism can function more efficiently when it can utilize any sucrose present in a mixed feedstock. Therefore, when a production microorganism does not have the ability to utilize sucrose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars. Moreover, many bacteria lack the ability to utilize sucrose. For example, less than 50% of *Escherichia coli* (*E. coli*) strains have the ability to utilize sucrose. Thus, when a production microorganism cannot utilize sucrose as a carbohydrate source, it is desirable to engineer the microorganism so that it can utilize sucrose.

Recombinant bacteria that have been engineered to utilize sucrose by incorporation of sucrose utilization genes have been reported. For example, Livshits et al. (U.S. Pat. No. 6,960,455) describe the production of amino acids using *Escherichia coli* strains containing genes encoding a metabolic pathway for sucrose utilization. Additionally, Olson et al. (*Appl. Microbiol. Biotechnol.* 74:1031-1040, 2007) describe *Escherichia coli* strains carrying genes responsible for sucrose degradation, which produce L-tyrosine or L-phenylalanine using sucrose as a carbon source. Additionally, Eliot et al. (U.S. Patent Application Publication No. 2011/0136190) describe recombinant bacteria that are capable of producing glycerol and glycerol-derived products from sucrose. However, there is a need for bacterial strains that have an improved ability to utilize sucrose. Additionally, there is a need for bacterial strains having an improved capability of producing glycerol and glycerol-derived products using sucrose as carbon source.

SUMMARY OF THE INVENTION

One embodiment provides a variant sucrose transporter polypeptide having:
(a) an amino acid sequence that has at least 95% identity to an amino acid sequence as set forth in SEQ ID NO:24 based on a Clustal W method of alignment and having at least one amino acid change selected from the group consisting of:
  (i) leucine to proline at position 61;
  (ii) phenylalanine to leucine at position 159;
  (iii) glycine to cysteine at position 162;
  (iv) proline to histidine at position 169;
  (v) leucine to tryptophan at position 61;
  (vi) leucine to histidine at position 61;
  (vii) leucine to phenylalanine at position 61; and
  (viii) leucine to tyrosine at position 61; or
(b) an amino acid sequence that has at least 95% identity to an amino acid sequence as set forth in SEQ ID NO:44 based on a Clustal W method of alignment and having a length of 402 to 407 amino acids from the N-terminus; or
(c) an amino acid sequence that has at least 95% identity to an amino acid sequence as set forth in SEQ ID NO:44 based on a Clustal W method of alignment, having a length of 402 to 407 amino acids from the N-terminus, and having at least one of the amino acid changes of (a).

Another embodiment provides a bacterium comprising in its genome or on at least one recombinant construct:
(a) a nucleotide sequence encoding a variant sucrose transporter polypeptide, said polypeptide having:
  (i) an amino acid sequence that has at least 95% identity to an amino acid sequence as set forth in SEQ ID NO:24 based on a Clustal W method of alignment and having at least one amino acid change selected from the group consisting of:
    (A) leucine to proline at position 61;
    (B) phenylalanine to leucine at position 159;
    (C) glycine to cysteine at position 162;
    (D) proline to histidine at position 169;
    (E) leucine to tryptophan at position 61;
    (F) leucine to histidine at position 61;
    (G) leucine to phenylalanine at position 61; and
    (H) leucine to tyrosine at position 61; or
  (ii) an amino acid sequence that has at least 95% identity to an amino acid sequence as set forth in SEQ ID NO:44 based on a Clustal W method of alignment and having a length of 402 to 407 amino acids from the N-terminus; or
  (iii) an amino acid sequence that has at least 95% identity to an amino acid sequence as set forth in SEQ ID NO:44 based on a Clustal W method of alignment, having a length of 402 to 407 amino acids from the N-terminus, and having at least one of the amino acid changes of (i); and
(b) a nucleotide sequence encoding a polypeptide having sucrose hydrolase activity;
wherein (a) and (b) are each operably linked to the same or a different promoter, further wherein said bacterium metabolizes sucrose at a greater rate than a bacterium containing a wild-type sucrose transporter polypeptide having an amino acid sequence as set forth in SEQ ID NO:24.

Another embodiment provides a process for making glycerol, 1,3-propanediol and/or 3-hydroxypropionic acid from sucrose comprising:
a) culturing a recombinant bacterium that comprises a nucleotide sequence encoding a variant sucrose transporter polypeptide and produces 1,3-propanediol, glycerol, and/or 3-hydroxypropionic acid, as disclosed herein, in the presence of sucrose; and
b) recovering the glycerol, 1,3-propanediol and/or 3-hydroxypropionic acid produced.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5(a bis), and Section 208 and Annex C of the Administrative Instructions). The symbols and format used for nucleotide and amino acid sequence data comply with the rules set forth in 37 C.F.R. §1.822.

TABLE A

Summary of Gene and Protein SEQ ID Numbers

| Gene | Coding Sequence SEQ ID NO: | Encoded Protein SEQ ID NO: |
|---|---|---|
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| cscB from *Escherichia coli* ATCC ® 13281 | 23 | 24 |
| cscB variant L61P | 25 | 26 |
| cscB variant F159L | 27 | 28 |
| cscB variant G162C | 29 | 30 |
| cscB variant P169H | 31 | 32 |
| cscB variant L61W | 33 | 34 |
| cscB variant L61H | 35 | 36 |
| cscB variant L61F | 37 | 38 |
| cscB variant L61Y | 39 | 40 |
| cscB variant 403STOP | 41 | 42 |
| cscB variant 408STOP | 43 | 44 |
| cscA from *Escherichia coli* EC3132 | 46 | 47 |
| cscA from *Escherichia coli* ATCC13281 | 48 | 49 |
| bfrA from *Bifidobacterium lactis* strain DSM 10140$^T$ | 50 | 51 |
| SUC2 from *Saccharomyces cerevisiae* | 52 | 53 |
| scrB from *Corynebacterium glutamicum* | 54 | 55 |
| sucrose phosphorylase gene from *Leuconostoc mesenteroides* DSM 20193 | 56 | 57 |
| sucP *Bifidobacterium adolescentis* DSM 20083 | 58 | 59 |
| scrK from *Agrobacterium tumefaciens* | 60 | 61 |
| scrK from *Streptococcus mutans* | 62 | 63 |
| scrK From *Escherichia coli* | 64 | 65 |
| scrK from *Klebsiella pneumoniae* | 66 | 67 |
| cscK from *Escherichia coli* | 68 | 69 |
| cscK from *Enterococcus faecalis* | 70 | 71 |
| HXK1 from *Saccharomyces cerevisiae* | 72 | 73 |
| HXK2 from *Saccharomyces cerevisiae* | 74 | 75 |
| dhaT from *Klebsiella pneumoniae* | 76 | 77 |
| dhaX from *Klebsiella pneumoniae* | 78 | 79 |

SEQ ID NO:45 is the nucleotide sequence of the cscAKB gene cluster from *Escherichia coli* ATCC®13281.

SEQ ID NO:80 is the nucleotide sequence of plasmid pSYCO101.

SEQ ID NO:81 is the nucleotide sequence of plasmid pSYCO103.

SEQ ID NO:82 is the nucleotide sequence of plasmid pSYCO106.

SEQ ID NO:83 is the nucleotide sequence of plasmid pSYCO109.

SEQ ID NO:84 is the nucleotide sequence of plasmid pSYCO400/AGRO.

SEQ ID NOs:85-102 are the nucleotide sequences of primers used in the Examples herein.

SEQ ID NO:103 is the nucleotide sequence of plasmid pBHR-cscBKA.

SEQ ID NOs:104-113 are the amino acid sequences of CscB variants described in Comparative Examples 11-13, 15, 17-19, and 21-24.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "recombinant glycerol-producing bacterium" refers to a bacterium that has been genetically engineered to be capable of producing glycerol and/or glycerol-derived products.

The term "variant sucrose transporter polypeptide" refers to a polypeptide having sucrose transporter activity that has an amino acid sequence that differs from the sequence of a wild-type sucrose transporter polypeptide. The difference in the sequence of the variant sucrose transporter polypeptide may be any one of the following: (i) an amino acid substitution in at least one position of the wild-type sequence, (ii) the sequence of the variant sucrose transporter polypeptide may be shortened from that of the wild-type sequence, or (iii) the sequence of the variant sucrose transporter polypeptide may be shortened from that of the wild-type sequence and contain an amino acid substitution in at least one position of the wild-type sequence.

The term "polypeptide having sucrose transporter activity" refers to a polypeptide that is capable of mediating the transport of sucrose into microbial cells.

The term "polypeptide having fructokinase activity" refers to a polypeptide that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "Frk", "scrK", "cscK", "FK", and "KHK". Fructokinase is encoded by the scrK gene in *Agrobacterium tumefaciens* and *Streptococcus mutans*; and by the cscK gene in certain *Escherichia coli* strains.

The term "polypeptide having sucrose hydrolase activity" refers to a polypeptide that has the ability to catalyze the hydrolysis of sucrose to produce glucose and fructose. Such polypeptides are often referred to as "invertases" or "β-fructofuranosidases". Typical of these enzymes is EC 3.2.1.26. Examples of genes encoding polypeptides having sucrose hydrolase activity are the cscA gene found in *E. coli* strains EC3132 (Jahreis et al. supra) or ATCC®3281 (Olson et al., supra), the bfrA gene from *Bifidobacterium lactis* strain DSM 10140$^T$, and the SUC2 gene from *Saccharomyces cerevisiae* (Carlson and Botstein, *Cell* 28:145, 1982). A polypeptide having sucrose hydrolase activity may also have sucrose phosphate hydrolase activity. An example of such a peptide is encoded by scrB in *Corynebacterium glutamicum* (Engels et al., *FEMS Microbiol Lett.* 289:80-89, 2008). A polypeptide having sucrose hydrolase activity may also have sucrose phosphorylase activity. Typical of such an enzyme is EC 2.4.1.7. Examples of genes encoding sucrose phosphorylases having sucrose hydrolase activity are found in *Leuconostoc mesenteroides* DSM 20193 (Goedl et al., *Journal of Biotechnology* 129:77-86, 2007) and *Bifidobacterium adolescentis* DSM 20083 (van den Broek et al., *Appl. Microbiol. Biotechnol.* 65:219-227, 2004), among others.

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "β" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild-type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae, Citrobacter freundii*, and *Clostridium* pasteurianum. Each of these genes encode a polypeptide belonging to the family of type III alcohol dehydrogenases, which exhibits a conserved iron-binding motif, and has a preference for the NAD$^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+$NAD^+$ to 3-phospho-D-glyceroyl-phosphate+NADH+H. Typical of glyceraldehyde-3-phosphate dehydrogenase is EC 1.2.1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+$/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild-type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant bacteria disclosed herein and, particularly, carbon sources comprising sucrose. The carbon source may further comprise monosaccharides, other disaccharides, oligosaccharides; or polysaccharides.

The terms "host cell" and "host bacterium" are used interchangeably herein and refer to a bacterium capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The terms "native nucleotide sequence" and "wild-type nucleotide sequence" are used interchangeably herein to refer to a nucleotide sequence that is normally found in the host microorganism.

The term "non-native nucleotide sequence" refers to a nucleotide sequence that is not normally found in the host microorganism.

The terms "native polypeptide" and "wild-type polypeptide" are used interchangeably herein to refer to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., Anal. Biochem. 138:267-284 (1984): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS. 5:151-153 (1989); Higgins, D. G. et al., Comput. Appl. Biosci. 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., J. Mol. Biol., 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a bacterial cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The term "variant bacterium" refers to a wild-type bacterium that has undergone a spontaneous mutation, natural transformation, natural transduction, or natural transposition; or has been modified by mutagenesis.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are variant sucrose transporter polypeptides that enable faster sucrose utilization in bacteria. Sucrose transporter polypeptides are polypeptides that are capable of mediating the transport of sucrose into microbial cells. Various sucrose transporter polypeptides are known in the art. The sucrose transporter polypeptides disclosed herein are variants of the wild-type sucrose transporter polypeptide CscB from *E. coli* ATCC®3281 (set forth in SEQ ID NO:24, nucleotide coding sequence set forth in SEQ ID NO:23). These variant sucrose transporter polypeptides were isolated from variant *E. coli* strains that exhibited faster growth on sucrose, as described in Examples 1-7 herein, or were identified by saturation mutagenesis, as described in Examples 10-26 herein.

In one embodiment, the variant sucrose transporter polypeptides have an amino acid sequence that has at least 95% identity to an amino acid sequence as set forth in SEQ ID NO:24 based on a Clustal W method of alignment and having at least one amino acid change selected from the group consisting of:
  (i) leucine to proline at position 61;
  (ii) phenylalanine to leucine at position 159;
  (iii) glycine to cysteine at position 162;
  (iv) proline to histidine at position 169;
  (v) leucine to tryptophan at position 61;
  (vi) leucine to histidine at position 61;
  (vii) leucine to phenylalanine at position 61; and
  (viii) leucine to tyrosine at position 61.

In another embodiment, the variant sucrose transporter polypeptides have an amino acid sequence that has at least 95% identity to an amino acid sequence as set forth in SEQ ID NO:44 based on a Clustal W method of alignment and having a length of 402 to 407 amino acids from the N-terminus.

In another embodiment, the variant sucrose transporter polypeptides have an amino acid sequence that has at least 95% identity to an amino acid sequence as set forth in SEQ ID NO:44 based on a Clustal W method of alignment, having a length of 402 to 407 amino acids from the N-terminus, and having at least one of the amino acid changes listed above.

In another embodiment, the variant sucrose transporter polypeptides have an amino acid sequence selected from the group consisting of: SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, and SEQ ID NO:44.

Also disclosed herein are bacteria comprising in their genome or on at least one recombinant construct a nucleotide sequence encoding a variant sucrose transporter polypeptide, as described above, and a nucleotide sequence encoding a polypeptide having sucrose hydrolase activity. The bacteria may be variant or recombinant bacteria. The nucleotide sequences are each operably linked to the same or a different promoter. These bacteria metabolize sucrose at a greater rate than a bacterium containing a wild-type sucrose transporter polypeptide having an amino acid sequence as set forth in SEQ ID NO:24.

The variant bacteria comprising a nucleotide sequence encoding a variant sucrose transporter polypeptide, as described above, and a nucleotide sequence encoding a polypeptide having sucrose hydrolase activity in their genome may be isolated by growing wild-type bacterial strains containing a sucrose gene cluster, such as the cscAKB gene cluster (SEQ ID NO: 45) from *E. coli* ATCC®3281, on minimal sucrose medium and selected the faster growing strains, as described in Example 1 herein. Additionally, such variant bacteria may be produced by mutagenesis of bacterial strains containing a sucrose gene cluster, such as the cscAKB gene cluster (SEQ ID NO: 45) from *E. coli* ATCC®3281, for example, using saturation mutagenesis as described in Examples 10-26 herein.

Recombinant bacteria comprising a nucleotide sequence encoding a variant sucrose transporter polypeptide, as described above, and a nucleotide sequence encoding a polypeptide having sucrose hydrolase activity may be constructed by introducing the nucleotide sequences into a suitable host bacterium, either into the genome or on at least one recombinant construct, using methods known in the art, as described below. In some embodiments, the recombinant bacteria are capable of metabolizing sucrose to produce glycerol and/or glycerol-derived products.

Suitable host bacteria for use in the construction of the recombinant bacteria disclosed herein include, but are not limited to, organisms of the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces*, and *Pseudomonas*.

In one embodiment, the host bacterium is selected from the genera: *Escherichia, Klebsiella, Citrobacter*, and *Aerobacter*.

In another embodiment, the host bacterium is *Escherichia coli*.

In some embodiments, the host bacterium is PTS minus. In these embodiments, the host bacterium is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported.

The term "down-regulated" refers to reduction in, or abolishment of, the activity of active protein(s), as compared to the activity of the wild-type protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, etc.

The recombinant bacteria disclosed herein comprise a nucleotide sequence encoding a polypeptide having sucrose hydrolase activity. Polypeptides having sucrose hydrolase activity have the ability to catalyze the hydrolysis of sucrose to produce fructose and glucose. Polypeptides having sucrose hydrolase activity are known, and include, but are not limited to CscA from *E. coli* wild-type strain EC3132 (set forth in SEQ ID NO:47), encoded by gene cscA (coding sequence set forth in SEQ ID NO:46), CscA from *E. coli* ATCC®13821 (set forth in SEQ ID NO:49), encoded by gene cscA (coding sequence set forth in SEQ ID NO:48); BfrA from *Bifidobacterium* lactis strain DSM 10140$^T$ (set forth in SEQ ID NO:51), encoded by gene bfrA (coding sequence set forth in SEQ ID NO:50); Suc2p from *Saccharomyces cerevisiae* (set forth in SEQ ID NO:53), encoded by gene SUC2 (coding sequence set forth in SEQ ID NO:52); ScrB from *Corynebacterium glutamicum* (set forth in SEQ ID NO:55), encoded by gene scrB (coding sequence set forth in SEQ ID NO:54); sucrose phosphorylase from *Leuconostoc mesenteroides* DSM 20193 (set forth in SEQ ID NO:57), coding sequence of encoding gene set forth in SEQ ID NO:56; and sucrose phosphorylase from *Bifidobacterium adolescentis* DSM 20083 (set forth in SEQ ID NO:58), encoded by gene sucP (coding sequence set forth in SEQ ID NO:59).

In one embodiment, the polypeptide having sucrose hydrolase activity is classified as EC 3.2.1.26 or EC 2.4.1.7.

In another embodiment, the polypeptide having sucrose hydrolase activity has at least 95% sequence identity, based on the Clustal W method of alignment, to an amino acid sequence as set forth in SEQ ID NO:47, SEQ ID NO:49, SEQ ID NO:51, SEQ ID NO:53, SEQ ID NO:55, SEQ ID NO:57, or SEQ ID NO:59.

In another embodiment, the polypeptide having sucrose hydrolase activity corresponds substantially to the amino acid sequence set forth in SEQ ID NO:49.

The recombinant bacteria disclosed herein may also comprise a nucleotide sequence encoding a polypeptide having fructokinase activity. Polypeptides having fructokinase activity include fructokinases (designated EC 2.7.1.4) and various hexose kinases having fructose phosphorylating activity (EC 2.7.1.3 and EC 2.7.1.1). Fructose phosphorylating activity may be exhibited by hexokinases and ketohexokinases. Representative genes encoding polypeptides from a variety of microorganisms, which may be used to construct the recombinant bacteria disclosed herein, are listed in Table 1. One skilled in the art will know that proteins that are substantially similar to a protein which is able to phosphorylate fructose (such as encoded by the genes listed in Table 1) may also be used.

TABLE 1

Sequences Encoding Enzymes with Fructokinase Activity

| Source | Gene Name | EC Number | Nucleotide SEQ ID NO: | Protein SEQ ID NO: |
|---|---|---|---|---|
| *Agrobacterium tumefaciens* | scrK (fructokinase) | 2.7.1.4 | 60 | 61 |
| *Streptococcus mutans* | scrK (fructokinase) | 2.7.1.4 | 62 | 63 |
| *Escherichia coli* | scrK (fructokinase | 2.7.1.4 | 64 | 65 |
| *Klebsiella pneumoniae* | scrK (fructokinase | 2.7.1.4 | 66 | 67 |
| *Escherichia coli* | cscK (fructokinase) | 2.7.1.4 | 68 | 69 |
| *Enterococcus faecalis* | cscK (fructokinase) | 2.7.1.4 | 70 | 71 |
| *Saccharomyces cerevisiae* | HXK1 (hexokinase) | 2.7.1.1 | 72 | 73 |
| *Saccharomyces cerevisiae* | HXK2 (hexokinase) | 2.7.1.1 | 74 | 75 |

In one embodiment, the polypeptide having fructokinase activity is classified as EC 2.7.1.4, EC 2.7.1.3, or EC 2.7.1.1.

In another embodiment, the polypeptide having fructokinase activity has at least 95% sequence identity, based on the Clustal W method of alignment, to an amino acid sequence as set forth in SEQ ID NO:61, SEQ ID NO:63, SEQ ID NO:65, SEQ ID NO:67, SEQ ID NO:69, SEQ ID NO:71, SEQ ID NO:73, or SEQ ID NO:75.

In another embodiment, the polypeptide having fructokinase activity corresponds substantially to the sequence set forth in SEQ ID NO:65.

The coding sequence of the genes encoding polypeptides having polypeptides having sucrose hydrolase activity and polypeptides having fructokinase activity may be used to isolate nucleotide sequences encoding homologous polypeptides from the same or other microbial species. For example, homologs of the genes may be identified using sequence analysis software, such as BLASTN, to search publicly available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.*, 89: 392, (1992)). For example, the nucleotide sequence encoding the polypeptides described above may be employed as a hybridization probe for the identification of homologs.

One of ordinary skill in the art will appreciate that genes encoding these polypeptides isolated from other sources may also be used in the recombinant bacteria disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding variant sucrose transporter polypeptides, polypeptides having fructokinase activity, and polypeptides having sucrose hydrolase activity may be isolated using PCR (see, e.g., U.S. Pat. No. 4,683,202) and primers designed to bound the desired sequence, as described in the Examples herein. Other methods of gene isolation are well known to one skilled in the art such as by using degenerate primers or heterologous probe hybridization. The nucleotide sequences can also be chemically synthesized or purchased from vendors such as DNA2.0 Inc. (Menlo Park, Calif.).

Expression of the polypeptides may be effected using one of many methods known to one skilled in the art. For example, the nucleotide sequences encoding the polypeptides described above may be introduced into the bacterium on at least one multicopy plasmid, or by integrating one or more copies of the coding sequences into the host genome. The nucleotide sequences encoding the polypeptides may be introduced into the host bacterium separately (e.g., on separate plasmids) or in any combination (e.g., on a single plasmid). If the host bacterium contains a gene encoding one of the polynucleotides, then only the remaining nucleotide sequences need to be introduced into the bacterium. For example, if the host bacterium contains a nucleotide sequence encoding a polypeptide having fructokinase activity, only a nucleotide sequence encoding a polypeptide having sucrose transporter activity and a nucleotide sequence encoding a polypeptide having sucrose hydrolase activity need to be introduced into the bacterium to enable optimal sucrose utilization. The introduced coding regions that are either on a plasmid(s) or in the genome may be expressed from at least one highly active promoter. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, and lac, ara, tet, trp, $IP_L$, $IP_R$, T7, tac, and trc (useful for expression in *Escherichia coli*) as well as the amy, apr, npr promoters and various phage promoters useful for expression in *Bacillus*. The promoter may also be the *Streptomyces lividans* glucose isomerase promoter or a variant thereof, described by Payne et al. (U.S. Pat. No. 7,132,527).

In one embodiment, the recombinant bacteria disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host bacteria may be used that naturally produce glycerol. In addition, bacteria may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In another embodiment, the recombinant bacteria disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:76, encoded protein sequence set forth in SEQ ID NO:77).

Bacteria can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:
  phosphoenolpyruvate carboxylase typically characterized as EC 4.1.1.31
  cob(I)alamin adenosyltransferase, typically characterized as EC 2.5.1.17
  non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:
  aerobic respiration control protein
  methylglyoxal synthase
  acetate kinase
  phosphotransacetylase
  aldehyde dehydrogenase A
  aldehyde dehydrogenase B
  triosephosphate isomerase
  phosphogluconate dehydratase In another embodiment, the recombinant bacteria disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. Patent Application Publication No. 2011/0144377. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the E. coli gene aldB (coding sequence set forth in SEQ ID NO:15); AldA (SEQ ID NO:18), encoded by the E. coli gene aldA (coding sequence set forth in SEQ ID NO:17); and AldH (SEQ ID NO:20), encoded by the E. coli gene aldH (coding sequence asset forth in SEQ ID NO:19).

Many of the modifications described above to improve 1,3-propanediol production by a recombinant bacterium can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/ regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, Curr. Opin. Biotechnol. (1999) 10:411; Ross, et al., J. Bacteriol. (1998) 180:5375; deHaseth, et al., J. Bacteriol. (1998) 180:3019; Smolke and Keasling, Biotechnol. Bioeng. (2002) 80:762; Swartz, Curr. Opin. Biotech. (2001) 12:195; and Ma, et al., J. Bacteriol. (2002) 184:5733.

Recombinant bacteria containing the necessary changes in gene expression for metabolizing sucrose in the production of microbial products including glycerol and glycerol derivatives, as described above, may be constructed using techniques well known in the art, some of which are exemplified in the Examples herein.

The construction of the recombinant bacteria disclosed herein may be accomplished using a variety of vectors and transformation and expression cassettes suitable for the cloning, transformation and expression of coding regions that confer the ability to utilize sucrose in the production of glycerol and its derivatives in a suitable host microorganism. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of the instant polypeptides, nucleotide sequences encoding the polypeptides are linked operably through initiation codons to selected expression control regions such that expression results in the formation of the appropriate messenger RNA.

Particularly useful are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from *Klebsiella pneumoniae* and from *Saccharomyces cerevisiae*. Each vector contains the open reading frames dhaB1, dhaB2, dhaB3, dhaX (coding sequence set forth in SEQ ID NO:78; encoded polypeptide sequence set forth in SEQ ID NO:79), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:80, SEQ ID NO:81, SEQ ID NO:82, SEQ ID NO:83, and SEQ ID NO:84, respectively. The differences between the vectors are illustrated in the chart below [the prefix "p-" indicates a promoter; the open reading frames contained within each "( )" represent the composition of an operon]:

pSYCO101 (SEQ ID NO:80):
  p-trc (Dar1_GPP2) in opposite orientation compared to the other 2 pathway operons,
  p-1.6 long GI (dhaB1_dhaB2_dhaB3_dhaX), and p-1.6 long GI (orfY_orfX_orfW).
pSYCO103 (SEQ ID NO:81):
  p-trc (Dar1_GPP2) same orientation compared to the other 2 pathway operons,
  p-1.5 long GI (dhaB1_dhaB2_dhaB3_dhaX), and p-1.5 long GI (orfY_orfX_orfW).
pSYCO106 (SEQ ID NO:82):
  p-trc (Dar1_GPP2) same orientation compared to the other 2 pathway operons,
  p-1.6 long GI (dhaB1_dhaB2_dhaB3_dhaX), and p-1.6 long GI (orfY_orfX_orfW).
pSYCO109 (SEQ ID NO:83):
  p-trc (Dar1_GPP2) same orientation compared to the other 2 pathway operons,
  p-1.6 long GI (dhaB1_dhaB2_dhaB3_dhaX), and p-1.6 long GI (orfY_orfX).
pSYCO400/AGRO (SEQ ID NO:84):
  p-trc (Dar1_GPP2) same orientation compared to the other 2 pathway operons,
  p-1.6 long GI (dhaB1_dhaB2_dhaB3_dhaX), and
  p-1.6 long GI (orfY_orfX).
  p-1.20 short/long GI (scrK) opposite orientation compared to the pathway operons.

Once suitable expression cassettes are constructed, they are used to transform appropriate host bacteria. Introduction of the cassette containing the coding regions into the host bacterium may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology, Second Edition* (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise sucrose as a carbon substrate. Other carbon substrates such as glucose and fructose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae, Klebsiella species, Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other bacteria, capable of de novo vitamin $B_{12}$ biosynthesis will also be suitable production cells and the addition of vitamin $B_{12}$ to these bacteria will be unnecessary.

Typically bacterial cells are grown at 25 to 40° C. in an appropriate medium containing sucrose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In one embodiment, a process for making glycerol, 1,3-propanediol, and/or 3-hydroxypropionic acid from sucrose is provided. The process comprises the steps of culturing a recombinant bacterium, as described above, in the presence of sucrose, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation. For example, a process for purifying biologically produced 1,3-propanediol is described in U.S. Pat. No. 7,919,658.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

GENERAL METHODS

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., Short Protocols in *Molecular Biology*, $5^{th}$ Ed. Current Protocols, John Wiley and Sons, Inc., N.Y., 2002.

Materials and Methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology: Washington, D.C. (1994)); or in *Manual of Industrial Microbiology and Biotechnology*, 3$^{rd}$ Edition (Richard H. Baltz, Julian E. Davies, and Arnold L. Demain Eds.), ASM Press, Washington, D.C., 2010. All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.).

The meaning of abbreviations is as follows: "sec" means second(s), "min" means minute(s), "h" means hour(s), "nm" means nanometer(s), "μL" means microliter(s), "mL" means milliliter(s), "L" means liter(s), "mM" means millimolar, "M" means molar, "g" means gram(s), "μg" means microgram(s), "ng" means nanogram(s), "bp" means base pair(s), "kbp" means kilobase pair(s), "rpm" means revolutions per minute, "ATCC" means American Type Culture Collection, Manassas, Va., "OD" means optical density, "g" means the gravitation constant, "HPLC" means high performance liquid chromatography.

TABLE 2

Primers used in the Examples

| Primer | Sequence | SEQ ID NO: |
|---|---|---|
| aldH cscA | TAGACGTGAAACAGGAGTCATAATGAATTTTTCATCATCTGGGATCCCTTGCCCGCTGTTG | 85 |
| aldH cscB | CATTTCAGGCCTCCAGGCTTATCCAGATGGTTTTCAGTTCGAATTCGCAGGACCGTGATA | 86 |
| aldH_check_up | TGAGCGAATCCCGATGAGCTTACT | 87 |
| aldH_check_dn | ATACGTTCGCGGATGATCTCACCA | 88 |
| yihP cscA | ACCATTGTGGCGATGGGTTGCTTCTACAGCCTGAACGAGAGGATCCCTTGCCCGCTGTG | 89 |
| yihP cscB | TTACGGGCTTCTATCTCTTCCACAATGCGGACATACATCTGAATTCGCAGGACCGTGATA | 90 |
| cscB61up Kan | ATTAGGTACACTTTATTCGGTCAACCAGTTTACCAGCATTCGTCTTGAGCGATTGTGTAG | 91 |
| cscB353 down kan | TCGGCGTTGAAAGCAGCACAATCCCAAGCGAACTGGCAATTGAATATCCTCCTTAGTTCC | 92 |
| cscB 5' | ATGGCACTGAATATTCCATTC | 93 |
| cscB 3' | CTATATTGCTGAAGGTACAG | 94 |
| 61NNK top2 | ATTAGGTACACTTTATTCGGTCAACCAGTTTACCAGCATTNNNTTTATGATGTTCTACGG | 95 |
| Q353 down2 | TCGGCGTTGAAAGCAGCACAATCCCAAGCGAACTGGCAATTTGAAAACCAATCAGAAAGA | 96 |
| cscB5-119-F | ATCTAGGGTTGACAGGGACGGAAT | 97 |
| GC-cscB_F1 | AAGCTATCAAGCAAACCGCATCCC | 98 |

Example 1

Isolation of Variant *E. coli* Strains Showing Faster Sucrose Utilization

This Example describes the isolation of variant *E. coli* strains that showed faster sucrose utilization. These variants occurred spontaneously or due to PCR errors when amplifying the sucrose gene cluster.

The cscAKB gene cluster (SEQ ID NO: 45) from *E. coli* ATCC®3281 was introduced into PDO producing strain TTab pSYCO400/AGRO to enable PDO production from sucrose. *E. coli* strain TTab pSYCO400/AGRO, a PTS minus strain, was constructed as follows. Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:99 and SEQ ID NO:100 using pKD3 as the template. The primer SEQ ID NO:99 contains 80 by of homology to the 5'-end of aldB and 20 by of homology to pKD3. Primer SEQ ID NO:100 contains 80 by of homology to the 3' end of aldB and 20 by homology to pKD3. The PCR products were gel-purified and electroporated into MG1655/pKD46 competent cells (U.S. Pat. No. 7,371,558). Recombinant strains were selected on LB (Luria Bertani) plates with 12.5 mg/L of chloramphenicol. The deletion of the aldB gene was confirmed by PCR, using the primer pair SEQ ID NO:101 and SEQ ID NO:102. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:101 and SEQ ID NO:102 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:84), described in U.S. Pat. No. 7,524,660 (Example 4), to generate strain TTab pSYCO400/AGRO.

As described in the cited references, strain TTab is a derivative of *E. coli* strain FM5 (ATCC® No. 53911) containing the following modifications:

deletion of glpK, gldA, ptsHI, crr, edd, arcA, mgsA, qor, ackA, pta, aldA and aldB genes;

upregulation of galP, glk, btuR, ppc, and yqhD genes; and downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

The cscAKB gene cluster (SEQ ID NO: 45) was integrated at the aldH location in TTab pSYCO400/AGRO by the Lambda Red method. The cscAKB gene cluster was amplified from plasmid pBHR-cscBKA (SEQ ID NO:103), which was constructed as described in Example 1 of U.S. Patent Application Publication No. 2011/0136190 A1, using aldH cscA primer (SEQ ID NO:85) and aldH cscB primer (SEQ ID NO:86) containing flanking sequences for the aldH gene. Plasmid pBHR-cscBKA, linearized by PstI digest, was used as the PCR template. High fidelity PfuUltra® II Fusion HS DNA polymerase (Stratagene; La Jolla, Calif.) was used in the PCR reaction. PCR was performed using the following cycling conditions: 95° C. for 2 min; 35 cycles of 95° C. for 30 sec, 60° C. for 30 sec, and 72° C. for 4 min; and then 72° C. for 7 min. The resulting PCR product was stored at 4° C. The PCR product was purified using a QIAquick PCR Purification kit (Qiagen, Valencia, Calif.). The PCR product was electroporated into the TTab pSYCO400/AGRO strain containing the pKD46 plasmid (Red recombinase plasmid, GenBank Acc. No. AY048746), encoding lambda recombinases, following the lambda red recombination procedure (Datsenko, K. A. and Wanner, B. L., 2000, *Proc. Natl. Acad. Sci. USA* 97, 6640-6645). The transformation mixture was plated on MOPS minimal plates containing 10 g/L sucrose and 100 µg/mL spectinomycin. The MOPS minimal plates contained 1XMOPS buffer (Technova, Hollister, Calif.), 1.32 mM KH$_2$PO$_4$ (Technova), 50 µg/L uracil and 1.5 g/L Bacto agar. Plates were incubated at 37° C. for 2-3 days. Colonies grown on minimal sucrose plates were picked and growth in sucrose liquid medium was examined using a Bioscreen C growth chamber (Bioscreen, Helsinki, Finland). For the Bioscreen growth assay, colonies were first grown in 150 µL of LA medium (1% tryptone, 0.5% yeast extract, 0.05% sodium chloride) containing 100 µg/mL spectinomycin in a Costar 96-well U bottom microtiter plate (Corning Inc., Corning, N.Y.). The microtiter plate was incubated at 37° C. with shaking overnight. The fresh overnight cultures were diluted 1:100 into MOPS minimal medium containing 2.5 g/L sucrose and 100 µg/mL spectinomycin in a Bioscreen honeycomb plate. Vitamin B$_{12}$ was added to the medium to a concentration of 0.1 mg/L. The honeycomb plate was placed into the Bioscreen C instrument according to the manufacturer's instructions. The plate was incubated at 33° C. with constant shaking and the OD was recorded every 15 min. Most isolates grew slowly in 2.5 g/L sucrose, but a few grew faster. These faster growing variants were selected for further analysis.

Examples 2-7

Identification of Variant Sucrose Transporter Genes

These Examples describe the identification of variant sucrose transporter genes. These sucrose transporter variants enabled faster sucrose utilization.

The sucrose gene cluster in the faster growing *E. coli* variants described in Example 1 was amplified by PCR and the whole gene cluster sequence in these strains was determined by DNA sequencing. Six variants were identified, as shown in Table 3, all containing a single base pair change in the cscB gene. Four of the variants had a single amino acid substitution, and two of the variants had truncations at the C-terminal end. None of the variants had an amino acid substitution in the cscA gene and only one variant had an amino acid substitution in the cscK gene.

TABLE 3

Sucrose Transporter Variants in a PDO Production Strain

| Example | Variant Strain | Nucleotide change[a] in cscB | cscB Nucleotide SEQ ID NO: | Amino acid substitution[b] in CscB | CscB Amino Acid SEQ ID NO: |
|---|---|---|---|---|---|
| 2 | PDO3097 | T182C | 25 | L61P | 26 |
| 3 | PDO3214 | C477A | 27 | F159L | 28 |
| 4 | PDO3215 | G484T | 29 | G162C | 30 |
| 5 | PDO3216 | C506A | 31 | P169H | 32 |

TABLE 3-continued

Sucrose Transporter Variants in a PDO Production Strain

| Example | Variant Strain | Nucleotide change[a] in cscB | cscB Nucleotide SEQ ID NO: | Amino acid substitution[b] in CscB | CscB Amino Acid SEQ ID NO: |
|---|---|---|---|---|---|
| 6 | PDO3217[c] | G1207T | 41 | E403STOP | 42 |
| 7 | PDO3218 | G1222T | 43 | E408STOP | 44 |

[a]The nomenclature used to indicate the nucleotide change is: the first letter is the symbol for the wild-type nucleotide, the number is its position, and the following letter is the symbol for the nucleotide in the variant.
[b]The nomenclature used to indicate the amino acid substitution is: the first letter is the single letter symbol for the wild-type amino acid, the number is its position, and the following letter is the single letter symbol for the amino acid in the variant.
[c]PDO3217 also had a G93W mutation in the cscK gene.

The growth rate of the *E. coli* strains containing the variant sucrose transporter in a sucrose containing medium was determined using the Bioscreen C instrument. The *E. coli* variants were grown in 3 mL of LA medium containing 100 µg/mL spectinomycin at 37° C. for 16 hours. For the Bioscreen assay, the fresh overnight cultures were diluted 1:100 into MOPS minimal medium containing 2.5 g/L, 5 g/L or 10 g/L sucrose and 100 µg/mL spectinomycin in a Bioscreen honeycomb plate. Vitamin B$_{12}$ was added to the medium to a concentration of 0.1 mg/L. Four replicates were run for each sample. Medium blank wells were also included. The honeycomb plate was placed into the Bioscreen C instrument according to the manufacturer's instructions. The plate was incubated at 33° C. with constant shaking and the OD was recorded every 15 min. An *E. coli* strain containing the wild-type sucrose gene cluster was grown in the same manner to serve as a control. The maximum growth rate, referred to herein as $\mu_{max}$, was estimated using the following procedure. First, the background was removed by subtracting the averaged OD values in the blank wells from the OD values of non-blank wells. Then, the growth rate parameter was estimated using a sliding window consisting of 8 data points (covering 2 hours of growth) by fitting the data points to an exponential curve using non-linear regression. In each sliding window, the estimated growth rate was recorded only if the fit was good (i.e., $R^2 > 0.95$). The largest value from all the recorded growth rates was taken as $\mu_{max}$. The mean $\mu_{max}$ and the standard deviation of four replicates are given in Table 4.

TABLE 4

Growth Rates of *E. coli* Variants Grown on Sucrose

| | Growth Rate ($\mu_{max}$) on Sucrose | | |
|---|---|---|---|
| Variant Strain | 2.5 g/L | 5 g/L | 10 g/L |
| PDO3084 (Control) | 0.056 ± 0.017 | 0.120 ± 0.003 | 0.223 ± 0.002 |
| PDO3097 | 0.196 ± 0.002 | 0.290 ± 0.001 | 0.278 ± 0.005 |
| PDO3214 | 0.091 ± 0.006 | 0.209 ± 0.007 | 0.270 ± 0.001 |
| PDO3215 | 0.136 ± 0.003 | 0.253 ± 0.001 | 0.273 ± 0.001 |
| PDO3216 | 0.152 ± 0.003 | 0.244 ± 0.004 | 0.251 ± 0.005 |
| PDO3217 | 0.076 ± 0.004 | 0.185 ± 0.003 | 0.276 ± 0.007 |
| PDO3218 | 0.048 ± 0.002 | 0.161 ± 0.003 | 0.256 ± 0.002 |

As can be seen from the results in Table 4, the variant *E. coli* strains grew faster on sucrose than the control strain.

Example 8

PDO and Glycerol Production by Variant *E. coli* Strains Grown on Sucrose

This Example describes the production of PDO and glycerol by the *E. coli* variants described in Example 1, when grown on sucrose. The variant strains showed an increased molar yield for the production of PDO and glycerol compared to a control strain containing the wild-type sucrose gene cluster.

The molar yield for production of PDO and glycerol was determined in shake flask studies. Fresh overnight cultures of the *E. coli* variants were inoculated into 12.5 mL MOPS medium containing 10 g/L sucrose plus 100 ng/mL Vitamin B12 and 100 μg/mL spectinomycin to an initial OD of 0.01. Cells were grown at 33° C. with shaking at 250 rpm for 44 hours. Cultures were centrifuged and the supernatants were added to 0.22 μm Spin-X centrifuge tube filters (Corning Inc., Corning, N.Y.) and centrifuged at 10,000 g for 1 min. The filtrates were analyzed by HPLC using a Waters Alliance 2690 HPLC system (Waters Corp., Milford, Mass.) with an Aminex HPX-87C HPLC carbohydrate analysis column (Bio-Rad Laboratories, Hercules, Calif., Cat #125-0095) heated to 85° C. in a separated Waters TCM heating chamber. A Bio-Rad carbo-C micro-guard column (Bio-Rad, Cat #125-0128) was used before the analysis column. The mobile phase was composed of 0.05 mM CaO (Sigma, #208159), 0.5 mM MES (Sigma, #M3671), 0.05 mM $HNO_3$ (EMD Chemicals, Gibbstown, N.J., Cat #NX0409), pH 5.3. The flow rate was 0.5 mL/min. Typically, the retention times of PDO and glycerol were 17.5 min and 19.3 min, respectively. The retention times of sucrose, glucose and fructose were 10.3 min, 12.5 min and 15.9 min, respectively. Consistent with the faster growth rates observed with the Bioscreen assay, the variant *E. coli* strains also showed faster sucrose consumption in shake flasks. In addition, the variant *E. coli* strains all showed higher molar yield for production of PDO and glycerol (i.e., moles of PDO and glycerol per mole of sucrose) than the wild-type control, as shown in Table 5.

TABLE 5

Molar Yield for the Production of PDO and Glycerol by Variant *E. coli* Strains Grown on Sucrose

| Variant Strain | Molar Yield (mol PDO + glycerol/mol sucrose) |
|---|---|
| PDO3084 (Control) | 1.120 |
| PDO3097 | 1.204 |
| PDO3214 | 1.170 |
| PDO3215 | 1.197 |
| PDO3216 | 1.189 |
| PDO3217 | 1.175 |
| PDO3218 | 1.169 |

Example 9

Recombinant Bacteria Containing Variant Sucrose Transporter Genes

This Example describes the construction of recombinant bacteria containing variant sucrose transporter genes. The recombinant bacteria had the ability to utilize sucrose faster than a wild-type control strain.

The sucrose gene clusters containing the variant cscB genes were amplified from the sequenced variant strains by PCR using conditions as described in Example 1. The PCR products were transformed into a parental host, *E. coli* strain FM5 (ATCC® No. 53911), containing the pKD46 plasmid, as described in Example 1. Integrants containing the variant clusters were selected by growing on MOPS minimal plates containing 10 g/L sucrose. Colonies were streaked and integrants that cured of pKD46 were purified. A representative colony from each strain was selected. Integration of the sucrose gene cluster at the aldH gene was confirmed by PCR using primer aldH_check_up (SEQ ID NO: 87) and primer aldH_check_dn (SEQ ID NO:88). The original cscB mutation in each of the strains was confirmed by sequencing the PCR product containing the sucrose gene cluster. No additional mutation was found. Growth rates of the FM5 derived strains grown on sucrose were determined using the Bioscreen assay as described in Examples 2-7. The results (i.e., the mean and standard deviation of three replicates) are shown in Table 6.

TABLE 6

Growth Rates of FM5 Derived Strains Containing Variant Sucrose Gene Clusters

| Variant Strain | CscB Amino Acid SEQ ID NO: | Growth Rate ($\mu_{max}$) on Sucrose | | |
|---|---|---|---|---|
| | | 1 g/L | 2.5 g/L | 10 g/L |
| PDO3257 (Control) | 24 | 0.115 ± 0.010 | 0.247 ± 0.002 | 0.449 ± 0.006 |
| PDO3094 | 26 | 0.223 ± 0.045 | 0.476 ± 0.007 | 0.485 ± 0.007 |
| PDO3219 | 28 | 0.220 ± 0.004 | 0.385 ± 0.005 | 0.447 ± 0.004 |
| PDO3220 | 30 | 0.181 ± 0.024 | 0.431 ± 0.026 | 0.466 ± 0.010 |
| PDO3221 | 32 | 0.174 ± 0.073 | 0.469 ± 0.001 | 0.491 ± 0.009 |
| PDO3222[a] | 42 | 0.115 ± 0.025 | 0.347 ± 0.003 | 0.449 ± 0.002 |
| PDO3223 | 44 | 0.162 ± 0.008 | 0.399 ± 0.003 | 0.457 ± 0.005 |

[a]PDO3222 also had a G93W mutation in the cscK gene.

As can be seen from the results in Table 6, the *E. coli* strains containing the variant sucrose transporter genes grew faster than the wild-type strain at the lower sucrose levels.

Examples 10-26

Identification of Variant Sucrose Transporter Polypeptides by Saturation Mutagenesis These Examples describe the identification of variant sucrose transporters by saturation mutagenesis at residue 61 of the CscB protein on the chromosome. In addition to the L61P mutation previously identified from spontaneous mutation, several other amino acid changes at residue 61 also enabled faster sucrose utilization at low sucrose concentration.

In order to perform saturation mutagenesis directly on the chromosome, a cscA+K+ B– (kanR) strain was constructed in *E. coli* strain FM5. The starting strain PDO3085 contained the wild-type cscAKB gene cluster integrated at the yihP gene in FM5. Integration of the sucrose cluster at the yihP gene was accomplished as described in Example 3 except that yihP cscA primer (SEQ ID NO:89) and yihP cscB primer (SEQ ID NO:90) were used. The cscB gene in the cluster in PDO3085 was then partially deleted by replacing it with a kanamycin resistance cassette. The kanamycin resistance cassette was amplified from the pKD4 template plasmid (Datsenko and Wanner, *Proc. Natl. Acad. Sci. USA* 97:6640-6645, 2000) using cscB61 up kan primer (SEQ ID NO:91) and cscB353 down kan primer (SEQ ID NO:92). High fidelity PfuUltra® II Fusion HS DNA polymerase (Stratagene; La Jolla, Calif.) was used in the PCR reaction. PCR was performed using the following cycling conditions: 95° C. for 2 min; 30 cycles of 95° C. for 20 sec, 60° C. for 20 sec, and 72° C. for 1.5 min; and then 72° C. for 3 min. The resulting PCR product was stored at 4° C. The PCR product was purified using the QIAquick PCR Purification kit (Qiagen). The PCR product was electroporated into the PDO3085 strain containing the pKD46 plasmid encoding lambda recombinases following the lambda red recombination procedure. The transformation mixture was plated on LB plates containing 25 µg/mL kanamycin. The kanamycin resistance colonies were checked on MOPS+10 g/L sucrose plates to make sure that they were unable to grow on sucrose. Insertion of the kanamycin resistance cassette between residue 61 and 353 of CscB was confirmed by PCR using cscB 5' primer (SEQ ID NO:93) and cscB 3' primer (SEQ ID NO: 94). This FM5 yihP:cscA+K+B-(Δ61-353, kanR) strain designated as PDO 3513 was used as the host strain for saturation mutagenesis.

The oligos containing the mutagenic residues at position 61 were synthesized by Integrated DNA Technologies (Coralville, Iowa) as NNK at position 61 (N=any nucleotide; K=G or T). The 61 NNK top2 oligos (SEQ ID NO: 95) and Q353 down2 oligo (SEQ ID NO: 96) were used as primers to amplify the internal cscB fragment (61-353 residues) using PDO3085 as template. PCR conditions were similar to those described above in this Example, except that AccuStart Super Mix (Quanta Biosciences, Inc. Gaithersburg, Md.) containing Taq DNA polymerase was used. The PCR product was purified using the Zymo DNA Clean kit (Zymo Research Corp., Irvine, Calif.) and transformed into PDO3513 containing pKD46 following the Lambda Red protocol. The transformation mixture was plated out on MOPS plates containing 2.5 g/L sucrose and 5 g/L tetracycline (FM5 cells are resistant to tetracycline). Plates were incubated at 37° C. for about two days. A total of 96 isolated colonies were picked and cultured in MOPS medium with 10 g/L sucrose and 5 g/L tetracycline in a 96 deep-well plate at 37° C. overnight. The cells were all confirmed to have the sucrose gene cluster at the yihP gene location by PCR. Each isolate was streaked on LB plates and a single colony from each isolate was resuspended in water in a 96 well PCR plate. The cell suspension was used for GenomiPhi sequencing (GE Health Care, Piscataway, N.J.) to identify the cscB mutation using primers cscB5-119-F (SEQ ID NO:97) and GC-cscB_F1 (SEQ ID NO:98) that covered position 61. A total of 78 isolates (about 81%) were successfully sequenced by GenomiPhi. Among the sequenced isolates, 16 different amino acid residues were identified at codon 61 (Table 7). The full length of the cscB gene was subsequently sequenced from at least one representative of each of the amino acid variants which exhibited a high growth rate on sucrose to check if any other mutation occurred elsewhere in the gene. These isolates were also cured of pKD46 and used in the Bioscreen assay for growth in sucrose medium.

Among the 96 colonies obtained from NNK saturation mutagenesis, 7 of them had the wild-type residue leucine at position 61, although the amino acid was encoded by different codons (CTG or TTG) from the original CTA in the wild-type cscB gene. These variants grew similarly on sucrose in the Bioscreen assay as the original wild-type control. Fifteen L61P variants were also isolated and encoded by different codons (CCG or CCT) from the original isolate (CCA) as described in earlier Examples. These L61P variants all showed faster growth rates on sucrose, similar to the original L61P variant. Besides the L61P variant, L61W and L61F also showed much faster growth on sucrose than the wild-type control. The L61H, and L61Y variants showed slightly faster growth on sucrose than the wild-type control. Variants L61A, L61E, L61G, L61K showed similar growth rate on sucrose as the wild-type control. Variants L61D, L61Q, L61S, L61T and L61V showed much slower growth on sucrose than the wild-type control. Two isolates of variant L61I showed quite different growth on sucrose; one had similar growth to the wild-type, and one had much faster growth than the wild-type. Both isolates were sequenced and were found to contain no other mutations in the cscB gene in addition to the ATT at codon 61. It is possible that some other spontaneous mutation elsewhere caused the different growth phenotypes for the two L61I isolates.

TABLE 7

Characterization of the NNK Saturation Variants at Codon 61 of CscB

| Example | 61NNK-FM5 derived strains | CscB Amino Acid SEQ ID NO: | Codon 61 | No. of isolates | Growth rate ($\mu_{max}$) on sucrose | | |
|---|---|---|---|---|---|---|---|
| | | | | | 1 g/L | 2.5 g/L | 10 g/L |
| 10, Comparative | L61 wt | 24 | CTA | na[a] | 0.136 ± 0.007 | 0.317 ± 0.003 | 0.435 ± 0.015 |
| 2 | L61P | 26 | CCA | original | 0.227 ± 0.004 | 0.372 ± 0.001 | 0.376 ± 0.003 |
| 11, Comparative | L61A[b] | 104 | GCT | 1 | 0.145 ± 0.002 | 0.330 ± 0.008 | 0.435 ± 0.002 |
| 12, Comparative | L61D[c] | 105 | GAT | 5 | 0.046 ± 0.003 | 0.128 ± 0.002 | 0.167 ± 0.006 |
| 13, Comparative | L61E | 106 | GAG | 2 | 0.140 ± 0.002 | 0.328 ± 0.003 | 0.381 ± 0.004 |
| 14 | L61F | 38 | TTT | 10 | 0.194 ± 0.001 | 0.372 ± 0.003 | 0.412 ± 0.005 |
| 15, Comparative | L61G | 107 | GGT/GGG | 5 | 0.124 ± 0.002 | 0.302 ± 0.003 | 0.385 ± 0.002 |
| 16 | L61H | 36 | CAT | 2 | 0.168 ± 0.002 | 0.347 ± 0.001 | 0.410 ± 0.004 |
| 17, Comparative (#68) | L61I | 108 | ATT | 1 | 0.115 ± 0.001 | 0.293 ± 0.000 | 0.396 ± 0.004 |

TABLE 7-continued

Characterization of the NNK Saturation Variants at Codon 61 of CscB

| Example | 61NNK-FM5 derived strains | CscB Amino Acid SEQ ID NO: | Codon 61 | No. of isolates | Growth rate ($\mu_{max}$) on sucrose | | |
|---|---|---|---|---|---|---|---|
| | | | | | 1 g/L | 2.5 g/L | 10 g/L |
| 17, Comparative | L61I (#71) | 108 | ATT | 1 | 0.211 ± 0.013 | 0.383 ± 0.005 | 0.434 ± 0.001 |
| 18, Comparative | L61K | 109 | AAG | 1 | 0.121 ± 0.002 | 0.287 ± 0.003 | 0.372 ± 0.004 |
| 19, Comparative | L61L | 24 | CTG/TTG | 7 | 0.111 ± 0.003 | 0.268 ± 0.003 | 0.399 ± 0.006 |
| 20 | L61P | 26 | CCG/CCT | 15 | 0.243 ± 0.004 | 0.397 ± 0.003 | 0.438 ± 0.001 |
| 21, Comparative | L61Q[c] | 110 | CAG | 3 | 0.035 ± 0.007 | 0.046 ± 0.013 | 0.083 ± 0.001 |
| 22, Comparative | L61S[c] | 111 | TCG | 1 | 0.034 ± 0.001 | 0.036 ± 0.003 | 0.090 ± 0.004 |
| 23, Comparative | L61T[c] | 112 | ACG | 1 | 0.036 ± 0.004 | 0.047 ± 0.001 | 0.061 ± 0.001 |
| 24, Comparative | L61V[c] | 113 | GTT | 1 | 0.052 ± 0.006 | 0.079 ± 0.005 | 0.111 ± 0.001 |
| 25 | L61W | 34 | TGG | 19 | 0.257 ± 0.007 | 0.401 ± 0.008 | 0.443 ± 0.007 |
| 26 | L61Y | 40 | TAT | 3 | 0.164 ± 0.000 | 0.343 ± 0.008 | 0.389 ± 0.002 |

[a]na means not applicable.
[b]L61A has two additional mutations K287R and I296V in CscB.
[c]Not confirmed by full length sequencing of cscB.

What is claimed is:

1. A variant sucrose transporter polypeptide having:
an amino acid sequence that has at least 95% identity to an amino acid sequence as set forth in SEQ ID NO:24 based on a Clustal W method of alignment and having at least one amino acid change selected from the group consisting of:

(i) leucine to proline at position 61;
(ii) leucine to tryptophan at position 61;
(iii) leucine to histidine at position 61;
(iv) leucine to phenylalanine at position 61; and
(v) leucine to tyrosine at position 61.

* * * * *

SEQUENCE LISTING

<160> NUMBER OF SEQ ID NOS: 113

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
atcgtttca acattccaca tcaattttg ccccgtatct gtagccaatt gaaaggtcat       420
gttgattcac acgtcagagc tatctcctgt ctaaagggt tgaagttgg tgctaaaggt       480
gtccaattgc tatcctctta catcactgag gaactaggta ttcaatgtgg tgctctatct     540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
```

-continued

```
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgctgggga atgtgaaaag gagttgttga atggccaatc cgctcaaggt   1020
ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                             1176
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285
```

```
Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 3
<211> LENGTH: 1323
<212> TYPE: DNA
<213> ORGANISM: Saccharomyces cerevisiae

<400> SEQUENCE: 3

```
atgcttgctg tcagaagatt aacaagatac acattcctta agcgaacgca tccggtgtta    60
tatactcgtc gtgcatataa aattttgcct tcaagatcta ctttcctaag aagatcatta   120
ttacaaacac aactgcactc aaagatgact gctcatacta atatcaaaca gcacaaacac   180
tgtcatgagg accatcctat cagaagatcg gactctgccg tgtcaattgt acatttgaaa   240
cgtgcgccct tcaaggttac agtgattggt tctggtaact gggggaccac catcgccaaa   300
gtcattgcgg aaaacacaga attgcattcc catatcttcg agccagaggt gagaatgtgg   360
gttttttgatg aaaagatcgg cgacgaaaat ctgacggata tcataaatac aagacaccag   420
aacgttaaat atctacccaa tattgacctg ccccataatc tagtggccga tcctgatctt   480
ttacactcca tcaagggtgc tgacatcctt gttttcaaca tccctcatca atttttacca   540
aacatagtca acaattgca aggccacgtg gccccctcatg taagggccat ctcgtgtcta   600
aaagggttcg agttgggctc caagggtgtg caattgctat cctcctatgt tactgatgag   660
ttaggaatcc aatgtggcgc actatctggt gcaaacttgg caccggaagt ggccaaggag   720
cattggtccg aaaccaccgt ggcttaccaa ctaccaaagg attatcaagg tgatggcaag   780
gatgtagatc ataagatttt gaaattgctg ttccacagac cttacttcca cgtcaatgtc   840
atcgatgatg ttgctggtat atccattgcc ggtgccttga gaacgtcgt ggcacttgca   900
tgtggtttcg tagaaggtat gggatggggt aacaatgcct ccgcagccat tcaaaggctg   960
ggtttaggtg aaattatcaa gttcggtaga atgttttcc cagaatccaa agtcgagacc  1020
tactatcaag aatccgctgg tgttgcagat ctgatcacca cctgctcagg cggtagaaac  1080
gtcaaggttg ccacatacat ggccaagacc ggtaagtcag ccttggaagc agaaaaggaa  1140
ttgcttaacg gtcaatccgc ccaagggata atcacatgca gagaagttca cgagtggcta  1200
caaacatgtg agttgaccca agaattccca ttattcgagg cagtctacca gatagtctac  1260
aacaacgtcc gcatggaaga cctaccggag atgattgaag agctagacat cgatgacgaa  1320
tag                                                                 1323
```

<210> SEQ ID NO 4
<211> LENGTH: 440
<212> TYPE: PRT

<213> ORGANISM: Saccharomyces cerevisiae

<400> SEQUENCE: 4

```
Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
```

```
                      405                 410                 415
Gln Ile Val Tyr Asn Asn Val Arg Met Glu Asp Leu Pro Glu Met Ile
            420                 425                 430

Glu Glu Leu Asp Ile Asp Asp Glu
        435                 440

<210> SEQ ID NO 5
<211> LENGTH: 816
<212> TYPE: DNA
<213> ORGANISM: Saccharomyces cerevisiae

<400> SEQUENCE: 5
atgaaacgtt tcaatgtttt aaaatatatc agaacaacaa aagcaaatat acaaaccatc    60
gcaatgcctt tgaccacaaa acctttatct ttgaaaatca cgccgctct attcgatgtt    120 gacggtacca tcatcatctc tcaaccagcc attgctgctt tctggagaga tttcggtaaa    180
gacaagcctt acttcgatgc cgaacacgtt attcacatct ctcacggttg gagaacttac    240
gatgccattg ccaagttcgc tccagacttt gctgatgaag aatacgttaa caagctagaa    300
ggtgaaatcc cagaaaagta cggtgaacac tccatcgaag ttccaggtgc tgtcaagttg    360
tgtaatgctt tgaacgcctt gccaaaggaa aaatgggctg tcgccacctc tggtacccgt    420
gacatggcca gaaatggtt cgacattttg aagatcaaga gaccagaata cttcatcacc    480
gccaatgatg tcaagcaagg taagcctcac ccagaaccat acttaaaggg tagaaacggt    540
ttgggtttcc caattaatga acaagaccca tccaaatcta aggttgttgt ctttgaagac    600
gcaccagctg gtattgctgc tggtaaggct gctggctgta aatcgttgg tattgctacc    660 actttcgatt ggacttctt gaaggaaaag ggttgtgaca tcattgtcaa gaaccacgaa    720
tctatcagag tcggtaata aacgctgaa accgatgaag tcgaattgat ctttgatgac    780
tacttatacg ctaaggatga cttgttgaaa tggtaa                              816

<210> SEQ ID NO 6
<211> LENGTH: 271
<212> TYPE: PRT
<213> ORGANISM: Saccharomyces cerevisiae

<400> SEQUENCE: 6

Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
```

```
            145                 150                 155                 160
Ala Asn Asp Val Lys Gln Gly Lys Pro His Pro Glu Pro Tyr Leu Lys
                    165                 170                 175
Gly Arg Asn Gly Leu Gly Phe Pro Ile Asn Glu Gln Asp Pro Ser Lys
                180                 185                 190
Ser Lys Val Val Val Phe Glu Asp Ala Pro Ala Gly Ile Ala Ala Gly
            195                 200                 205
Lys Ala Ala Gly Cys Lys Ile Val Gly Ile Ala Thr Thr Phe Asp Leu
        210                 215                 220
Asp Phe Leu Lys Glu Lys Gly Cys Asp Ile Ile Val Lys Asn His Glu
225                 230                 235                 240
Ser Ile Arg Val Gly Glu Tyr Asn Ala Glu Thr Asp Glu Val Glu Leu
                245                 250                 255
Ile Phe Asp Asp Tyr Leu Tyr Ala Lys Asp Asp Leu Leu Lys Trp
            260                 265                 270

<210> SEQ ID NO 7
<211> LENGTH: 753
<212> TYPE: DNA
<213> ORGANISM: Saccharomyces cerevisiae

<400> SEQUENCE: 7
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc     300 aacgctttga acgctctacc aaaagagaaa tgggctgtgg caacttccgg tacccgtgat     360
atggcacaaa aatggttcga gcatctggga atcaggagac caaagtactt cattaccgct     420
aatgatgtca acagggtaa gcctcatcca gaaccatatc tgaagggcag gaatggctta     480
ggatatccga tcaatgagca agaccccttcc aaatctaagg tagtagtatt tgaagacgct     540
ccagcaggta ttgccgccgg aaaagccgcc ggttgtaaga tcattggtat tgccactact     600
ttcgacttgg acttcctaaa ggaaaaaggc tgtgacatca ttgtcaaaaa ccacgaatcc     660
atcagagttg gcggctacaa tgccgaaaca gacgaagttg aattcatttt tgacgactac     720
ttatatgcta aggacgatct gttgaaatgg taa                                   753

<210> SEQ ID NO 8
<211> LENGTH: 250
<212> TYPE: PRT
<213> ORGANISM: Saccharomyces cerevisiae

<400> SEQUENCE: 8

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
65                  70                  75                  80
```

```
Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9 atg aaa aga tca aaa cga ttt gca gta ctg gcc cag cgc ccc gtc aat    48
Met Lys Arg Ser Lys Arg Phe Ala Val Leu Ala Gln Arg Pro Val Asn
1               5                   10                  15 cag gac ggg ctg att ggc gag tgg cct gaa gag ggg ctg atc gcc atg    96
Gln Asp Gly Leu Ile Gly Glu Trp Pro Glu Glu Gly Leu Ile Ala Met
            20                  25                  30 gac agc ccc ttt gac ccg gtc tct tca gta aaa gtg gac aac ggt ctg    144
Asp Ser Pro Phe Asp Pro Val Ser Ser Val Lys Val Asp Asn Gly Leu
        35                  40                  45 atc gtc gaa ctg gac ggc aaa cgc cgg gac cag ttt gac atg atc gac    192
Ile Val Glu Leu Asp Gly Lys Arg Arg Asp Gln Phe Asp Met Ile Asp
    50                  55                  60 cga ttt atc gcc gat tac gcg atc aac gtt gag cgc aca gag cag gca    240
Arg Phe Ile Ala Asp Tyr Ala Ile Asn Val Glu Arg Thr Glu Gln Ala
65                  70                  75                  80 atg cgc ctg gag gcg gtg gaa ata gcc cgt atg ctg gtg gat att cac    288
Met Arg Leu Glu Ala Val Glu Ile Ala Arg Met Leu Val Asp Ile His
                85                  90                  95 gtc agc cgg gag gag atc att gcc atc act acc gcc atc acg ccg gcc    336
Val Ser Arg Glu Glu Ile Ile Ala Ile Thr Thr Ala Ile Thr Pro Ala
            100                 105                 110 aaa gcg gtc gag gtg atg gcg cag atg aac gtg gtg gag atg atg atg    384
Lys Ala Val Glu Val Met Ala Gln Met Asn Val Val Glu Met Met Met
        115                 120                 125 gcg ctg cag aag atg cgt gcc cgc cgg acc ccc tcc aac cag tgc cac    432
Ala Leu Gln Lys Met Arg Ala Arg Arg Thr Pro Ser Asn Gln Cys His
    130                 135                 140
```

-continued

| | |
|---|---|
| gtc acc aat ctc aaa gat aat ccg gtg cag att gcg gct gac gcc gcc<br>Val Thr Asn Leu Lys Asp Asn Pro Val Gln Ile Ala Ala Asp Ala Ala<br>145                  150                  155                  160 | 480 |
| gag gcc ggg atc cgc ggc ttc tca gaa cag gag acc acg gtc ggt atc<br>Glu Ala Gly Ile Arg Gly Phe Ser Glu Gln Glu Thr Thr Val Gly Ile<br>                  165                  170                  175 | 528 |
| gcg cgc tac gcg ccg ttt aac gcc ctg gcg ctg ttg gtc ggt tcg cag<br>Ala Arg Tyr Ala Pro Phe Asn Ala Leu Ala Leu Leu Val Gly Ser Gln<br>                180                  185                  190 | 576 |
| tgc ggc cgc ccc ggc gtg ttg acg cag tgc tcg gtg gaa gag gcc acc<br>Cys Gly Arg Pro Gly Val Leu Thr Gln Cys Ser Val Glu Glu Ala Thr<br>       195                  200                  205 | 624 |
| gag ctg gag ctg ggc atg cgt ggc tta acc agc tac gcc gag acg gtg<br>Glu Leu Glu Leu Gly Met Arg Gly Leu Thr Ser Tyr Ala Glu Thr Val<br>210                  215                  220 | 672 |
| tcg gtc tac ggc acc gaa gcg gta ttt acc gac ggc gat gat acg ccg<br>Ser Val Tyr Gly Thr Glu Ala Val Phe Thr Asp Gly Asp Asp Thr Pro<br>225                  230                  235                  240 | 720 |
| tgg tca aag gcg ttc ctc gcc tcg gcc tac gcc tcc cgc ggg ttg aaa<br>Trp Ser Lys Ala Phe Leu Ala Ser Ala Tyr Ala Ser Arg Gly Leu Lys<br>                     245                  250                  255 | 768 |
| atg cgc tac acc tcc ggc acc gga tcc gaa gcg ctg atg ggc tat tcg<br>Met Arg Tyr Thr Ser Gly Thr Gly Ser Glu Ala Leu Met Gly Tyr Ser<br>                260                  265                  270 | 816 |
| gag agc aag tcg atg ctc tac ctc gaa tcg cgc tgc atc ttc att act<br>Glu Ser Lys Ser Met Leu Tyr Leu Glu Ser Arg Cys Ile Phe Ile Thr<br>       275                  280                  285 | 864 |
| aaa ggc gcc ggg gtt cag gga ctg caa aac ggc gcg gtg agc tgt atc<br>Lys Gly Ala Gly Val Gln Gly Leu Gln Asn Gly Ala Val Ser Cys Ile<br>290                  295                  300 | 912 |
| ggc atg acc ggc gct gtg ccg tcg ggc att cgg gcg gtg ctg gcg gaa<br>Gly Met Thr Gly Ala Val Pro Ser Gly Ile Arg Ala Val Leu Ala Glu<br>305                  310                  315                  320 | 960 |
| aac ctg atc gcc tct atg ctc gac ctc gaa gtg gcg tcc gcc aac gac<br>Asn Leu Ile Ala Ser Met Leu Asp Leu Glu Val Ala Ser Ala Asn Asp<br>                     325                  330                  335 | 1008 |
| cag act ttc tcc cac tcg gat att cgc cgc acc gcg cgc acc ctg atg<br>Gln Thr Phe Ser His Ser Asp Ile Arg Arg Thr Ala Arg Thr Leu Met<br>                340                  345                  350 | 1056 |
| cag atg ctg ccg ggc acc gac ttt att ttc tcc ggc tac agc gcg gtg<br>Gln Met Leu Pro Gly Thr Asp Phe Ile Phe Ser Gly Tyr Ser Ala Val<br>       355                  360                  365 | 1104 |
| ccg aac tac gac aac atg ttc gcc ggc tcg aac ttc gat gcg gaa gat<br>Pro Asn Tyr Asp Asn Met Phe Ala Gly Ser Asn Phe Asp Ala Glu Asp<br>370                  375                  380 | 1152 |
| ttt gat gat tac aac atc ctg cag cgt gac ctg atg gtt gac ggc ggc<br>Phe Asp Asp Tyr Asn Ile Leu Gln Arg Asp Leu Met Val Asp Gly Gly<br>385                  390                  395                  400 | 1200 |
| ctg cgt ccg gtg acc gag gcg gaa acc att gcc att cgc cag aaa gcg<br>Leu Arg Pro Val Thr Glu Ala Glu Thr Ile Ala Ile Arg Gln Lys Ala<br>                     405                  410                  415 | 1248 |
| gcg cgg gcg atc cag gcg gtt ttc cgc gag ctg ggc ctg cca cca atc<br>Ala Arg Ala Ile Gln Ala Val Phe Arg Glu Leu Gly Leu Pro Pro Ile<br>                420                  425                  430 | 1296 |
| gcc gac gag gag gtg gag gcc gcc acc tac gcg cac ggc agc aac gag<br>Ala Asp Glu Glu Val Glu Ala Ala Thr Tyr Ala His Gly Ser Asn Glu<br>       435                  440                  445 | 1344 |
| atg ccg ccg cgt aac gtg gtg gag gat ctg agt gcg gtg gaa gag atg<br>Met Pro Pro Arg Asn Val Val Glu Asp Leu Ser Ala Val Glu Glu Met<br>450                  455                  460 | 1392 |

```
atg aag cgc aac atc acc ggc ctc gat att gtc ggc gcg ctg agc cgc      1440
Met Lys Arg Asn Ile Thr Gly Leu Asp Ile Val Gly Ala Leu Ser Arg
465                 470                 475                 480 agc ggc ttt gag gat atc gcc agc aat att ctc aat atg ctg cgc cag      1488
Ser Gly Phe Glu Asp Ile Ala Ser Asn Ile Leu Asn Met Leu Arg Gln
                485                 490                 495 cgg gtc acc ggc gat tac ctg cag acc tcg gcc att ctc gat cgg cag      1536
Arg Val Thr Gly Asp Tyr Leu Gln Thr Ser Ala Ile Leu Asp Arg Gln
            500                 505                 510 ttc gag gtg gtg agt gcg gtc aac gac atc aat gac tat cag ggg ccg      1584
Phe Glu Val Val Ser Ala Val Asn Asp Ile Asn Asp Tyr Gln Gly Pro
        515                 520                 525 ggc acc ggc tat cgc atc tct gcc gaa cgc tgg gcg gag atc aaa aat      1632
Gly Thr Gly Tyr Arg Ile Ser Ala Glu Arg Trp Ala Glu Ile Lys Asn
    530                 535                 540 att ccg ggc gtg gtt cag ccc gac acc att gaa taa                      1668
Ile Pro Gly Val Val Gln Pro Asp Thr Ile Glu
545                 550                 555

<210> SEQ ID NO 10
<211> LENGTH: 555
<212> TYPE: PRT
<213> ORGANISM: Klebsiella pneumoniae

<400> SEQUENCE: 10

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255
```

```
Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc    48
Val Gln Gln Thr Thr Gln Ile Gln Pro Ser Phe Thr Leu Lys Thr Arg
1               5                   10                  15 gag ggc ggg gta gct tct gcc gat gaa cgc gcc gat gaa gtg gtg atc    96
Glu Gly Gly Val Ala Ser Ala Asp Glu Arg Ala Asp Glu Val Val Ile
            20                  25                  30 ggc gtc ggc cct gcc ttc gat aaa cac cag cat cac act ctg atc gat   144
Gly Val Gly Pro Ala Phe Asp Lys His Gln His His Thr Leu Ile Asp
        35                  40                  45
```

```
atg ccc cat ggc gcg atc ctc aaa gag ctg att gcg ggg gtg gaa gaa      192
Met Pro His Gly Ala Ile Leu Lys Glu Leu Ile Ala Gly Val Glu Glu
 50                  55                  60 gag ggg ctt cac gcc cgg gtg gtg cgc att ctg cgc acg tcc gac gtc      240
Glu Gly Leu His Ala Arg Val Val Arg Ile Leu Arg Thr Ser Asp Val
 65                  70                  75                  80 tcc ttt atg gcc tgg gat gcg gcc aac ctg agc ggc tcg ggg atc ggc      288
Ser Phe Met Ala Trp Asp Ala Ala Asn Leu Ser Gly Ser Gly Ile Gly
                 85                  90                  95 atc ggt atc cag tcg aag ggg acc acg gtc atc cat cag cgc gat ctg      336
Ile Gly Ile Gln Ser Lys Gly Thr Thr Val Ile His Gln Arg Asp Leu
            100                 105                 110 ctg ccg ctc agc aac ctg gag ctg ttc tcc cag gcg ccg ctg ctg acg      384
Leu Pro Leu Ser Asn Leu Glu Leu Phe Ser Gln Ala Pro Leu Leu Thr
        115                 120                 125 ctg gag acc tac cgg cag att ggc aaa aac gct gcg cgc tat gcg cgc      432
Leu Glu Thr Tyr Arg Gln Ile Gly Lys Asn Ala Ala Arg Tyr Ala Arg
130                 135                 140 aaa gag tca cct tcg ccg gtg ccg gtg gtg aac gat cag atg gtg cgg      480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa      528
Pro Lys Phe Met Ala Lys Ala Ala Leu Phe His Ile Lys Glu Thr Lys
                165                 170                 175 cat gtg gtg cag gac gcc gag ccc gtc acc ctg cac atc gac tta gta      576
His Val Val Gln Asp Ala Glu Pro Val Thr Leu His Ile Asp Leu Val
            180                 185                 190 agg gag tga                                                            585
Arg Glu <210> SEQ ID NO 12
<211> LENGTH: 194
<212> TYPE: PRT
<213> ORGANISM: Klebsiella pneumoniae

<400> SEQUENCE: 12

Val Gln Gln Thr Thr Gln Ile Gln Pro Ser Phe Thr Leu Lys Thr Arg
 1               5                  10                  15

Glu Gly Gly Val Ala Ser Ala Asp Glu Arg Ala Asp Glu Val Val Ile
                20                  25                  30

Gly Val Gly Pro Ala Phe Asp Lys His Gln His Thr Leu Ile Asp
            35                  40                  45

Met Pro His Gly Ala Ile Leu Lys Glu Leu Ile Ala Gly Val Glu Glu
 50                  55                  60

Glu Gly Leu His Ala Arg Val Val Arg Ile Leu Arg Thr Ser Asp Val
 65                  70                  75                  80

Ser Phe Met Ala Trp Asp Ala Ala Asn Leu Ser Gly Ser Gly Ile Gly
                 85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175
```

```
His Val Val Gln Asp Ala Glu Pro Val Thr Leu His Ile Asp Leu Val
            180                 185                 190

Arg Glu
```

<210> SEQ ID NO 13
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

<400> SEQUENCE: 13

```
atg agc gag aaa acc atg cgc gtg cag gat tat ccg tta gcc acc cgc      48
Met Ser Glu Lys Thr Met Arg Val Gln Asp Tyr Pro Leu Ala Thr Arg
1               5                   10                  15 tgc ccg gag cat atc ctg acg cct acc ggc aaa cca ttg acc gat att      96
Cys Pro Glu His Ile Leu Thr Pro Thr Gly Lys Pro Leu Thr Asp Ile
                20                  25                  30 acc ctc gag aag gtg ctc tct ggc gag gtg ggc ccg cag gat gtg cgg     144
Thr Leu Glu Lys Val Leu Ser Gly Glu Val Gly Pro Gln Asp Val Arg
            35                  40                  45 atc tcc cgc cag acc ctt gag tac cag gcg cag att gcc gag cag atg     192
Ile Ser Arg Gln Thr Leu Glu Tyr Gln Ala Gln Ile Ala Glu Gln Met
        50                  55                  60 cag cgc cat gcg gtg gcg cgc aat ttc cgc cgc gcg gcg gag ctt atc     240
Gln Arg His Ala Val Ala Arg Asn Phe Arg Arg Ala Ala Glu Leu Ile
65                  70                  75                  80 gcc att cct gac gag cgc att ctg gct atc tat aac gcg ctg cgc ccg     288
Ala Ile Pro Asp Glu Arg Ile Leu Ala Ile Tyr Asn Ala Leu Arg Pro
                85                  90                  95 ttc cgc tcc tcg cag gcg gag ctg ctg gcg atc gcc gac gag ctg gag     336
Phe Arg Ser Ser Gln Ala Glu Leu Leu Ala Ile Ala Asp Glu Leu Glu
                100                 105                 110 cac acc tgg cat gcg aca gtg aat gcc gcc ttt gtc cgg gag tcg gcg     384
His Thr Trp His Ala Thr Val Asn Ala Ala Phe Val Arg Glu Ser Ala
            115                 120                 125 gaa gtg tat cag cag cgg cat aag ctg cgt aaa gga agc taa             426
Glu Val Tyr Gln Gln Arg His Lys Leu Arg Lys Gly Ser
        130                 135                 140
```

<210> SEQ ID NO 14
<211> LENGTH: 141
<212> TYPE: PRT
<213> ORGANISM: Klebsiella pneumoniae

<400> SEQUENCE: 14

```
Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
        50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
                100                 105                 110
```

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
130                 135                 140

<210> SEQ ID NO 15
<211> LENGTH: 1539
<212> TYPE: DNA
<213> ORGANISM: Escherichia coli
<220> FEATURE:
<221> NAME/KEY: CDS
<222> LOCATION: (1)..(1539)

<400> SEQUENCE: 15

```
atg acc aat aat ccc cct tca gca cag att aag ccc ggc gag tat ggt      48
Met Thr Asn Asn Pro Pro Ser Ala Gln Ile Lys Pro Gly Glu Tyr Gly
  1               5                  10                  15 ttc ccc ctc aag tta aaa gcc cgc tat gac aac ttt att ggc ggc gaa      96
Phe Pro Leu Lys Leu Lys Ala Arg Tyr Asp Asn Phe Ile Gly Gly Glu
             20                  25                  30 tgg gta gcc cct gcc gac ggc gag tat tac cag aat ctg acg ccg gtg     144
Trp Val Ala Pro Ala Asp Gly Glu Tyr Tyr Gln Asn Leu Thr Pro Val
         35                  40                  45 acc ggg cag ctg ctg tgc gaa gtg gcg tct tcg ggc aaa cga gac atc     192
Thr Gly Gln Leu Leu Cys Glu Val Ala Ser Ser Gly Lys Arg Asp Ile
 50                  55                  60 gat ctg gcg ctg gat gct gcg cac aaa gtg aaa gat aaa tgg gcg cac     240
Asp Leu Ala Leu Asp Ala Ala His Lys Val Lys Asp Lys Trp Ala His
 65                  70                  75                  80 acc tcg gtg cag gat cgt gcg gcg att ctg ttt aag att gcc gat cga     288
Thr Ser Val Gln Asp Arg Ala Ala Ile Leu Phe Lys Ile Ala Asp Arg
                 85                  90                  95 atg gaa caa aac ctc gag ctg tta gcg aca gct gaa acc tgg gat aac     336
Met Glu Gln Asn Leu Glu Leu Leu Ala Thr Ala Glu Thr Trp Asp Asn
            100                 105                 110 ggc aaa ccc att cgc gaa acc agt gct gcg gat gta ccg ctg gcg att     384
Gly Lys Pro Ile Arg Glu Thr Ser Ala Ala Asp Val Pro Leu Ala Ile
        115                 120                 125 gac cat ttc cgc tat ttc gcc tcg tgt att cgg gcg cag gaa ggt ggg     432
Asp His Phe Arg Tyr Phe Ala Ser Cys Ile Arg Ala Gln Glu Gly Gly
    130                 135                 140 atc agt gaa gtt gat agc gaa acc gtg gcc tat cat ttc cat gaa ccg     480
Ile Ser Glu Val Asp Ser Glu Thr Val Ala Tyr His Phe His Glu Pro
145                 150                 155                 160 tta ggc gtg gtg ggg cag att atc ccg tgg aac ttc ccg ctg ctg atg     528
Leu Gly Val Val Gly Gln Ile Ile Pro Trp Asn Phe Pro Leu Leu Met
                165                 170                 175 gcg agc tgg aaa atg gct ccc gcg ctg gcg gcg ggc aac tgt gtg gtg     576
Ala Ser Trp Lys Met Ala Pro Ala Leu Ala Ala Gly Asn Cys Val Val
            180                 185                 190 ctg aaa ccc gca cgt ctt acc ccg ctt tct gta ctg cta atg gaa         624
Leu Lys Pro Ala Arg Leu Thr Pro Leu Ser Val Leu Leu Met Glu
        195                 200                 205 att gtc ggt gat tta ctg ccg ccg ggc gtg gtg aac gtg gtc aat ggc     672
Ile Val Gly Asp Leu Leu Pro Pro Gly Val Val Asn Val Val Asn Gly
    210                 215                 220 gca ggt ggg gta att ggc gaa tat ctg gcg acc tcg aaa cgc atc gcc     720
Ala Gly Gly Val Ile Gly Glu Tyr Leu Ala Thr Ser Lys Arg Ile Ala
225                 230                 235                 240 aaa gtg gcg ttt acc ggc tca acg gaa gtg ggc caa caa att atg caa     768
Lys Val Ala Phe Thr Gly Ser Thr Glu Val Gly Gln Gln Ile Met Gln
```

```
                      245                 250                 255
tac gca acg caa aac att att ccg gtg acg ctg gag ttg ggc ggt aag    816
Tyr Ala Thr Gln Asn Ile Ile Pro Val Thr Leu Glu Leu Gly Gly Lys
            260                 265                 270 tcg cca aat atc ttc ttt gct gat gtg atg gat gaa gaa gat gcc ttt    864
Ser Pro Asn Ile Phe Phe Ala Asp Val Met Asp Glu Glu Asp Ala Phe
        275                 280                 285 ttc gat aaa gcg ctg gaa ggc ttt gca ctg ttt gcc ttt aac cag ggc    912
Phe Asp Lys Ala Leu Glu Gly Phe Ala Leu Phe Ala Phe Asn Gln Gly
    290                 295                 300 gaa gtt tgc acc tgt ccg agt cgt gct tta gtg cag gaa tct atc tac    960
Glu Val Cys Thr Cys Pro Ser Arg Ala Leu Val Gln Glu Ser Ile Tyr
305                 310                 315                 320 gaa cgc ttt atg gaa cgc gcc atc cgc cgt gtc gaa agc att cgt agc    1008
Glu Arg Phe Met Glu Arg Ala Ile Arg Arg Val Glu Ser Ile Arg Ser
                325                 330                 335 ggt aac ccg ctc gac agc gtg acg caa atg ggc gcg cag gtt tct cac    1056
Gly Asn Pro Leu Asp Ser Val Thr Gln Met Gly Ala Gln Val Ser His
            340                 345                 350 ggg caa ctg gaa acc atc ctc aac tac att gat atc ggt aaa aaa gag    1104
Gly Gln Leu Glu Thr Ile Leu Asn Tyr Ile Asp Ile Gly Lys Lys Glu
        355                 360                 365 ggc gct gac gtg ctc aca ggc ggg cgg cgc aag ctg ctg gaa ggt gaa    1152
Gly Ala Asp Val Leu Thr Gly Gly Arg Arg Lys Leu Leu Glu Gly Glu
    370                 375                 380 ctg aaa gac ggc tac tac ctc gaa ccg acg att ctg ttt ggt cag aac    1200
Leu Lys Asp Gly Tyr Tyr Leu Glu Pro Thr Ile Leu Phe Gly Gln Asn
385                 390                 395                 400 aat atg cgg gtg ttc cag gag gag att ttt ggc ccg gtg ctg gcg gtg    1248
Asn Met Arg Val Phe Gln Glu Glu Ile Phe Gly Pro Val Leu Ala Val
                405                 410                 415 acc acc ttc aaa acg atg gaa gaa gcg ctg gag ctg gcg aac gat acg    1296
Thr Thr Phe Lys Thr Met Glu Glu Ala Leu Glu Leu Ala Asn Asp Thr
            420                 425                 430 caa tat ggc ctg ggc gcg ggc gtc tgg agc cgc aac ggt aat ctg gcc    1344
Gln Tyr Gly Leu Gly Ala Gly Val Trp Ser Arg Asn Gly Asn Leu Ala
        435                 440                 445 tat aag atg ggg cgc ggc ata cag gct ggg cgc gtg tgg acc aac tgt    1392
Tyr Lys Met Gly Arg Gly Ile Gln Ala Gly Arg Val Trp Thr Asn Cys
    450                 455                 460 tat cac gct tac ccg gca cat gcg gcg ttt ggt ggc tac aaa caa tca    1440
Tyr His Ala Tyr Pro Ala His Ala Ala Phe Gly Gly Tyr Lys Gln Ser
465                 470                 475                 480 ggt atc ggt cgc gaa acc cac aag atg atg ctg gag cat tac cag caa    1488
Gly Ile Gly Arg Glu Thr His Lys Met Met Leu Glu His Tyr Gln Gln
                485                 490                 495 acc aag tgc ctg ctg gtg agc tac tcg gat aaa ccg ttg ggg ctg ttc    1536
Thr Lys Cys Leu Leu Val Ser Tyr Ser Asp Lys Pro Leu Gly Leu Phe
            500                 505                 510 tga                                                                1539

<210> SEQ ID NO 16
<211> LENGTH: 512
<212> TYPE: PRT
<213> ORGANISM: Escherichia coli

<400> SEQUENCE: 16

Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
```

-continued

```
                20                  25                  30
Trp Val Ala Pro Ala Asp Gly Glu Tyr Tyr Gln Asn Leu Thr Pro Val
            35                  40                  45
Thr Gly Gln Leu Leu Cys Glu Val Ala Ser Ser Gly Lys Arg Asp Ile
        50                  55                  60
Asp Leu Ala Leu Asp Ala Ala His Lys Val Lys Asp Lys Trp Ala His
65                  70                  75                  80
Thr Ser Val Gln Asp Arg Ala Ala Ile Leu Phe Lys Ile Ala Asp Arg
                85                  90                  95
Met Glu Gln Asn Leu Glu Leu Leu Ala Thr Ala Glu Thr Trp Asp Asn
            100                 105                 110
Gly Lys Pro Ile Arg Glu Thr Ser Ala Ala Asp Val Pro Leu Ala Ile
        115                 120                 125
Asp His Phe Arg Tyr Phe Ala Ser Cys Ile Arg Ala Gln Glu Gly Gly
    130                 135                 140
Ile Ser Glu Val Asp Ser Glu Thr Val Ala Tyr His Phe His Glu Pro
145                 150                 155                 160
Leu Gly Val Val Gly Gln Ile Ile Pro Trp Asn Phe Pro Leu Leu Met
                165                 170                 175
Ala Ser Trp Lys Met Ala Pro Ala Leu Ala Ala Gly Asn Cys Val Val
            180                 185                 190
Leu Lys Pro Ala Arg Leu Thr Pro Leu Ser Val Leu Leu Met Glu
        195                 200                 205
Ile Val Gly Asp Leu Leu Pro Pro Gly Val Val Asn Val Val Asn Gly
    210                 215                 220
Ala Gly Gly Val Ile Gly Glu Tyr Leu Ala Thr Ser Lys Arg Ile Ala
225                 230                 235                 240
Lys Val Ala Phe Thr Gly Ser Thr Glu Val Gly Gln Gln Ile Met Gln
                245                 250                 255
Tyr Ala Thr Gln Asn Ile Ile Pro Val Thr Leu Glu Leu Gly Gly Lys
            260                 265                 270
Ser Pro Asn Ile Phe Phe Ala Asp Val Met Asp Glu Glu Asp Ala Phe
        275                 280                 285
Phe Asp Lys Ala Leu Glu Gly Phe Ala Leu Phe Ala Phe Asn Gln Gly
    290                 295                 300
Glu Val Cys Thr Cys Pro Ser Arg Ala Leu Val Gln Glu Ser Ile Tyr
305                 310                 315                 320
Glu Arg Phe Met Glu Arg Ala Ile Arg Arg Val Glu Ser Ile Arg Ser
                325                 330                 335
Gly Asn Pro Leu Asp Ser Val Thr Gln Met Gly Ala Gln Val Ser His
            340                 345                 350
Gly Gln Leu Glu Thr Ile Leu Asn Tyr Ile Asp Ile Gly Lys Lys Glu
        355                 360                 365
Gly Ala Asp Val Leu Thr Gly Gly Arg Arg Lys Leu Leu Glu Gly Glu
    370                 375                 380
Leu Lys Asp Gly Tyr Tyr Leu Glu Pro Thr Ile Leu Phe Gly Gln Asn
385                 390                 395                 400
Asn Met Arg Val Phe Gln Glu Glu Ile Phe Gly Pro Val Leu Ala Val
                405                 410                 415
Thr Thr Phe Lys Thr Met Glu Glu Ala Leu Glu Leu Ala Asn Asp Thr
            420                 425                 430
Gln Tyr Gly Leu Gly Ala Gly Val Trp Ser Arg Asn Gly Asn Leu Ala
        435                 440                 445
```

```
Tyr Lys Met Gly Arg Gly Ile Gln Ala Gly Arg Val Trp Thr Asn Cys
450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
            500                 505                 510

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17
```

| | | | | | | | | | | | | | | | | |
|---|---|---|---|---|---|---|---|---|---|---|---|---|---|---|---|---|
| atg | tca | gta | ccc | gtt | caa | cat | cct | atg | tat | atc | gat | gga | cag | ttt | gtt | 48 |
| Met | Ser | Val | Pro | Val | Gln | His | Pro | Met | Tyr | Ile | Asp | Gly | Gln | Phe | Val | |
| 1 | | | | 5 | | | | | 10 | | | | | 15 | | |
| acc | tgg | cgt | gga | gac | gca | tgg | att | gat | gtg | gta | aac | cct | gct | aca | gag | 96 |
| Thr | Trp | Arg | Gly | Asp | Ala | Trp | Ile | Asp | Val | Val | Asn | Pro | Ala | Thr | Glu | |
| | | | 20 | | | | | 25 | | | | | 30 | | | |
| gct | gtc | att | tcc | cgc | ata | ccc | gat | ggt | cag | gcc | gag | gat | gcc | cgt | aag | 144 |
| Ala | Val | Ile | Ser | Arg | Ile | Pro | Asp | Gly | Gln | Ala | Glu | Asp | Ala | Arg | Lys | |
| | | 35 | | | | | 40 | | | | | 45 | | | | |
| gca | atc | gat | gca | gca | gaa | cgt | gca | caa | cca | gaa | tgg | gaa | gcg | ttg | cct | 192 |
| Ala | Ile | Asp | Ala | Ala | Glu | Arg | Ala | Gln | Pro | Glu | Trp | Glu | Ala | Leu | Pro | |
| | 50 | | | | | 55 | | | | | 60 | | | | | |
| gct | att | gaa | cgc | gcc | agt | tgg | ttg | cgc | aaa | atc | tcc | gcc | ggg | atc | cgc | 240 |
| Ala | Ile | Glu | Arg | Ala | Ser | Trp | Leu | Arg | Lys | Ile | Ser | Ala | Gly | Ile | Arg | |
| 65 | | | | | 70 | | | | | 75 | | | | | 80 | |
| gaa | cgc | gcc | agt | gaa | atc | agt | gcg | ctg | att | gtt | gaa | gaa | ggg | ggc | aag | 288 |
| Glu | Arg | Ala | Ser | Glu | Ile | Ser | Ala | Leu | Ile | Val | Glu | Glu | Gly | Gly | Lys | |
| | | | | 85 | | | | | 90 | | | | | 95 | | |
| atc | cag | cag | ctg | gct | gaa | gtc | gaa | gtg | gct | ttt | act | gcc | gac | tat | atc | 336 |
| Ile | Gln | Gln | Leu | Ala | Glu | Val | Glu | Val | Ala | Phe | Thr | Ala | Asp | Tyr | Ile | |
| | | | 100 | | | | | 105 | | | | | 110 | | | |
| gat | tac | atg | gcg | gag | tgg | gca | cgg | cgt | tac | gag | ggc | gag | att | att | caa | 384 |
| Asp | Tyr | Met | Ala | Glu | Trp | Ala | Arg | Arg | Tyr | Glu | Gly | Glu | Ile | Ile | Gln | |
| | | 115 | | | | | 120 | | | | | 125 | | | | |
| agc | gat | cgt | cca | gga | gaa | aat | att | ctt | ttg | ttt | aaa | cgt | gcg | ctt | ggt | 432 |
| Ser | Asp | Arg | Pro | Gly | Glu | Asn | Ile | Leu | Leu | Phe | Lys | Arg | Ala | Leu | Gly | |
| | 130 | | | | | 135 | | | | | 140 | | | | | |
| gtg | act | acc | ggc | att | ctg | ccg | tgg | aac | ttc | ccg | ttc | ttc | ctc | att | gcc | 480 |
| Val | Thr | Thr | Gly | Ile | Leu | Pro | Trp | Asn | Phe | Pro | Phe | Phe | Leu | Ile | Ala | |
| 145 | | | | | 150 | | | | | 155 | | | | | 160 | |
| cgc | aaa | atg | gct | ccc | gct | ctt | ttg | acc | ggt | aat | acc | atc | gtc | att | aaa | 528 |
| Arg | Lys | Met | Ala | Pro | Ala | Leu | Leu | Thr | Gly | Asn | Thr | Ile | Val | Ile | Lys | |
| | | | | 165 | | | | | 170 | | | | | 175 | | |
| cct | agt | gaa | ttt | acg | cca | aac | aat | gcg | att | gca | ttc | gcc | aaa | atc | gtc | 576 |
| Pro | Ser | Glu | Phe | Thr | Pro | Asn | Asn | Ala | Ile | Ala | Phe | Ala | Lys | Ile | Val | |
| | | | 180 | | | | | 185 | | | | | 190 | | | |
| gat | gaa | ata | ggc | ctt | ccg | cgc | ggc | gtg | ttt | aac | ctt | gta | ctg | ggg | cgt | 624 |
| Asp | Glu | Ile | Gly | Leu | Pro | Arg | Gly | Val | Phe | Asn | Leu | Val | Leu | Gly | Arg | |
| | | 195 | | | | | 200 | | | | | 205 | | | | |
| ggt | gaa | acc | gtt | ggg | caa | gaa | ctg | gcg | ggt | aac | cca | aag | gtc | gca | atg | 672 |
| Gly | Glu | Thr | Val | Gly | Gln | Glu | Leu | Ala | Gly | Asn | Pro | Lys | Val | Ala | Met | |
| | 210 | | | | | 215 | | | | | 220 | | | | | |
| gtc | agt | atg | aca | ggc | agc | gtc | tct | gca | ggt | gag | aag | atc | atg | gcg | act | 720 |

```
Val Ser Met Thr Gly Ser Val Ser Ala Gly Glu Lys Ile Met Ala Thr
225                 230                 235                 240 gcg gcg aaa aac atc acc aaa gtg tgt ctg gaa ttg ggg ggt aaa gca      768
Ala Ala Lys Asn Ile Thr Lys Val Cys Leu Glu Leu Gly Gly Lys Ala
                245                 250                 255 cca gct atc gta atg gac gat gcc gat ctt gaa ctg gca gtc aaa gcc      816
Pro Ala Ile Val Met Asp Asp Ala Asp Leu Glu Leu Ala Val Lys Ala
                260                 265                 270 atc gtt gat tca cgc gtc att aat agt ggg caa gtg tgt aac tgt gca      864
Ile Val Asp Ser Arg Val Ile Asn Ser Gly Gln Val Cys Asn Cys Ala
                275                 280                 285 gaa cgt gtt tat gta cag aaa ggc att tat gat cag ttc gtc aat cgg      912
Glu Arg Val Tyr Val Gln Lys Gly Ile Tyr Asp Gln Phe Val Asn Arg
        290                 295                 300 ctg ggt gaa gcg atg cag gcg gtt caa ttt ggt aac ccc gct gaa cgc      960
Leu Gly Glu Ala Met Gln Ala Val Gln Phe Gly Asn Pro Ala Glu Arg
305                 310                 315                 320 aac gac att gcg atg ggg ccg ttg att aac gcc gcg gcg ctg gaa agg     1008
Asn Asp Ile Ala Met Gly Pro Leu Ile Asn Ala Ala Ala Leu Glu Arg
                325                 330                 335 gtc gag caa aaa gtg gcg cgc gca gta gaa gaa ggg gcg aga gtg gcg     1056
Val Glu Gln Lys Val Ala Arg Ala Val Glu Glu Gly Ala Arg Val Ala
                340                 345                 350 ttc ggt ggc aaa gcg gta gag ggg aaa gga tat tat tat ccg ccg aca     1104
Phe Gly Gly Lys Ala Val Glu Gly Lys Gly Tyr Tyr Tyr Pro Pro Thr
                355                 360                 365 ttg ctg ctg gat gtt cgc cag gaa atg tcg att atg cat gag gaa acc     1152
Leu Leu Leu Asp Val Arg Gln Glu Met Ser Ile Met His Glu Glu Thr
370                 375                 380 ttt ggc ccg gtg ctg cca gtt gtc gca ttt gac acg ctg gaa gat gct     1200
Phe Gly Pro Val Leu Pro Val Val Ala Phe Asp Thr Leu Glu Asp Ala
385                 390                 395                 400 atc tca atg gct aat gac agt gat tac ggc ctg acc tca tca atc tat     1248
Ile Ser Met Ala Asn Asp Ser Asp Tyr Gly Leu Thr Ser Ser Ile Tyr
                405                 410                 415 acc caa aat ctg aac gtc gcg atg aaa gcc att aaa ggg ctg aag ttt     1296
Thr Gln Asn Leu Asn Val Ala Met Lys Ala Ile Lys Gly Leu Lys Phe
                420                 425                 430 ggt gaa act tac atc aac cgt gaa aac ttc gaa gct atg caa ggc ttc     1344
Gly Glu Thr Tyr Ile Asn Arg Glu Asn Phe Glu Ala Met Gln Gly Phe
                435                 440                 445 cac gcc gga tgg cgt aaa tcc ggt att ggc ggc gca gat ggt aaa cat     1392
His Ala Gly Trp Arg Lys Ser Gly Ile Gly Gly Ala Asp Gly Lys His
        450                 455                 460 ggc ttg cat gaa tat ctg cag acc cag gtg gtt tat tta cag tct taa     1440
Gly Leu His Glu Tyr Leu Gln Thr Gln Val Val Tyr Leu Gln Ser
465                 470                 475

<210> SEQ ID NO 18
<211> LENGTH: 479
<212> TYPE: PRT
<213> ORGANISM: Escherichia coli

<400> SEQUENCE: 18

Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45
```

```
Ala Ile Asp Ala Ala Glu Arg Ala Gln Pro Glu Trp Glu Ala Leu Pro
 50                  55                  60

Ala Ile Glu Arg Ala Ser Trp Leu Arg Lys Ile Ser Ala Gly Ile Arg
 65                  70                  75                  80

Glu Arg Ala Ser Glu Ile Ser Ala Leu Ile Val Glu Glu Gly Gly Lys
                 85                  90                  95

Ile Gln Gln Leu Ala Glu Val Glu Val Ala Phe Thr Ala Asp Tyr Ile
             100                 105                 110

Asp Tyr Met Ala Glu Trp Ala Arg Arg Tyr Glu Gly Glu Ile Ile Gln
         115                 120                 125

Ser Asp Arg Pro Gly Glu Asn Ile Leu Leu Phe Lys Arg Ala Leu Gly
     130                 135                 140

Val Thr Thr Gly Ile Leu Pro Trp Asn Phe Pro Phe Leu Ile Ala
145                 150                 155                 160

Arg Lys Met Ala Pro Ala Leu Leu Thr Gly Asn Thr Ile Val Ile Lys
             165                 170                 175

Pro Ser Glu Phe Thr Pro Asn Asn Ala Ile Ala Phe Ala Lys Ile Val
             180                 185                 190

Asp Glu Ile Gly Leu Pro Arg Gly Val Phe Asn Leu Val Leu Gly Arg
         195                 200                 205

Gly Glu Thr Val Gly Gln Glu Leu Ala Gly Asn Pro Lys Val Ala Met
     210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
             245                 250                 255

Pro Ala Ile Val Met Asp Asp Ala Asp Leu Glu Leu Ala Val Lys Ala
             260                 265                 270

Ile Val Asp Ser Arg Val Ile Asn Ser Gly Gln Val Cys Asn Cys Ala
         275                 280                 285

Glu Arg Val Tyr Val Gln Lys Gly Ile Tyr Asp Gln Phe Val Asn Arg
     290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
             325                 330                 335

Val Glu Gln Lys Val Ala Arg Ala Val Glu Glu Gly Ala Arg Val Ala
             340                 345                 350

Phe Gly Gly Lys Ala Val Glu Gly Lys Gly Tyr Tyr Tyr Pro Pro Thr
         355                 360                 365

Leu Leu Leu Asp Val Arg Gln Glu Met Ser Ile Met His Glu Glu Thr
     370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
             405                 410                 415

Thr Gln Asn Leu Asn Val Ala Met Lys Ala Ile Lys Gly Leu Lys Phe
         420                 425                 430

Gly Glu Thr Tyr Ile Asn Arg Glu Asn Phe Glu Ala Met Gln Gly Phe
     435                 440                 445

His Ala Gly Trp Arg Lys Ser Gly Ile Gly Gly Ala Asp Gly Lys His
 450                 455                 460

Gly Leu His Glu Tyr Leu Gln Thr Gln Val Val Tyr Leu Gln Ser
465                 470                 475
```

<210> SEQ ID NO 19
<211> LENGTH: 1488
<212> TYPE: DNA
<213> ORGANISM: Escherichia coli
<220> FEATURE:
<221> NAME/KEY: CDS
<222> LOCATION: (1)..(1488)

<400> SEQUENCE: 19

| atg | aat | ttt | cat | cat | ctg | gct | tac | tgg | cag | gat | aaa | gcg | tta | agt | ctc | 48 |
|---|---|---|---|---|---|---|---|---|---|---|---|---|---|---|---|---|
| Met | Asn | Phe | His | His | Leu | Ala | Tyr | Trp | Gln | Asp | Lys | Ala | Leu | Ser | Leu | |
| 1 | | | | 5 | | | | | 10 | | | | | 15 | | |

| gcc | att | gaa | aac | cgc | tta | ttt | att | aac | ggt | gaa | tat | act | gct | gcg | gcg | 96 |
|---|---|---|---|---|---|---|---|---|---|---|---|---|---|---|---|---|
| Ala | Ile | Glu | Asn | Arg | Leu | Phe | Ile | Asn | Gly | Glu | Tyr | Thr | Ala | Ala | Ala | |
| | | | 20 | | | | | 25 | | | | | 30 | | | |

| gaa | aat | gaa | acc | ttt | gaa | acc | gtt | gat | ccg | gtc | acc | cag | gca | ccg | ctg | 144 |
|---|---|---|---|---|---|---|---|---|---|---|---|---|---|---|---|---|
| Glu | Asn | Glu | Thr | Phe | Glu | Thr | Val | Asp | Pro | Val | Thr | Gln | Ala | Pro | Leu | |
| | | 35 | | | | | 40 | | | | | 45 | | | | |

| gcg | aaa | att | gcc | cgc | ggc | aag | agc | gtc | gat | atc | gac | cgt | gcg | atg | agc | 192 |
|---|---|---|---|---|---|---|---|---|---|---|---|---|---|---|---|---|
| Ala | Lys | Ile | Ala | Arg | Gly | Lys | Ser | Val | Asp | Ile | Asp | Arg | Ala | Met | Ser | |
| 50 | | | | | 55 | | | | | 60 | | | | | | |

| gca | gca | cgc | ggc | gta | ttt | gaa | cgc | ggc | gac | tgg | tca | ctc | tct | tct | ccg | 240 |
|---|---|---|---|---|---|---|---|---|---|---|---|---|---|---|---|---|
| Ala | Ala | Arg | Gly | Val | Phe | Glu | Arg | Gly | Asp | Trp | Ser | Leu | Ser | Ser | Pro | |
| 65 | | | | 70 | | | | | 75 | | | | | 80 | | |

| gct | aaa | cgt | aaa | gcg | gta | ctg | aat | aaa | ctc | gcc | gat | tta | atg | gaa | gcc | 288 |
|---|---|---|---|---|---|---|---|---|---|---|---|---|---|---|---|---|
| Ala | Lys | Arg | Lys | Ala | Val | Leu | Asn | Lys | Leu | Ala | Asp | Leu | Met | Glu | Ala | |
| | | | | 85 | | | | | 90 | | | | | 95 | | |

| cac | gcc | gaa | gag | ctg | gca | ctg | ctg | gaa | act | ctc | gac | acc | ggc | aaa | ccg | 336 |
|---|---|---|---|---|---|---|---|---|---|---|---|---|---|---|---|---|
| His | Ala | Glu | Glu | Leu | Ala | Leu | Leu | Glu | Thr | Leu | Asp | Thr | Gly | Lys | Pro | |
| | | | 100 | | | | | 105 | | | | | 110 | | | |

| att | cgt | cac | agt | ctg | cgt | gat | gat | att | ccc | ggc | gcg | gcg | cgc | gcc | att | 384 |
|---|---|---|---|---|---|---|---|---|---|---|---|---|---|---|---|---|
| Ile | Arg | His | Ser | Leu | Arg | Asp | Asp | Ile | Pro | Gly | Ala | Ala | Arg | Ala | Ile | |
| | | 115 | | | | | 120 | | | | | 125 | | | | |

| cgc | tgg | tac | gcc | gaa | gcg | atc | gac | aaa | gtg | tat | ggc | gaa | gtg | gcg | acc | 432 |
|---|---|---|---|---|---|---|---|---|---|---|---|---|---|---|---|---|
| Arg | Trp | Tyr | Ala | Glu | Ala | Ile | Asp | Lys | Val | Tyr | Gly | Glu | Val | Ala | Thr | |
| 130 | | | | | 135 | | | | | 140 | | | | | | |

| acc | agt | agc | cat | gag | ctg | gcg | atg | atc | gtg | cgt | gaa | ccg | gtc | ggc | gtg | 480 |
|---|---|---|---|---|---|---|---|---|---|---|---|---|---|---|---|---|
| Thr | Ser | Ser | His | Glu | Leu | Ala | Met | Ile | Val | Arg | Glu | Pro | Val | Gly | Val | |
| 145 | | | | 150 | | | | | 155 | | | | | 160 | | |

| att | gcc | gcc | atc | gtg | ccg | tgg | aac | ttc | ccg | ctg | ttg | ctg | act | tgc | tgg | 528 |
|---|---|---|---|---|---|---|---|---|---|---|---|---|---|---|---|---|
| Ile | Ala | Ala | Ile | Val | Pro | Trp | Asn | Phe | Pro | Leu | Leu | Leu | Thr | Cys | Trp | |
| | | | | 165 | | | | | 170 | | | | | 175 | | |

| aaa | ctc | ggc | ccg | gcg | ctg | gcg | gcg | gga | aac | agc | gtg | att | cta | aaa | ccg | 576 |
|---|---|---|---|---|---|---|---|---|---|---|---|---|---|---|---|---|
| Lys | Leu | Gly | Pro | Ala | Leu | Ala | Ala | Gly | Asn | Ser | Val | Ile | Leu | Lys | Pro | |
| | | | 180 | | | | | 185 | | | | | 190 | | | |

| tct | gaa | aaa | tca | ccg | ctc | agt | gcg | att | cgt | ctc | gcg | ggg | ctg | gcg | aaa | 624 |
|---|---|---|---|---|---|---|---|---|---|---|---|---|---|---|---|---|
| Ser | Glu | Lys | Ser | Pro | Leu | Ser | Ala | Ile | Arg | Leu | Ala | Gly | Leu | Ala | Lys | |
| | | 195 | | | | | 200 | | | | | 205 | | | | |

| gaa | gca | ggc | ttg | ccg | gat | ggt | gtg | ttg | aac | gtg | gtg | acg | ggt | ttt | ggt | 672 |
|---|---|---|---|---|---|---|---|---|---|---|---|---|---|---|---|---|
| Glu | Ala | Gly | Leu | Pro | Asp | Gly | Val | Leu | Asn | Val | Val | Thr | Gly | Phe | Gly | |
| | 210 | | | | | 215 | | | | | 220 | | | | | |

| cat | gaa | gcc | ggg | cag | gcg | ctg | tcg | cgt | cat | aac | gat | atc | gac | gcc | att | 720 |
|---|---|---|---|---|---|---|---|---|---|---|---|---|---|---|---|---|
| His | Glu | Ala | Gly | Gln | Ala | Leu | Ser | Arg | His | Asn | Asp | Ile | Asp | Ala | Ile | |
| 225 | | | | 230 | | | | | 235 | | | | | 240 | | |

| gcc | ttt | acc | ggt | tca | acc | cgt | acc | ggg | aaa | cag | ctg | ctg | aaa | gat | gcg | 768 |
|---|---|---|---|---|---|---|---|---|---|---|---|---|---|---|---|---|
| Ala | Phe | Thr | Gly | Ser | Thr | Arg | Thr | Gly | Lys | Gln | Leu | Leu | Lys | Asp | Ala | |
| | | | 245 | | | | | 250 | | | | | 255 | | | |

| ggc | gac | agc | aac | atg | aaa | cgc | gtc | tgg | ctg | gaa | gcg | ggc | ggc | aaa | agc | 816 |
|---|---|---|---|---|---|---|---|---|---|---|---|---|---|---|---|---|
| Gly | Asp | Ser | Asn | Met | Lys | Arg | Val | Trp | Leu | Glu | Ala | Gly | Gly | Lys | Ser | |
| | | | 260 | | | | | 265 | | | | | 270 | | | |

```
gcc aac atc gtt ttc gct gac tgc ccg gat ttg caa cag gcg gca agc      864
Ala Asn Ile Val Phe Ala Asp Cys Pro Asp Leu Gln Gln Ala Ala Ser
        275                 280                 285 gcc acc gca gca ggc att ttc tac aac cag gga cag gtg tgc atc gcc      912
Ala Thr Ala Ala Gly Ile Phe Tyr Asn Gln Gly Gln Val Cys Ile Ala
    290                 295                 300 gga acg cgc ctg ttg ctg gaa gag agc atc gcc gat gaa ttc tta gcc      960
Gly Thr Arg Leu Leu Leu Glu Glu Ser Ile Ala Asp Glu Phe Leu Ala
305                 310                 315                 320 ctg tta aaa cag cag gcg caa aac tgg cag ccg ggc cat cca ctt gat     1008
Leu Leu Lys Gln Gln Ala Gln Asn Trp Gln Pro Gly His Pro Leu Asp
            325                 330                 335 ccc gca acc acc atg ggc acc tta atc gac tgc gcc cac gcc gac tcg     1056
Pro Ala Thr Thr Met Gly Thr Leu Ile Asp Cys Ala His Ala Asp Ser
        340                 345                 350 gtc cat agc ttt att cgg gaa ggc gaa agc aaa ggg caa ctg ttg ttg     1104
Val His Ser Phe Ile Arg Glu Gly Glu Ser Lys Gly Gln Leu Leu Leu
    355                 360                 365 gat ggc cgt aac gcc ggg ctg gct gcc gcc atc ggc ccg acc atc ttt     1152
Asp Gly Arg Asn Ala Gly Leu Ala Ala Ala Ile Gly Pro Thr Ile Phe
370                 375                 380 gtg gat gtg gac ccg aat gcg tcc tta agt cgc gaa gag att ttc ggt     1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag     1248
Pro Val Leu Val Val Thr Arg Phe Thr Ser Glu Glu Gln Ala Leu Gln
            405                 410                 415 ctt gcc aac gac agc cag tac ggc ctt ggc gcg gcg gta tgg acg cgc     1296
Leu Ala Asn Asp Ser Gln Tyr Gly Leu Gly Ala Ala Val Trp Thr Arg
        420                 425                 430 gac ctc tcc cgc gcg cac cgc atg agc cga cgc ctg aaa gcc ggt tcc     1344
Asp Leu Ser Arg Ala His Arg Met Ser Arg Arg Leu Lys Ala Gly Ser
    435                 440                 445 gtc ttc gtc aat aac tac aac gac ggc gat atg acc gtg ccg ttt ggc     1392
Val Phe Val Asn Asn Tyr Asn Asp Gly Asp Met Thr Val Pro Phe Gly
450                 455                 460 ggc tat aag cag agc ggc aac ggt cgc gac aaa tcc ctg cat gcc ctt     1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga     1488
Glu Lys Phe Thr Glu Leu Lys Thr Ile Trp Ile Ser Leu Glu Ala
            485                 490                 495

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
```

```
                    85                  90                  95
His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
            115                 120                 125

Arg Trp Tyr Ala Glu Ala Ile Asp Lys Val Tyr Gly Glu Val Ala Thr
        130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
    210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
    370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
    450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 21
<211> LENGTH: 1395
```

```
<212> TYPE: DNA
<213> ORGANISM: Escherichia coli

<400> SEQUENCE: 21
atgcctgacg ctaaaaaaca ggggcggtca acaaggcaa tgacgttttt cgtctgcttc      60
cttgccgctc tggcgggatt actctttggc ctggatatcg gtgtaattgc tggcgcactg     120
ccgtttattg cagatgaatt ccagattact tcgcacacgc aagaatgggt cgtaagctcc     180
atgatgttcg gtgcggcagt cggtgcggtg ggcagcggct ggctctcctt taaactcggg     240
cgcaaaaaga gcctgatgat cggcgcaatt ttgtttgttg ccggttcgct gttctctgcg     300
gctgcgccaa acgttgaagt actgattctt tcccgcgttc tactggggct ggcggtgggt     360
gtggcctctt ataccgcacc gctgtacctc tctgaaattg cgccggaaaa aattcgtggc     420
agtatgatct cgatgtatca gttgatgatc actatcggga tcctcggtgc ttatcttcct     480
gataccgcct tcagctacac cggtgcatgg cgctggatgc tgggtgtgat tatcatcccg     540
gcaattttgc tgctgattgg tgtcttcttc ctgccagaca gcccacgttg gtttgccgcc     600
aaacgccgtt tgttgatgc cgaacgcgtg ctgctacgcc tgcgtgacac cagcgcggaa     660
gcgaaacgcg aactggatga aatccgtgaa agtttgcagg ttaaacagag tggctgggcg     720
ctgtttaaag agaacagcaa cttccgccgc gcggtgttcc ttggcgtact gttgcaggta     780
atgcagcaat tcaccgggat gaacgtcatc atgtattacg cgccgaaaat cttcgaactg     840
gcgggttata ccaacactac cgagcaaatg tgggggaccg tgattgtcgg cctgaccaac     900
gtacttgcca cctttatcgc aatcggcctt gttgaccgct ggggacgtaa accaacgcta     960
acgctgggct tcctggtgat ggctgctggc atgggcgtac tcggtacaat gatgcatatc    1020
ggtattcact ctccgtcggc gcagtatttc gccatcgcca tgctgctgat gtttattgtc    1080
ggttttgcca tgagtgccgg tccgctgatt tgggtactgt gctccgaaat tcagccgctg    1140
aaaggccgcg attttggcat cacctgctcc actgccacca actggattgc caacatgatc    1200
gttggcgcaa cgttcctgac catgctcaac acgctgggta acgccaacac cttctgggtg    1260
tatgcggctc tgaacgtact gtttatcctg ctgacattgt ggctggtacc ggaaaccaaa    1320
cacgtttcgc tggaacatat tgaacgtaat ctgatgaaag gtcgtaaact gcgcgaaata    1380
ggcgctcacg attaa                                                    1395
```

<210> SEQ ID NO 22
<211> LENGTH: 464
<212> TYPE: PRT
<213> ORGANISM: Escherichia coli

<400> SEQUENCE: 22

```
Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Ala Pro Asn Val Glu Val Leu Ile Leu Ser Arg
```

|       |       |       |       |       | 100   |       |       |       |       | 105   |       |       |       |       | 110   |       |
|-------|-------|-------|-------|-------|-------|-------|-------|-------|-------|-------|-------|-------|-------|-------|-------|-------|

Val Leu Leu Gly Leu Ala Val Gly Val Ala Ser Tyr Thr Ala Pro Leu
              115                 120                 125

Tyr Leu Ser Glu Ile Ala Pro Glu Lys Ile Arg Gly Ser Met Ile Ser
130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
              165                 170                 175

Ile Ile Ile Pro Ala Ile Leu Leu Ile Gly Val Phe Phe Leu Pro
              180                 185                 190

Asp Ser Pro Arg Trp Phe Ala Ala Lys Arg Arg Phe Val Asp Ala Glu
              195                 200                 205

Arg Val Leu Leu Arg Leu Arg Asp Thr Ser Ala Glu Ala Lys Arg Glu
210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
              245                 250                 255

Leu Leu Gln Val Met Gln Gln Phe Thr Gly Met Asn Val Ile Met Tyr
              260                 265                 270

Tyr Ala Pro Lys Ile Phe Glu Leu Ala Gly Tyr Thr Asn Thr Thr Glu
              275                 280                 285

Gln Met Trp Gly Thr Val Ile Val Gly Leu Thr Asn Val Leu Ala Thr
290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
              325                 330                 335

Met Met His Ile Gly Ile His Ser Pro Ser Ala Gln Tyr Phe Ala Ile
              340                 345                 350

Ala Met Leu Leu Met Phe Ile Val Gly Phe Ala Met Ser Ala Gly Pro
              355                 360                 365

Leu Ile Trp Val Leu Cys Ser Glu Ile Gln Pro Leu Lys Gly Arg Asp
370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
              405                 410                 415

Thr Phe Trp Val Tyr Ala Ala Leu Asn Val Leu Phe Ile Leu Leu Thr
              420                 425                 430

Leu Trp Leu Val Pro Glu Thr Lys His Val Ser Leu Glu His Ile Glu
              435                 440                 445

Arg Asn Leu Met Lys Gly Arg Lys Leu Arg Glu Ile Gly Ala His Asp
              450                 455                 460

<210> SEQ ID NO 23
<211> LENGTH: 1248
<212> TYPE: DNA
<213> ORGANISM: Escherichia coli

<400> SEQUENCE: 23
atggcactga atattccatt cagaaatgcg tactatcgtt ttgcatccag ttactcattt      60 ctcttttta tttcctggtc gctgtggtgg tcgttatacg ctatttggct gaaaggacat     120

```
ctagggttga cagggacgga attaggtaca ctttattcgg tcaaccagtt taccagcatt    180
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctatttt tggcttgggg    360 tatctggcgg gatgcggttt gcttgatagc ttcaccgaaa aaatggcgcg aaattttcat    420
ttcgaatatg gaacagcgcg cgcctgggga tcttttggct atgctattgg cgcgttcttt    480
gccggcatat ttttagtat cagtccccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt tcaaggatcg aaacttctgg    660
gttttcgtca tatttattgt ggggacgtgg tctttctata acattttga tcaacaactt    720 tttcctgtct tttattcagg tttattcgaa tcacacgatg taggaacgcg cctgtatggt    780
tatctcaact cattccaggt ggtactcgaa gcgctgtgca tggcgattat tccttttcttt    840 gtgaatcggg tagggccaaa aaatgcatta cttatcggag ttgtgattat ggcgttgcgt    900 atccttttcct gcgcgctgtt cgttaaccc tggattattt cattagtgaa gttgttacat    960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag                 1248
```

<210> SEQ ID NO 24
<211> LENGTH: 415
<212> TYPE: PRT
<213> ORGANISM: Escherichia coli

<400> SEQUENCE: 24

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
                20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Leu Phe Met Met
        50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
```

```
                         180                 185                 190
Lys Asp His Gln Cys Val Ala Ala Asp Ala Gly Gly Val Lys Lys Glu
            195                 200                 205

Asp Phe Ile Ala Val Phe Lys Asp Arg Asn Phe Trp Val Phe Val Ile
        210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
        290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
        370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 25
<211> LENGTH: 1248
<212> TYPE: DNA
<213> ORGANISM: Artificial Sequence
<220> FEATURE:
<223> OTHER INFORMATION: variant cscB sequence with L61P substitution

<400> SEQUENCE: 25
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
ccatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt ggcttgggg     360 tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat ttttagtat cagtcccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acattttga tcaacaactt     720 tttcctgtct tttattcagg tttattcgaa tcacacgatg taggaacgcg cctgtatggt     780
```

```
tatctcaact cattccaggt ggtactcgaa gcgctgtgca tggcgattat tcctttcttt    840
gtgaatcggg tagggccaaa aaatgcatta cttatcggag ttgtgattat ggcgttgcgt    900
atcctttcct gcgcgctgtt cgttaacccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg cattttctt cttgagtaaa   1200 aaacgcgagc aaatagttat ggaaacgcct gtaccttcag caatatag              1248
```

<210> SEQ ID NO 26
<211> LENGTH: 415
<212> TYPE: PRT
<213> ORGANISM: Artificial Sequence
<220> FEATURE:
<223> OTHER INFORMATION: variant CscB sequence with L61P substitution

<400> SEQUENCE: 26

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Pro Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Val Asn Arg Val Gly Pro Lys Asn
        275                 280                 285
```

```
Ala Leu Leu Ile Gly Val Val Ile Met Ala Leu Arg Ile Leu Ser Cys
        290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415
```

<210> SEQ ID NO 27
<211> LENGTH: 1248
<212> TYPE: DNA
<213> ORGANISM: Artificial Sequence
<220> FEATURE:
<223> OTHER INFORMATION: variant cscB sequence with F159L substitution

<400> SEQUENCE: 27

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttattt     480
gccggcatat ttttagtat cagtccccat atcaacttct ggttggtctc gctatttggc     540
gctgtattta tgatgatcaa catgcgtttt aaagataagg atcaccagtg cgtagcggca     600
gatgcgggag ggtaaaaaa agaggatttt atcgcagttt tcaaggatcg aaacttctgg     660
gttttcgtca tatttattgt ggggacgtgg tcttttctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atccttttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag                1248
```

<210> SEQ ID NO 28
<211> LENGTH: 415
<212> TYPE: PRT

<213> ORGANISM: Artificial Sequence
<220> FEATURE:
<223> OTHER INFORMATION: variant CscB sequence with F159L substitution

<400> SEQUENCE: 28

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Leu Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400
```

Lys Arg Glu Gln Ile Val Met Glu Thr Pro Val Pro Ser Ala Ile
            405                 410                 415

<210> SEQ ID NO 29
<211> LENGTH: 1248
<212> TYPE: DNA
<213> ORGANISM: Artificial Sequence
<220> FEATURE:
<223> OTHER INFORMATION: variant cscB sequence with G162C substitution

<400> SEQUENCE: 29

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt    180
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctattttt tggcttgggg    360
tatctggcgg gatgcggttt gcttgatagc ttcaccgaaa aaatggcgcg aaattttcat    420
ttcgaatatg aacagcgcg cgcctgggga tcttttggct atgctattgg cgcgttcttt    480
gcctgcatat ttttagtat cagtccccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt tcaaggatcg aaacttctgg    660
gttttcgtca tatttattgt ggggacgtgg tctttctata cattttga tcaacaactt    720
tttcctgtct tttattcagg tttattcgaa tcacacgatg taggaacgcg cctgtatggt    780
tatctcaact cattccaggt ggtactcgaa gcgctgtgca tggcgattat tcctttcttt    840
gtgaatcggg tagggccaaa aaatgcatta cttatcggag ttgtgattat ggcgttgcgt    900
atccttttcct gcgcgctgtt cgttaacccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg cattttctt cttgagtaaa   1200
aaacgcgagc aaatagttat ggaaacgcct gtaccttcag caatatag              1248
```

<210> SEQ ID NO 30
<211> LENGTH: 415
<212> TYPE: PRT
<213> ORGANISM: Artificial Sequence
<220> FEATURE:
<223> OTHER INFORMATION: variant CscB sequence with G162C substitution

<400> SEQUENCE: 30

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
            85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
130                 135                 140

Thr Ala Arg Ala Trp Gly Ser Phe Gly Tyr Ala Ile Gly Ala Phe Phe
145                 150                 155                 160

Ala Cys Ile Phe Phe Ser Ile Ser Pro His Ile Asn Phe Trp Leu Val
            165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
            195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
            245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
            275                 280                 285

Ala Leu Leu Ile Gly Val Val Ile Met Ala Leu Arg Ile Leu Ser Cys
            290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 31
<211> LENGTH: 1248
<212> TYPE: DNA
<213> ORGANISM: Artificial Sequence
<220> FEATURE:
<223> OTHER INFORMATION: variant cscB with P169H substitution

<400> SEQUENCE: 31
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180

-continued

```
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctatttt tggcttgggg     360 tatctggcgg gatgcggttt gcttgatagc ttcaccgaaa aaatggcgcg aaattttcat    420
ttcgaatatg gaacagcgcg cgcctgggga tcttttggct atgctattgg cgcgttcttt   480
gccggcatat ttttagtat cagtcaccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt tcaaggatcg aaacttctgg    660
gttttcgtca tatttattgt ggggacgtgg tctttctata acatttttga tcaacaactt    720
tttcctgtct tttattcagg tttattcgaa tcacacgatg taggaacgcg cctgtatggt    780
tatctcaact cattccaggt ggtactcgaa gcgctgtgca tggcgattat tcctttcttt    840
gtgaatcggg tagggccaaa aaatgcatta cttatcggag ttgtgattat ggcgttgcgt    900 atccttttcct gcgcgctgtt cgttaacccc tggattattt cattagtgaa gttgttacat    960
gccattgagg ttccacttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag                1248
```

<210> SEQ ID NO 32
<211> LENGTH: 415
<212> TYPE: PRT
<213> ORGANISM: Artificial Sequence
<220> FEATURE:
<223> OTHER INFORMATION: variant CscB sequence with P169H substitution

<400> SEQUENCE: 32

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser His His Ile Asn Phe Trp Leu Val
                165                 170                 175

Ser Leu Phe Gly Ala Val Phe Met Met Ile Asn Met Arg Phe Lys Asp
```

```
                        180                 185                 190
Lys Asp His Gln Cys Val Ala Ala Asp Ala Gly Gly Val Lys Lys Glu
            195                 200                 205
Asp Phe Ile Ala Val Phe Lys Asp Arg Asn Phe Trp Val Phe Val Ile
        210                 215                 220
Phe Ile Val Gly Thr Trp Ser Phe Tyr Asn Ile Phe Asp Gln Gln Leu
225                 230                 235                 240
Phe Pro Val Phe Tyr Ser Gly Leu Phe Glu Ser His Asp Val Gly Thr
                245                 250                 255
Arg Leu Tyr Gly Tyr Leu Asn Ser Phe Gln Val Val Leu Glu Ala Leu
            260                 265                 270
Cys Met Ala Ile Ile Pro Phe Phe Val Asn Arg Val Gly Pro Lys Asn
        275                 280                 285
Ala Leu Leu Ile Gly Val Val Ile Met Ala Leu Arg Ile Leu Ser Cys
        290                 295                 300
Ala Leu Phe Val Asn Pro Trp Ile Ile Ser Leu Val Lys Leu Leu His
305                 310                 315                 320
Ala Ile Glu Val Pro Leu Cys Val Ile Ser Val Phe Lys Tyr Ser Val
                325                 330                 335
Ala Asn Phe Asp Lys Arg Leu Ser Ser Thr Ile Phe Leu Ile Gly Phe
            340                 345                 350
Gln Ile Ala Ser Ser Leu Gly Ile Val Leu Leu Ser Thr Pro Thr Gly
            355                 360                 365
Ile Leu Phe Asp His Ala Gly Tyr Gln Thr Val Phe Phe Ala Ile Ser
        370                 375                 380
Gly Ile Val Cys Leu Met Leu Leu Phe Gly Ile Phe Phe Leu Ser Lys
385                 390                 395                 400
Lys Arg Glu Gln Ile Val Met Glu Thr Pro Val Pro Ser Ala Ile
                405                 410                 415

<210> SEQ ID NO 33
<211> LENGTH: 1248
<212> TYPE: DNA
<213> ORGANISM: Artificial Sequence
<220> FEATURE:
<223> OTHER INFORMATION: variant cscB sequence with L61W substitution

<400> SEQUENCE: 33
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
tggtttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctgggg cgctattttt tggcttgggg      360
tatctggcgg atgcggttt gcttgatagc ttcaccgaaa aaatggcgcg aaattttcat     420
ttcgaatatg aacagcgcg cgcctgggga tcttttggct atgctattgg cgcgttcttt     480
gccggcatat ttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acattttga tcaacaactt     720 tttcctgtct tttattcagg tttattcgaa tcacacgatg taggaacgcg cctgtatggt     780
```

```
tatctcaact cattccaggt ggtactcgaa gcgctgtgca tggcgattat tcctttcttt    840
gtgaatcggg tagggccaaa aaatgcatta cttatcggag ttgtgattat ggcgttgcgt    900
atcctttcct gcgcgctgtt cgttaaccccc tggattattt cattagtgaa gttgttacat   960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt  1080
gtgctgcttt caacgccgac tgggatactc tttgaccacg caggctacca gacagttttc  1140
ttcgcaattt cgggtattgt ctgcctgatg ttgctatttg gcattttctt cttgagtaaa  1200
aaacgcgagc aaatagttat ggaaacgcct gtaccttcag caatatag              1248
```

<210> SEQ ID NO 34
<211> LENGTH: 415
<212> TYPE: PRT
<213> ORGANISM: Artificial Sequence
<220> FEATURE:
<223> OTHER INFORMATION: variant CscB sequence with L61W substitution

<400> SEQUENCE: 34

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Trp Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Val Asn Arg Val Gly Pro Lys Asn
        275                 280                 285
```

```
Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 35
<211> LENGTH: 1248
<212> TYPE: DNA
<213> ORGANISM: Artificial Sequence
<220> FEATURE:
<223> OTHER INFORMATION: variant cscB sequence with L61H substitution

<400> SEQUENCE: 35
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
cattttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttc     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag ggtaaaaaa agaggatttt atcgcagttt tcaaggatcg aaacttctgg     660
gttttcgtca tatttattgt ggggacgtgg tcttctctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900 atccttctcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcatttttctt cttgagtaaa    1200 aaacgcgagc aaatagttat ggaaacgcct gtaccttcag caatatag                 1248

<210> SEQ ID NO 36
<211> LENGTH: 415
<212> TYPE: PRT
```

<213> ORGANISM: Artificial Sequence
<220> FEATURE:
<223> OTHER INFORMATION: variant CscB sequence with L61H substitution

<400> SEQUENCE: 36

```
Met Ala Leu Asn Ile Pro Phe Arg Asn Ala Tyr Tyr Arg Phe Ala Ser
1               5                   10                  15

Ser Tyr Ser Phe Leu Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile His Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400
```

Lys Arg Glu Gln Ile Val Met Glu Thr Pro Val Pro Ser Ala Ile
              405                 410                 415

<210> SEQ ID NO 37
<211> LENGTH: 1248
<212> TYPE: DNA
<213> ORGANISM: Artificial Sequence
<220> FEATURE:
<223> OTHER INFORMATION: variant cscB sequence with L61F substitution

<400> SEQUENCE: 37

```
atggcactga atattccatt cagaaatgcg tactatcgtt ttgcatccag ttactcattt      60
ctctttttta tttcctggtc gctgtggtgg tcgttatacg ctatttggct gaaaggacat     120
ctagggttga cagggacgga attaggtaca ctttattcgg tcaaccagtt taccagcatt     180
tttttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg      360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acattttga tcaacaactt      720
tttcctgtct tttattcagg tttattcgaa tcacacgatg taggaacgcg cctgtatggt     780
tatctcaact cattccaggt ggtactcgaa gcgctgtgca tggcgattat tccttctttt     840
gtgaatcggg tagggccaaa aaatgcatta cttatcggag ttgtgattat ggcgttgcgt     900
atcctttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat cttctctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg cattttctt cttgagtaaa    1200
aaacgcgagc aaatagttat ggaaacgcct gtaccttcag caatatag                 1248
```

<210> SEQ ID NO 38
<211> LENGTH: 415
<212> TYPE: PRT
<213> ORGANISM: Artificial Sequence
<220> FEATURE:
<223> OTHER INFORMATION: variant CscB sequence wirth L61F substitution

<400> SEQUENCE: 38

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Phe Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 39
<211> LENGTH: 1248
<212> TYPE: DNA
<213> ORGANISM: Artificial Sequence
<220> FEATURE:
<223> OTHER INFORMATION: variant cscB sequence with L61Y substitution

<400> SEQUENCE: 39
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt    180

```
tattttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctattttt tggcttgggg    360
tatctggcgg gatgcggttt gcttgatagc ttcaccgaaa aaatggcgcg aaattttcat    420
ttcgaatatg gaacagcgcg cgcctgggga tcttttggct atgctattgg cgcgttcttt    480
gccggcatat tttttagtat cagtcccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt caaggatcg aaacttctgg    660 gttttcgtca tatttattgt ggggacgtgg tctttctata acattttga tcaacaactt    720 tttcctgtct tttattcagg tttattcgaa tcacacgatg taggaacgcg cctgtatggt    780
tatctcaact cattccaggt ggtactcgaa gcgctgtgca tggcgattat tccttctttt    840
gtgaatcggg tagggccaaa aaatgcatta cttatcggag ttgtgattat ggcgttgcgt    900 atccttcct gcgcgctgtt cgttaaccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag                1248
```

<210> SEQ ID NO 40
<211> LENGTH: 415
<212> TYPE: PRT
<213> ORGANISM: Artificial Sequence
<220> FEATURE:
<223> OTHER INFORMATION: variant cscB sequence with L61Y substitution

<400> SEQUENCE: 40

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Tyr Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
```

|     |     |     |     |     |     |     |     |     |     |     |     |
| --- | --- | --- | --- | --- | --- | --- | --- | --- | --- | --- | --- |
|     |     |     | 180 |     |     |     | 185 |     |     |     | 190 |
| Lys | Asp | His | Gln | Cys | Val | Ala | Ala | Asp | Ala | Gly | Gly | Val | Lys | Lys | Glu |
|     |     |     | 195 |     |     |     | 200 |     |     |     | 205 |

Lys Asp His Gln Cys Val Ala Ala Asp Ala Gly Gly Val Lys Lys Glu
                195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
                260                 265                 270

Cys Met Ala Ile Ile Pro Phe Phe Val Asn Arg Val Gly Pro Lys Asn
                275                 280                 285

Ala Leu Leu Ile Gly Val Val Ile Met Ala Leu Arg Ile Leu Ser Cys
                290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
                370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 41
<211> LENGTH: 1248
<212> TYPE: DNA
<213> ORGANISM: Artificial Sequence
<220> FEATURE:
<223> OTHER INFORMATION: variant cscB sequence with 403 stop

<400> SEQUENCE: 41
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaatttttc tgtaggtcta attctggggg cgctattttt ggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat ttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tcttctctata acatttttga tcaacaactt     720
tttcctgtct tttattcagg tttattcgaa tcacacgatg taggaacgcg cctgtatggt     780

```
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atcctttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgctagc aaatagttat ggaaacgcct gtaccttcag caatatag                 1248
```

<210> SEQ ID NO 42  
<211> LENGTH: 402  
<212> TYPE: PRT  
<213> ORGANISM: Artificial Sequence  
<220> FEATURE:  
<223> OTHER INFORMATION: variant CscB sequence with 403 stop

<400> SEQUENCE: 42

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Val Asn Arg Val Gly Pro Lys Asn
        275                 280                 285
```

```
Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg

<210> SEQ ID NO 43
<211> LENGTH: 1248
<212> TYPE: DNA
<213> ORGANISM: Artificial Sequence
<220> FEATURE:
<223> OTHER INFORMATION: variant cscB sequence with 408 stop

<400> SEQUENCE: 43
atggcactga atattccatt cagaaatgcg tactatcgtt ttgcatccag ttactcattt      60
ctctttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat ttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atcctttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat gtaaacgcct gtaccttcag caatatag                1248

<210> SEQ ID NO 44
<211> LENGTH: 407
<212> TYPE: PRT
<213> ORGANISM: Artificial Sequence
```

-continued

<220> FEATURE:
<223> OTHER INFORMATION: variant CscB sequence with 408 stop

<400> SEQUENCE: 44

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met
            405

<210> SEQ ID NO 45
<211> LENGTH: 4146
<212> TYPE: DNA
<213> ORGANISM: Escherichia coli

<400> SEQUENCE: 45

| | | | | | |
|---|---|---|---|---|---|
| ggatcccttg | cccgctgttg | atccgttgtt | ccacctgata | ttatgttaac | ccagtagcca | 60 |
| gagtgctcca | tgttgcagca | cagccactcc | gtgggaggca | taaagcgaca | gttcccgttc | 120 |
| ttctggctgc | ggatagattc | gactactcat | caccgcttcc | ccgtcgttaa | taaatacttc | 180 |
| cacggatgat | gtatcgataa | atatccttag | ggcgagcgtg | tcacgctgcg | ggaggggaat | 240 |
| actacggtag | ccgtctaaat | tctcgtgtgg | gtaataccgc | cacaaaacaa | gtcgctcaga | 300 |
| ttggttatca | atatacagcc | gcattccagt | gccgagctgt | aatccgtaat | gttcggcatc | 360 |
| actgttcttc | agcgcccact | gcaactgaat | ctcaactgct | tgcgcgtttt | cctgcaaaac | 420 |
| atatttattg | ctgattgtgc | ggggagagac | agattgatgc | tgctggcgta | acgactcagc | 480 |
| ttcgtgtacc | gggcgttgta | gaagtttgcc | attgctctct | gatagctcgc | gcgccagcgt | 540 |
| catgcagcct | gcccatcctt | cacgttttga | gggcattggc | gattcccaca | tatccatcca | 600 |
| gccgataaca | atacgccgac | catccttcgc | taaaaagctt | tgtggtgcat | aaaagtcatg | 660 |
| cccgttatca | agttcagtaa | aatgcccgga | ttgtgcaaaa | agtcgtcctg | gcgaccacat | 720 |
| tccgggtatt | acgccacttt | gaaagcgatt | tcggtaactg | tatccctcgg | cattcattcc | 780 |
| ctgcggggaa | aacatcagat | aatgctgatc | gccaaggctg | aaaaagtccg | gacattccca | 840 |
| catatagctt | tcacccgcat | cagcgtgggc | cagtacgcga | tcgaaggtcc | attcacgcaa | 900 |
| cgaactgccg | cgataaagca | ggatctgccc | cgtgttgcct | ggatctttcg | ccccgactac | 960 |
| catccaccat | gtgtcggctt | cacgccacac | tttaggatcg | cggaagtgca | tgattccttc | 1020 |
| tggtggagtg | aggatcacac | cctgtttctc | gaaatgaata | ccatcccgac | tggtagccag | 1080 |
| acattgtact | tcgcgaattg | catcgtcatt | acctgcacca | tcgagccaga | cgtgtccggt | 1140 |
| gtagataagt | gagaggacac | cattgtcatc | gacagcacta | cctgaaaaac | accgtctttt | 1200 |
| gtcattatcg | tctcctggcg | ctagcgcaat | aggctcatgc | tgccagtgga | tcatatcgtc | 1260 |
| gctggtggca | tgtccccagt | gcattggccc | ccagtgttcg | ctcatcggat | gatgttgata | 1320 |
| aaacgcgtga | taacgatcgt | taaccagat | caggccgttt | ggatcgttca | tccaccggc | 1380 |
| aggaggcgcg | aggtgaaaat | ggggatagaa | agtgttaccc | cggtgctcat | gaagttttgc | 1440 |
| tagggcgttt | tgcgccgcat | gcaatcgaga | ttgcgtcatt | ttaatcatcc | tggttaagca | 1500 |
| aatttggtga | attgttaacg | ttaacttta | taaaaataaa | gtcccttact | ttcataaatg | 1560 |
| cgatgaatat | cacaaatgtt | aacgttaact | atgacgtttt | gtgatcgaat | atgcatgttt | 1620 |
| tagtaaatcc | atgacgattt | tgcgaaaaag | aggtttatca | ctatgcgtaa | ctcagatgaa | 1680 |
| tttaagggaa | aaaaatgtca | gccaaagtat | gggttttagg | gatgcggtc | gtagatctct | 1740 |
| tgccagaatc | agacgggcgc | ctactgcctt | gtcctggcgg | cgcgccagct | aacgttgcgg | 1800 |
| tgggaatcgc | cagattaggc | ggaacaagtg | ggttatagg | tcgggtgggg | gatgatcctt | 1860 |
| ttggtgcgtt | aatgcaaaga | acgctgctaa | ctgagggagt | cgatatcacg | tatctgaagc | 1920 |
| aagatgaatg | gcaccggaca | tccacggtgc | ttgtcgatct | gaacgatcaa | ggggaacgtt | 1980 |
| catttacgtt | tatggtccgc | cccagtgccg | atcttttttt | agagacgaca | gacttgccct | 2040 |
| gctggcgaca | tggcgaatgg | ttacatctct | gttcaattgc | gttgtctgcc | gagccttcgc | 2100 |

```
gtaccagcgc atttactgcg atgacggcga tccggcatgc cggaggtttt gtcagcttcg    2160
atcctaatat tcgtgaagat ctatggcaag acgagcattt gctccgcttg tgtttgcggc    2220
aggcgctaca actggcggat gtcgtcaagc tctcggaaga agaatggcga cttatcagtg    2280
gaaaaacaca gaacgatcag gatatatgcg ccctggcaaa agagtatgag atcgccatgc    2340
tgttggtgac taaaggtgca gaaggggtgg tggtctgtta tcgaggacaa gttcaccatt    2400
ttgctggaat gtctgtgaat tgtgtcgata gcacggggggc gggagatgcg ttcgttgccg    2460
ggttactcac aggtctgtcc tctacgggat tatctacaga tgagagagaa atgcgacgaa    2520
ttatcgatct cgctcaacgt tgcggagcgc ttgcagtaac ggcgaaaggg gcaatgacag    2580
cgctgccatg tcgacaagaa ctggaatagt gagaagtaaa cggcgaagtc gctcttatct    2640
ctaaatagga cgtgaatttt ttaacgacag gcaggtaatt atggcactga atattccatt    2700
cagaaatgcg tactatcgtt ttgcatccag ttactcattt ctcttttta tttcctggtc    2760 gctgtggtgg tcgttatacg ctatttggct gaaaggacta ctagggttga cagggacgga    2820
attaggtaca ctttattcgg tcaaccagtt taccagcatt ctatttatga tgttctacgg    2880
catcgttcag gataaactcg gtctgaagaa accgctcatc tggtgtatga gtttcatcct    2940
ggtcttgacc ggaccgttta tgatttacgt ttatgaaccg ttactgcaaa gcaatttttc    3000
tgtaggtcta attctggggg cgctattttt tggcttgggg tatctggcgg gatgcggttt    3060
gcttgatagc ttcaccgaaa aaatggcgcg aaattttcat ttcgaatatg aacagcgcg    3120 cgcctgggga tcttttggct atgctattgg cgcgttcttt gccggcatat tttttagtat    3180
cagtccccat atcaacttct ggttggtctc gctatttggc gctgtattta tgatgatcaa    3240
catgcgtttt aaagataagg atcaccagtg cgtagcggca gatgcgggag gggtaaaaaa    3300
agaggatttt atcgcagttt tcaaggatcg aaacttctgg gttttcgtca tatttattgt    3360
ggggacgtgg tctttctata acattttga tcaacaactt ttcctgtct tttattcagg    3420 tttattcgaa tcacacgatg taggaacgcg cctgtatggt tatctcaact cattccaggt    3480
ggtactcgaa gcgctgtgca tggcgattat tcctttcttt gtgaatcggg tagggccaaa    3540
aaatgcatta cttatcggag ttgtgattat ggcgttgcgt atcctttcct gcgcgctgtt    3600 cgttaaccc tggattattt cattagtgaa gttgttacat gccattgagg ttccactttg    3660
tgtcatatcc gtcttcaaat acagcgtggc aaactttgat aagcgcctgt cgtcgacgat    3720
ctttctgatt ggttttcaaa ttgccagttc gcttgggatt gtgctgcttt caacgccgac    3780
tgggatactc tttgaccacg caggctacca gacagttttc ttcgcaattt cgggtattgt    3840
ctgcctgatg ttgctatttg gcatttctctt cttgagtaaa aaacgcgagc aaatagttat    3900
ggaaacgcct gtaccttcag caatatagac gtaaactttt tccggttgtt gtcgatagct    3960
ctatatccct caaccggaaa ataataatag taaaatgctt agccctgcta ataatcgcct    4020
aatccaaacg cctcattcat gttctggtac agtcgctcaa atgtacttca gatgcgcggt    4080
tcgctgattt ccaggacatt gtcgtcattc agtgacctgt cccgtgtatc acggtcctgc    4140
gaattc                                                               4146
```

<210> SEQ ID NO 46
<211> LENGTH: 1434
<212> TYPE: DNA
<213> ORGANISM: Escherichia coli

<400> SEQUENCE: 46

```
atgacgcaat ctcgattgca tgcggcgcaa aacgcactag caaaacttca cgagcgccga      60
```

```
ggtaacactt tctatcccca ttttcacctc gcgcctcctg ccgggtggat gaacgatcca    120
aacggcctga tctggtttaa cgatcgttat cacgcgtttt atcaacatca cccgatgagc    180
gaacactggg ggccaatgca ctggggacat gccaccagcg acgatatgat ccactggcag    240
catgagccta ttgcgctagc gccaggagac gagaatgaca aagacgggtg ttttcaggt     300 agtgctgtcg atgacaatgg tgtcctctca cttatctaca ccggacacgt ctggctcgat    360
ggtgcaggta atgacgatgc aattcgcgaa gtacaatgtc tggctaccag tcgggatggt    420
attcatttcg agaaacaggg tgtgatcctc actccaccag aaggcatcat gcacttccgc    480
gatcctaaag tgtggcgtga agccgacaca tggtggatgg tagtcggggc gaaagaccca    540
ggcaacacgg ggcagatcct gctttatcgc ggcagttcat tgcgtgaatg gactttcgat    600
cgcgtactgg cccacgctga tgcgggtgaa agctatatgt gggaatgtcc ggacttttc    660 agccttggcg atcagcatta tctgatgttt tccccgcagg gaatgaatgc cgagggatac    720
agttatcgaa atcgctttca aagtggcgta atacccggaa tgtggtcgcc aggacgactt    780
tttgcacaat ccgggcattt tactgaactt gataacgggc atgactttta tgcaccacaa    840
agctttgtag cgaaggatgg tcggcgtatt gttatcggct ggatggatat gtgggaatcg    900
ccaatgccct caaaacgtga aggctgggca ggctgcatga cgctggcgcg cgagctatca    960
gagagcaatg gcaaactcct acaacgcccg gtacacgaag ctgagtcgtt acgccagcag   1020
catcaatcta tctctccccg cacaatcagc aataaatatg ttttgcagga aaacgcgcaa   1080
gcagttgaga ttcagttgca gtgggcgctg aagaacagtg atgccgaaca ttacggatta   1140
cagctcggcg ctggaatgcg gctgtatatt gataaccaat ctgagcgact tgttttgtgg   1200
cggtattacc cacacgagaa tttagatggc taccgtagta ttccctccc gcagggtgac    1260 atgctcgccc taaggatatt tatcgataca tcatccgtgg aagtatttat taacgacggg   1320
gaggcggtga tgagtagccg aatatatccg cagccagaag aacgggaact gtcgctctat   1380
gcctcccacg gagtggctgt gctgcaacat ggagcactct ggcaactggg ttaa          1434
```

<210> SEQ ID NO 47
<211> LENGTH: 477
<212> TYPE: PRT
<213> ORGANISM: Escherichia coli

<400> SEQUENCE: 47

```
Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Glu Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
```

|   |   |   |   |   |   |   |   |   |   |
|---|---|---|---|---|---|---|---|---|---|
| Lys | Gln | Gly | Val | Ile | Leu | Thr | Pro | Pro | Glu | Gly | Ile | Met | His | Phe | Arg |
| 145 | | | | 150 | | | | | 155 | | | | | 160 | |

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Met Val Val Gly
            165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
            195                 200                 205

Gly Glu Ser Tyr Met Trp Glu Cys Pro Asp Phe Phe Ser Leu Gly Asp
210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
            245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Val Ala Lys Asp Gly Arg
            275                 280                 285

Arg Ile Val Ile Gly Trp Met Asp Met Trp Glu Ser Pro Met Pro Ser
290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
            325                 330                 335

Leu Arg Gln Gln His Gln Ser Ile Ser Pro Arg Thr Ile Ser Asn Lys
            340                 345                 350

Tyr Val Leu Gln Glu Asn Ala Gln Ala Val Glu Ile Gln Leu Gln Trp
            355                 360                 365

Ala Leu Lys Asn Ser Asp Ala Glu His Tyr Gly Leu Gln Leu Gly Ala
            370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
            405                 410                 415

Pro Gln Gly Asp Met Leu Ala Leu Arg Ile Phe Ile Asp Thr Ser Ser
            420                 425                 430

Val Glu Val Phe Ile Asn Asp Gly Glu Ala Val Met Ser Ser Arg Ile
            435                 440                 445

Tyr Pro Gln Pro Glu Glu Arg Glu Leu Ser Leu Tyr Ala Ser His Gly
            450                 455                 460

Val Ala Val Leu Gln His Gly Ala Leu Trp Gln Leu Gly
465                 470                 475

<210> SEQ ID NO 48
<211> LENGTH: 1434
<212> TYPE: DNA
<213> ORGANISM: Escherichia coli

<400> SEQUENCE: 48
atgacgcaat ctcgattgca tgcggcgcaa aacgccctag caaaacttca tgagcaccgg     60
ggtaacactt tctatcccca ttttcacctc gcgcctcctg ccgggtggat gaacgatcca    120
aacggcctga tctggtttaa cgatcgttat cacgcgtttt atcaacatca tccgatgagc    180
gaacactggg ggccaatgca ctggggacat gccaccagcg acgatatgat ccactggcag    240

```
catgagccta ttgcgctagc gccaggagac gataatgaca aagacgggtg ttttcaggt       300 agtgctgtcg atgacaatgg tgtcctctca cttatctaca ccggacacgt ctggctcgat       360
ggtgcaggta atgacgatgc aattcgcgaa gtacaatgtc tggctaccag tcgggatggt       420
attcatttcg agaaacaggg tgtgatcctc actccaccag aaggaatcat gcacttccgc       480
gatcctaaag tgtggcgtga agccgacaca tggtggatgg tagtcggggc gaaagatcca       540
ggcaacacgg ggcagatcct gctttatcgc ggcagttcgt tgcgtgaatg gaccttcgat       600
cgcgtactgg cccacgctga tgcgggtgaa agctatatgt gggaatgtcc ggactttttc       660
agccttggcg atcagcatta tctgatgttt tccccgcagg gaatgaatgc cgagggatac       720
agttaccgaa atcgctttca aagtggcgta atacccggaa tgtggtcgcc aggacgactt       780
tttgcacaat ccgggcattt tactgaactt gataacgggc atgacttta tgcaccacaa       840 agctttttag cgaaggatgg tcggcgtatt gttatcggct ggatggatat gtgggaatcg       900
ccaatgccct caaaacgtga aggatgggca ggctgcatga cgctggcgcg cgagctatca       960
gagagcaatg gcaaacttct acaacgcccg gtacacgaag ctgagtcgtt acgccagcag      1020
catcaatctg tctctccccg cacaatcagc aataaatatg ttttgcagga aaacgcgcaa      1080
gcagttgaga ttcagttgca gtgggcgctg aagaacagtg atgccgaaca ttacggatta      1140
cagctcggca ctggaatgcg gctgtatatt gataaccaat ctgagcgact tgttttgtgg      1200
cggtattacc cacacgagaa tttagacggc taccgtagta ttcccctccc gcagcgtgac      1260
acgctcgccc taaggatatt tatcgataca tcatccgtgg aagtatttat taacgacggg      1320
gaagcggtga tgagtagtcg aatctatccg cagccagaag aacgggaact gtcgctttat      1380
gcctcccacg gagtggctgt gctgcaacat ggagcactct ggctactggg ttaa            1434
```

<210> SEQ ID NO 49
<211> LENGTH: 477
<212> TYPE: PRT
<213> ORGANISM: Escherichia coli

<400> SEQUENCE: 49

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
                20                  25                  30

Pro Ala Gly Trp Met Asn Asp Pro Asn Gly Leu Ile Trp Phe Asn Asp
            35                  40                  45

Arg Tyr His Ala Phe Tyr Gln His Pro Met Ser Glu His Trp Gly
        50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
```

```
                     165                 170                 175
Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
            195                 200                 205

Gly Glu Ser Tyr Met Trp Glu Cys Pro Asp Phe Phe Ser Leu Gly Asp
            210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
            245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
            275                 280                 285

Arg Ile Val Ile Gly Trp Met Asp Met Trp Glu Ser Pro Met Pro Ser
            290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
            325                 330                 335

Leu Arg Gln Gln His Gln Ser Val Ser Pro Arg Thr Ile Ser Asn Lys
            340                 345                 350

Tyr Val Leu Gln Glu Asn Ala Gln Ala Val Glu Ile Gln Leu Gln Trp
            355                 360                 365

Ala Leu Lys Asn Ser Asp Ala Glu His Tyr Gly Leu Gln Leu Gly Thr
            370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
            405                 410                 415

Pro Gln Arg Asp Thr Leu Ala Leu Arg Ile Phe Ile Asp Thr Ser Ser
            420                 425                 430

Val Glu Val Phe Ile Asn Asp Gly Glu Ala Val Met Ser Ser Arg Ile
            435                 440                 445

Tyr Pro Gln Pro Glu Glu Arg Glu Leu Ser Leu Tyr Ala Ser His Gly
            450                 455                 460

Val Ala Val Leu Gln His Gly Ala Leu Trp Leu Leu Gly
465                 470                 475

<210> SEQ ID NO 50
<211> LENGTH: 1599
<212> TYPE: DNA
<213> ORGANISM: Bifidobacterium lactis

<400> SEQUENCE: 50
atggcaaccc ttcccaccaa tattcccgcc aacggcattc tgaccccga cccggcgctc    60 gaccctgtgc tcacgccgat ctcggaccat gccgagcagc tgtcactcgc cgaagcaggc   120
gtgtcggcac tggaaaccac ccgcaacgac cgctggtacc cgaagttcca cattgcctcc   180
aatggcgggt ggatcaacga cccgaacggc ctgtgccgct acaacggacg ctggcacgtg   240
ttctaccagc tgcatcccca cggcacacag tggggcccga tgcattgggg ccacgtctcc   300
tccgacaaca tggtcgactg gcaccgcgaa cccatcgcct tcgcgccaag cctcgaacag   360
gaacgccacg gtgtgttctc cggttccgcc gtgattggcg acgacggcaa gccgtggatt   420
```

```
ttctacaccg gccaccgctg ggccaacggc aaggacaaca ccggaggcga ctggcaggtg      480
cagatgctcg ccaagccgaa cgacgacgaa ctgaagacct tcacgaagga gggcatgatc      540
atcgactgcc ccaccgacga ggtggaccac cacttccgcg acccgaaggt gtggaagacc      600
ggtgacacct ggtatatgac cttcggtgtc tcgtcgaagg agcatcgtgg ccagatgtgg      660
ctgtacacgt cgagcgacat ggtgcactgg agcttcgatc gggtgctgtt cgagcatccg      720
gatccgaacg tgttcatgct tgaatgcccc gatttcttcc cgatccgcga tgcgcggggc      780
aacgagaaat gggtcatcgg cttctccgcg atgggtgcca agccaaatgg cttcatgaac      840
cgcaacgtga acaatgccgg ctacatggtg ggcacatgga agcaggcga gagcttcaag      900 ccggagaccg agtccgcct gtgggacgaa ggccataact tctatgcacc acagtcgttc      960
aacaccgaag gcgccagat catgtacggc tggatgagcc cgttcgtcgc ccccatcccg     1020
atggaggagg acggctggtg cggcaacctc accctccccc gcgagatcac gctgggcgat     1080
gacggtgacc tggtcaccgc ccccaccatc gaaatggagg ggctgcgcga gaataccata     1140
ggcttcgact cgctcgacct tggtacgaac cagacctcca cgatcctcga cgatgacggc     1200
ggcgccctgg aaatcgagat gagactcgat ctgaacaaaa ccaccgccga acgcgccgga     1260
ctgcatgtgc atgccacaag cgacggccac tacacggcaa tcgtattcga cgcgcagatc     1320
ggcggcgtcc tcatcgaccg gcagaacgtg gcgaacggga caaaggcta ccgggtggcc     1380 aagctcagcg acaccgagct cgcagccgat acgcttgact tgcgcgtgtt catcgaccgc     1440
ggatgcgtcg aggtctacgt cgacggcggc aagcatgcga tgagctcgta ctcgttccct     1500
ggcgatggcg cacgcgccgt cgaactcgtg agcgaatccg gcaccacgca catcgacacc     1560
ctcaccatgc actcgctcaa gtccatcgga ctcgagtga                            1599
```

<210> SEQ ID NO 51
<211> LENGTH: 532
<212> TYPE: PRT
<213> ORGANISM: Bifidobacterium lactis

<400> SEQUENCE: 51

```
Met Ala Thr Leu Pro Thr Asn Ile Pro Ala Asn Gly Ile Leu Thr Pro
1               5                   10                  15

Asp Pro Ala Leu Asp Pro Val Leu Thr Pro Ile Ser Asp His Ala Glu
            20                  25                  30

Gln Leu Ser Leu Ala Glu Ala Gly Val Ser Ala Leu Glu Thr Thr Arg
        35                  40                  45

Asn Asp Arg Trp Tyr Pro Lys Phe His Ile Ala Ser Asn Gly Gly Trp
    50                  55                  60

Ile Asn Asp Pro Asn Gly Leu Cys Arg Tyr Asn Gly Arg Trp His Val
65                  70                  75                  80

Phe Tyr Gln Leu His Pro His Gly Thr Gln Trp Gly Pro Met His Trp
                85                  90                  95

Gly His Val Ser Ser Asp Asn Met Val Asp Trp His Arg Glu Pro Ile
            100                 105                 110

Ala Phe Ala Pro Ser Leu Glu Gln Glu Arg His Gly Val Phe Ser Gly
        115                 120                 125

Ser Ala Val Ile Gly Asp Asp Gly Lys Pro Trp Ile Phe Tyr Thr Gly
    130                 135                 140

His Arg Trp Ala Asn Gly Lys Asp Asn Thr Gly Gly Asp Trp Gln Val
145                 150                 155                 160

Gln Met Leu Ala Lys Pro Asn Asp Asp Glu Leu Lys Thr Phe Thr Lys
```

```
                    165                 170                 175
Glu Gly Met Ile Ile Asp Cys Pro Thr Asp Glu Val Asp His His Phe
                180                 185                 190

Arg Asp Pro Lys Val Trp Lys Thr Gly Asp Thr Trp Tyr Met Thr Phe
            195                 200                 205

Gly Val Ser Ser Lys Glu His Arg Gly Gln Met Trp Leu Tyr Thr Ser
        210                 215                 220

Ser Asp Met Val His Trp Ser Phe Asp Arg Val Leu Phe Glu His Pro
225                 230                 235                 240

Asp Pro Asn Val Phe Met Leu Glu Cys Pro Asp Phe Phe Pro Ile Arg
                245                 250                 255

Asp Ala Arg Gly Asn Glu Lys Trp Val Ile Gly Phe Ser Ala Met Gly
                260                 265                 270

Ala Lys Pro Asn Gly Phe Met Asn Arg Asn Val Asn Asn Ala Gly Tyr
            275                 280                 285

Met Val Gly Thr Trp Lys Pro Gly Glu Ser Phe Lys Pro Glu Thr Glu
        290                 295                 300

Phe Arg Leu Trp Asp Glu Gly His Asn Phe Tyr Ala Pro Gln Ser Phe
305                 310                 315                 320

Asn Thr Glu Gly Arg Gln Ile Met Tyr Gly Trp Met Ser Pro Phe Val
                325                 330                 335

Ala Pro Ile Pro Met Glu Glu Asp Gly Trp Cys Gly Asn Leu Thr Leu
                340                 345                 350

Pro Arg Glu Ile Thr Leu Gly Asp Asp Gly Asp Leu Val Thr Ala Pro
            355                 360                 365

Thr Ile Glu Met Glu Gly Leu Arg Glu Asn Thr Ile Gly Phe Asp Ser
        370                 375                 380

Leu Asp Leu Gly Thr Asn Gln Thr Ser Thr Ile Leu Asp Asp Asp Gly
385                 390                 395                 400

Gly Ala Leu Glu Ile Glu Met Arg Leu Asp Leu Asn Lys Thr Thr Ala
                405                 410                 415

Glu Arg Ala Gly Leu His Val His Ala Thr Ser Asp Gly His Tyr Thr
                420                 425                 430

Ala Ile Val Phe Asp Ala Gln Ile Gly Gly Val Val Ile Asp Arg Gln
            435                 440                 445

Asn Val Ala Asn Gly Asp Lys Gly Tyr Arg Val Ala Lys Leu Ser Asp
        450                 455                 460

Thr Glu Leu Ala Ala Asp Thr Leu Asp Leu Arg Val Phe Ile Asp Arg
465                 470                 475                 480

Gly Cys Val Glu Val Tyr Val Asp Gly Gly Lys His Ala Met Ser Ser
                485                 490                 495

Tyr Ser Phe Pro Gly Asp Gly Ala Arg Ala Val Glu Leu Val Ser Glu
                500                 505                 510

Ser Gly Thr Thr His Ile Asp Thr Leu Thr Met His Ser Leu Lys Ser
            515                 520                 525

Ile Gly Leu Glu
    530

<210> SEQ ID NO 52
<211> LENGTH: 1599
<212> TYPE: DNA
<213> ORGANISM: Saccharomyces cerevisiae

<400> SEQUENCE: 52
atgcttttgc aagcttttcct tttccttttg ctggttttg cagccaaaat atctgcatca    60
```

```
atgacaaacg aaactagcga tagacctttg gtccacttca cacccaacaa gggctggatg     120
aatgacccaa atgggttgtg gtacgatgaa aaagatgcca atggcatct gtactttcaa      180 tacaacccaa atgacaccgt atggggtacg ccattgtttt ggggccatgc tacttccgat     240
gatttgacta attgggaaga tcaacccatt gctatcgctc caagcgtaa cgattcaggt      300 gctttctctg gctccatggt ggttgattac aacaacacga gtgggttttt caatgatact     360
attgatccaa gacaaagatg cgttgcgatt tggacttata acactcctga agtgaagag      420 caatacatta gctattctct tgatggtggt tacactttta ctgaatacca aaagaaccct     480
gttttagctg ccaactccac tcaattcaga gatccaaagg tgttctggta tgaaccttct     540
caaaaatgga ttatgacggc tgccaaatca aagactaca aaattgaaat ttactcctct     600
gatgacttga agtcctggaa gctagaatct gcatttgcca atgaaggttt cttaggctac     660
caatacgaat gtccaggttt gattgaagtc ccaactgagc aagatccttc caaatcttat     720
tgggtcatgt ttatttctat caacccaggt gcacctgctg gcggttcctt caaccaatat     780
tttgttggat ccttcaatgg tactcatttt gaagcgtttg acaatcaatc tagagtggta     840
gattttggta aggactacta tgccttgcaa actttcttca acactgaccc aacctacggt     900
tcagcattag gtattgcctg ggcttcaaac tgggagtaca gtgcctttgt cccaactaac     960
ccatggagat catccatgtc tttggtccgc aagtttctt tgaacactga atatcaagct     1020
aatccagaga ctgaattgat caatttgaaa gccgaaccaa tattgaacat tagtaatgct    1080
ggtccctggt ctcgttttgc tactaacaca actctaacta aggccaattc ttacaatgtc    1140
gatttgagca actcgactgg taccctagag tttgagttgg tttacgctgt taacaccaca    1200
caaaccatat ccaaatccgt cttttgccgac ttatcacttt ggttcaaggg tttagaagat    1260
cctgaagaat atttgagaat gggttttgaa gtcagtgctt cttccttctt tttggaccgt    1320
ggtaactcta aggtcaagtt tgtcaaggag aacccatatt tcacaaacag aatgtctgtc    1380
aacaaccaac cattcaagtc tgagaacgac ctaagttact ataaagtgta cggcctactg    1440
gatcaaaaca tcttggaatt gtacttcaac gatggagatg tggtttctac aaataccac     1500 ttcatgacca ccggtaacgc tctaggatct gtgaacatga ccactggtgt cgataatttg    1560
ttctacattg acaagttcca agtaagggaa gtaaaatag                            1599
```

<210> SEQ ID NO 53
<211> LENGTH: 532
<212> TYPE: PRT
<213> ORGANISM: Saccharomyces cerevisiae

<400> SEQUENCE: 53

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
```

-continued

```
                100                 105                 110
Thr Ser Gly Phe Phe Asn Asp Thr Ile Asp Pro Arg Gln Arg Cys Val
            115                 120                 125
Ala Ile Trp Thr Tyr Asn Thr Pro Glu Ser Glu Gln Tyr Ile Ser
    130                 135                 140
Tyr Ser Leu Asp Gly Gly Tyr Thr Phe Thr Glu Tyr Gln Lys Asn Pro
145                 150                 155                 160
Val Leu Ala Ala Asn Ser Thr Gln Phe Arg Asp Pro Lys Val Phe Trp
            165                 170                 175
Tyr Glu Pro Ser Gln Lys Trp Ile Met Thr Ala Ala Lys Ser Gln Asp
            180                 185                 190
Tyr Lys Ile Glu Ile Tyr Ser Ser Asp Leu Lys Ser Trp Lys Leu
            195                 200                 205
Glu Ser Ala Phe Ala Asn Glu Gly Phe Leu Gly Tyr Gln Tyr Glu Cys
            210                 215                 220
Pro Gly Leu Ile Glu Val Pro Thr Glu Gln Asp Pro Ser Lys Ser Tyr
225                 230                 235                 240
Trp Val Met Phe Ile Ser Ile Asn Pro Gly Ala Pro Ala Gly Gly Ser
            245                 250                 255
Phe Asn Gln Tyr Phe Val Gly Ser Phe Asn Gly Thr His Phe Glu Ala
            260                 265                 270
Phe Asp Asn Gln Ser Arg Val Val Asp Phe Gly Lys Asp Tyr Tyr Ala
            275                 280                 285
Leu Gln Thr Phe Phe Asn Thr Asp Pro Thr Tyr Gly Ser Ala Leu Gly
            290                 295                 300
Ile Ala Trp Ala Ser Asn Trp Glu Tyr Ser Ala Phe Val Pro Thr Asn
305                 310                 315                 320
Pro Trp Arg Ser Ser Met Ser Leu Val Arg Lys Phe Ser Leu Asn Thr
            325                 330                 335
Glu Tyr Gln Ala Asn Pro Glu Thr Glu Leu Ile Asn Leu Lys Ala Glu
            340                 345                 350
Pro Ile Leu Asn Ile Ser Asn Ala Gly Pro Trp Ser Arg Phe Ala Thr
            355                 360                 365
Asn Thr Thr Leu Thr Lys Ala Asn Ser Tyr Asn Val Asp Leu Ser Asn
            370                 375                 380
Ser Thr Gly Thr Leu Glu Phe Glu Leu Val Tyr Ala Val Asn Thr Thr
385                 390                 395                 400
Gln Thr Ile Ser Lys Ser Val Phe Ala Asp Leu Ser Leu Trp Phe Lys
            405                 410                 415
Gly Leu Glu Asp Pro Glu Glu Tyr Leu Arg Met Gly Phe Glu Val Ser
            420                 425                 430
Ala Ser Ser Phe Phe Leu Asp Arg Gly Asn Ser Lys Val Lys Phe Val
            435                 440                 445
Lys Glu Asn Pro Tyr Phe Thr Asn Arg Met Ser Val Asn Gln Pro
            450                 455                 460
Phe Lys Ser Glu Asn Asp Leu Ser Tyr Tyr Lys Val Tyr Gly Leu Leu
465                 470                 475                 480
Asp Gln Asn Ile Leu Glu Leu Tyr Phe Asn Asp Gly Asp Val Val Ser
            485                 490                 495
Thr Asn Thr Tyr Phe Met Thr Gly Asn Ala Leu Gly Ser Val Asn
            500                 505                 510
Met Thr Thr Gly Val Asp Asn Leu Phe Tyr Ile Asp Lys Phe Gln Val
            515                 520                 525
```

-continued

Arg Glu Val Lys
    530

<210> SEQ ID NO 54
<211> LENGTH: 1302
<212> TYPE: DNA
<213> ORGANISM: Corynebacterium glutamicum

<400> SEQUENCE: 54

| | |
|---|---:|
| gtgtgtgggg ctatgcacac agaactttcc agtttgcgcc ctgcgtacca tgtgactcct | 60 |
| ccgcagggca ggctcaatga tcccaacgga atgtacgtcg atggcgatac cctccacgtc | 120 |
| tactaccagc acgatccagg tttccccttc gcaccaaagc gcaccggctg gctcacacc | 180 |
| accacgccgt tgaccggacc gcagcgattg cagtggacgc acctgcccga cgctctttac | 240 |
| ccggatgcat cctatgacct ggatggatgc tattccggtg gagccgtatt tactgacggc | 300 |
| acacttaaac ttttctacac cggcaaccta aaaattgacg gcaagcgccg cgccacccaa | 360 |
| aacctcgtcg aagtcgagga cccaactggg ctgatgggcg gcattcatcg ccgttcgcct | 420 |
| aaaaatccgc ttatcgacgg acccgccagc ggtttcacac cccattaccg cgatcccatg | 480 |
| atcagccctg atggtgatgg ttggaaaatg gttcttgggg cccaacgcga aaacctcacc | 540 |
| ggtgcagcgg ttctataccg ctcgacagat cttgaaaact gggaattctc cggtgaaatc | 600 |
| acctttgacc tcagtgatgc acaacctggt tctgctcctg atctcgttcc cggtggctac | 660 |
| atgtgggaat gccccaacct ttttacgctt cgcgatgaag aaactggcga agatctcgac | 720 |
| gtgctgattt tctgtccaca aggattggac cgaatccacg atgaggttac tcactacgca | 780 |
| agctctgacc agtgcggata tgtcgtcggc aagcttgaag aacgaccttt ccgcgtcttg | 840 |
| cgaggattca gcgagctgga tttcggccat gaattctacg caccgcaggt tgcagtaaac | 900 |
| ggttctgatg cctggctcgt gggctggatg gggctgcccg cgcaggatga tcacccaaca | 960 |
| gttgcacggg aaggatgggt gcactgcctg actgtgcccc gcaagcttca tttgcgcaac | 1020 |
| cacgcgatct atcaagagct tcttctccca gaggggagt caggggtaat cagatctgta | 1080 |
| ttaggttctg aacctgtccg agtagacatc cgaggcaata tttccctcga gtgggatggt | 1140 |
| gtccgttttgt ctgtggatcg tggtggtgat cgtcgcgtag ctgaggtaaa acctggcgaa | 1200 |
| ttagtgatcg cggacgataa tacagccatt gagataactg caggtgatgg acaggtttca | 1260 |
| ttcgctttcc gggctttcaa aggtgacact attgagagat aa | 1302 |

<210> SEQ ID NO 55
<211> LENGTH: 433
<212> TYPE: PRT
<213> ORGANISM: Corynebacterium glutamicum

<400> SEQUENCE: 55

Met Cys Gly Ala Met His Thr Glu Leu Ser Ser Leu Arg Pro Ala Tyr
1               5                   10                  15

His Val Thr Pro Pro Gln Gly Arg Leu Asn Asp Pro Asn Gly Met Tyr
            20                  25                  30

Val Asp Gly Asp Thr Leu His Val Tyr Tyr Gln His Asp Pro Gly Phe
        35                  40                  45

Pro Phe Ala Pro Lys Arg Thr Gly Trp Ala His Thr Thr Thr Pro Leu
    50                  55                  60

Thr Gly Pro Gln Arg Leu Gln Trp Thr His Leu Pro Asp Ala Leu Tyr
65                  70                  75                  80

Pro Asp Ala Ser Tyr Asp Leu Asp Gly Cys Tyr Ser Gly Gly Ala Val
                85                  90                  95

```
Phe Thr Asp Gly Thr Leu Lys Leu Phe Tyr Thr Gly Asn Leu Lys Ile
            100                 105                 110
Asp Gly Lys Arg Arg Ala Thr Gln Asn Leu Val Glu Val Glu Asp Pro
            115                 120                 125
Thr Gly Leu Met Gly Gly Ile His Arg Arg Ser Pro Lys Asn Pro Leu
        130                 135                 140
Ile Asp Gly Pro Ala Ser Gly Phe Thr Pro His Tyr Arg Asp Pro Met
145                 150                 155                 160
Ile Ser Pro Asp Gly Asp Gly Trp Lys Met Val Leu Gly Ala Gln Arg
                165                 170                 175
Glu Asn Leu Thr Gly Ala Ala Val Leu Tyr Arg Ser Thr Asp Leu Glu
            180                 185                 190
Asn Trp Glu Phe Ser Gly Glu Ile Thr Phe Asp Leu Ser Asp Ala Gln
        195                 200                 205
Pro Gly Ser Ala Pro Asp Leu Val Pro Gly Gly Tyr Met Trp Glu Cys
    210                 215                 220
Pro Asn Leu Phe Thr Leu Arg Asp Glu Glu Thr Gly Glu Asp Leu Asp
225                 230                 235                 240
Val Leu Ile Phe Cys Pro Gln Gly Leu Asp Arg Ile His Asp Glu Val
                245                 250                 255
Thr His Tyr Ala Ser Ser Asp Gln Cys Gly Tyr Val Val Gly Lys Leu
            260                 265                 270
Glu Gly Thr Thr Phe Arg Val Leu Arg Gly Phe Ser Glu Leu Asp Phe
        275                 280                 285
Gly His Glu Phe Tyr Ala Pro Gln Val Ala Val Asn Gly Ser Asp Ala
    290                 295                 300
Trp Leu Val Gly Trp Met Gly Leu Pro Ala Gln Asp Asp His Pro Thr
305                 310                 315                 320
Val Ala Arg Glu Gly Trp Val His Cys Leu Thr Val Pro Arg Lys Leu
                325                 330                 335
His Leu Arg Asn His Ala Ile Tyr Gln Glu Leu Leu Leu Pro Glu Gly
            340                 345                 350
Glu Ser Gly Val Ile Arg Ser Val Leu Gly Ser Glu Pro Val Arg Val
        355                 360                 365
Asp Ile Arg Gly Asn Ile Ser Leu Glu Trp Asp Gly Val Arg Leu Ser
    370                 375                 380
Val Asp Arg Gly Gly Asp Arg Arg Val Ala Glu Val Lys Pro Gly Glu
385                 390                 395                 400
Leu Val Ile Ala Asp Asp Asn Thr Ala Ile Glu Ile Thr Ala Gly Asp
                405                 410                 415
Gly Gln Val Ser Phe Ala Phe Arg Ala Phe Lys Gly Asp Thr Ile Glu
            420                 425                 430
Arg

<210> SEQ ID NO 56
<211> LENGTH: 1473
<212> TYPE: DNA
<213> ORGANISM: Leuconostoc mesenteroides

<400> SEQUENCE: 56
atggaaattc aaaacaaagc aatgttgatc acttatgctg attcgttggg caaaaactta      60
aaagatgttc atcaagtctt gaaagaagat attggagatg cgattggtgg ggttcatttg     120
ttgcctttct tcccttcaac aggtgatcgc ggttttgcgc agccgattac tactcgtgtt     180
```

-continued

```
gatgccgcat ttggtgattg ggcagatgtc gaagcattgg gtgaagaata ctatttgatg      240
tttgacttca tgattaacca tatttctcgt gaatcagtga tgtatcaaga ttttaagaag      300
aatcatgacg attcaaagta taaagatttc tttattcgtt gggaaaagtt ctgggcaaag      360
gccggcgaaa accgtccaac acaagccgat gttgacttaa tttacaagcg taaagataag      420
gcaccaacgc aagaaatcac ttttgatgat ggcacaacag aaaacttgtg gaatactttt      480
ggtgaagaac aaattgacat tgatgttaat tcagccattg ccaaggaatt tattaagaca      540
acccttgaag acatggtaaa acatggtgct aacttgattc gtttggatgc ctttgcgtat      600
gcagttaaaa aagttgacac aaatgacttc ttcgttgagc agaaatctg ggacactttg      660
aatgaagtac gtgaaatttt gacaccatta aaggctgaaa ttttaccaga aattcatgaa      720
cattactcaa tccctaaaaa gatcaatgat catggttact tcacctatga ctttgcatta      780
ccaatgacaa cgctttacac attgtattca ggtaagacaa atcaattggc aaagtggttg      840
aagatgtcac caatgaagca attcacaaca ttggacacgc atgatggtat tggtgtcgtt      900
gatgcccgtg atattctaac tgatgatgaa attgactacg cttctgaaca actttacaag      960
gttggcgcga atgtcaaaaa gacatattca tctgcttcat acaacaacct tgatatttac     1020
caaattaact caacttatta ttcagcattg ggaaatgatg atgcagcata cttgttgagt     1080
cgtgtcttcc aagtctttgc gcctggaatt ccacaaattt attacgttgg tttgttggca     1140
ggtgaaaacg atatcgcgct tttggagtca actaaagaag gtcgtaatat taaccgtcat     1200
tactatacgc gtgaagaagt taagtcagaa gttaagcgac cagttgttgc taacttattg     1260
aagctattgt catggcgtaa tgaaagccct gcatttgatt tggctggctc aatcacagtt     1320
gacacgccaa ctgatacaac aattgtggtg acacgtcaag atgaaaatgg tcaaaacaaa     1380
gctgtattaa cagccgatgc ggccaacaaa acttttgaaa tcgttgagaa tggtcaaact     1440
gttatgagca gtgataattt gactcagaac taa                                  1473
```

<210> SEQ ID NO 57
<211> LENGTH: 490
<212> TYPE: PRT
<213> ORGANISM: Leuconostoc mesenteroides

<400> SEQUENCE: 57

```
Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
```

```
            145                 150                 155                 160
Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415

Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445

Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn
                485                 490

<210> SEQ ID NO 58
<211> LENGTH: 1515
<212> TYPE: DNA
<213> ORGANISM: Bifidobacterium adolescentis

<400> SEQUENCE: 58
atgaaaaaca aggtgcagct catcacttac gccgaccgcc ttggcgacgg caccatcaag      60
tcgatgaccg acattctgcg cacccgcttc gacggcgtgt acgacggcgt tcacatcctg     120
ccgttcttca ccccgttcga cggcgccgac gcaggcttcg acccgatcga ccacaccaag     180
gtcgacgaac gtctcggcag ctgggacgac gtcgccgaac tctccaagac ccacaacatc     240
```

```
atggtcgacg ccatcgtcaa ccacatgagt tgggaatcca agcagttcca ggacgtgctg      300
gccaagggcg aggagtccga atactatccg atgttcctca ccatgagctc cgtgttcccg      360
aacggcgcca ccgaagagga cctggccggc atctaccgtc cgcgtccggg cctgccgttc      420
acccactaca agttcgccgg caagacccgc ctcgtgtggg tcagcttcac cccgcagcag      480
gtggacatcg acaccgattc cgacaagggt tgggaatacc tcatgtcgat tttcgaccag      540
atggccgcct ctcacgtcag ctacatccgc ctcgacgccg tcggctatgg cgccaaggaa      600
gccggcacca gctgcttcat gacccccgaag accttcaagc tgatctcccg tctgcgtgag      660
```
(Note: line at 660 "gacccccgaag" - reading as shown)

```
gaaggcgtca agcgcggtct ggaaatcctc atcgaagtgc actcctacta caagaagcag      720
gtcgaaatcg catccaaggt ggaccgcgtc tacgacttcg ccctgcctcc gctgctgctg      780
cacgcgctga gcaccggcca cgtcgagccc gtcgcccact ggaccgacat acgcccgaac      840
aacgccgtca ccgtgctcga tacgcacgac ggcatcggcg tgatcgacat cggctccgac      900
cagctcgacc gctcgctcaa gggtctcgtg ccggatgagg acgtggacaa cctcgtcaac      960
accatccacg ccaacaccca cggcgaatcc caggcagcca ctggcgccgc cgcatccaat     1020
ctcgacctct accaggtcaa cagcacctac tattcggcgc tcgggtgcaa cgaccagcac     1080
tacatcgccg cccgcgcggt gcagttcttc ctgccgggcg tgccgcaagt ctactacgtc     1140
ggcgcgctcg ccggcaagaa cgacatggag ctgctgcgta agacgaataa cggccgcgac     1200
atcaatcgcc attactactc caccgcggaa atcgacgaga acctcaagcg tccggtcgtc     1260
aaggccctga cgcgctcgc caagttccgc aacgagctcg acgcgttcga cggcacgttc     1320
tcgtacacca ccgatgacga cacgtccatc agcttcacct ggcgcggcga aaccagccag     1380
gccacgctga cgttcgagcc gaagcgcggt ctcggtgtgg acaacactac gccggtcgcc     1440
atgttggaat gggaggattc cgcgggagac caccgttcgg atgatctgat cgccaatccg     1500
cctgtcgtcg cctga                                                      1515
```

<210> SEQ ID NO 59
<211> LENGTH: 504
<212> TYPE: PRT
<213> ORGANISM: Bifidobacterium adolescentis

<400> SEQUENCE: 59

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140
```

```
Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
            165                 170                 175

Ile Phe Asp Gln Met Ala Ala Ser His Val Ser Tyr Ile Arg Leu Asp
        180                 185                 190

Ala Val Gly Tyr Gly Ala Lys Glu Ala Gly Thr Ser Cys Phe Met Thr
    195                 200                 205

Pro Lys Thr Phe Lys Leu Ile Ser Arg Leu Arg Glu Glu Gly Val Lys
210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
            245                 250                 255

Pro Leu Leu Leu His Ala Leu Ser Thr Gly His Val Glu Pro Val Ala
        260                 265                 270

His Trp Thr Asp Ile Arg Pro Asn Asn Ala Val Thr Val Leu Asp Thr
    275                 280                 285

His Asp Gly Ile Gly Val Ile Asp Ile Gly Ser Asp Gln Leu Asp Arg
290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
            325                 330                 335

Ala Ala Ser Asn Leu Asp Leu Tyr Gln Val Asn Ser Thr Tyr Tyr Ser
        340                 345                 350

Ala Leu Gly Cys Asn Asp Gln His Tyr Ile Ala Ala Arg Ala Val Gln
    355                 360                 365

Phe Phe Leu Pro Gly Val Pro Gln Val Tyr Tyr Val Gly Ala Leu Ala
370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
            405                 410                 415

Arg Pro Val Val Lys Ala Leu Asn Ala Leu Ala Lys Phe Arg Asn Glu
        420                 425                 430

Leu Asp Ala Phe Asp Gly Thr Phe Ser Tyr Thr Thr Asp Asp Asp Thr
    435                 440                 445

Ser Ile Ser Phe Thr Trp Arg Gly Glu Thr Ser Gln Ala Thr Leu Thr
450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
            485                 490                 495

Ile Ala Asn Pro Pro Val Val Ala
        500

<210> SEQ ID NO 60
<211> LENGTH: 927
<212> TYPE: DNA
<213> ORGANISM: Agrobacterium tumefaciens

<400> SEQUENCE: 60
atgatcctgt gttgtggtga agccctgatc gacatgctgc cccggcagac gacgctgggt     60
gaggcgggct ttgccccctta cgcaggcgga gcggtcttca acacggcaat tgcgctgggg    120
```

```
cgtcttggcg tcccttcagc cttttttacc ggtctttccg acgacatgat gggcgatatc    180
ctgcgggaga ccctgcgggc cagcaaggtg gatttcagct attgcgccac cctgtcgcgc    240
cccaccacca ttgcgttcgt taagctggtt gatggccatg cgacctacgc tttttacgac    300
gagaacaccg ccggccggat gatcaccgag gccgaacttc cggccttggg agcggattgc    360
gaagcgctgc atttcggcgc catcagcctt attcccgaac cctgcggcag cacctatgag    420
gcgctgatga cgcgcgagca tgagacccgc gtcatctcgc tcgatccgaa cattcgtccc    480
ggcttcatcc agaacaagca gtcgcacatg gcccgcatcc gccgcatggc ggcgatgtct    540
gacatcgtca agttctcgga tgaggacctg gcgtggttcg gtctggaagg cgacgaggac    600
acgcttgccc gccactggct gcaccacggt gcaaaactcg tcgttgtcac ccgtggcgcc    660
aagggtgccg tgggttacag cgccaatctc aaggtggaag tggcctccga gcgcgtcgaa    720
gtggtcgata cggtcggcgc cggcgatacg ttcgatgccg gcattcttgc ttcgctgaaa    780
atgcagggcc tgctgaccaa agcgcaggtg gcttcgctga cgaagagca gatcagaaaa    840 gctttggcgc ttggcgcgaa agccgctgcg gtcactgtct cgcgggctgg cgcaaatccg    900
cctttcgcgc atgaaatcgg tttgtga                                      927
```

<210> SEQ ID NO 61  
<211> LENGTH: 308  
<212> TYPE: PRT  
<213> ORGANISM: Agrobacterium tumefaciens

<400> SEQUENCE: 61

```
Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
            20                  25                  30

Phe Asn Thr Ala Ile Ala Leu Gly Arg Leu Gly Val Pro Ser Ala Phe
        35                  40                  45

Phe Thr Gly Leu Ser Asp Asp Met Met Gly Asp Ile Leu Arg Glu Thr
    50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110

Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
                165                 170                 175

Ala Ala Met Ser Asp Ile Val Lys Phe Ser Asp Glu Asp Leu Ala Trp
            180                 185                 190

Phe Gly Leu Glu Gly Asp Glu Asp Thr Leu Ala Arg His Trp Leu His
        195                 200                 205

His Gly Ala Lys Leu Val Val Val Thr Arg Gly Ala Lys Gly Ala Val
    210                 215                 220

Gly Tyr Ser Ala Asn Leu Lys Val Glu Val Ala Ser Glu Arg Val Glu
```

```
                   225                 230                 235                 240
Val Val Asp Thr Val Gly Ala Gly Asp Thr Phe Asp Ala Gly Ile Leu
                245                 250                 255
Ala Ser Leu Lys Met Gln Gly Leu Leu Thr Lys Ala Gln Val Ala Ser
                260                 265                 270
Leu Ser Glu Glu Gln Ile Arg Lys Ala Leu Ala Leu Gly Ala Lys Ala
                275                 280                 285
Ala Ala Val Thr Val Ser Arg Ala Gly Ala Asn Pro Pro Phe Ala His
                290                 295                 300
Glu Ile Gly Leu
305

<210> SEQ ID NO 62
<211> LENGTH: 1404
<212> TYPE: DNA
<213> ORGANISM: Streptococcus mutans

<400> SEQUENCE: 62
cagctgatta tgcgtcagtt gaaaccctcg cttcttcagg aactgttgct gtaggtgata      60
gcttacttga agttaaaaaa taagaaatat tatcagaaag accgtaaggt cttttttgact    120 gcttaaaaga ttcagtaaca atagtattaa agccttttgg ctaactaata cttgaaattt    180
agcaaattat gatataatgt taagtagtcc ttaagggtag attaagggta ttcaaatcca    240
aaaattgatt tggtaagtta agtaaaatat aagaggttta ttatgtctaa attatatggc    300
agcatcgaag ctggcggaac aaaatttgtc tgtgctgtag gtgatgaaaa ttttcaaatt    360
ttagaaaaag ttcagttccc aacaacaaca ccttatgaaa caatagaaaa aacagttgct    420 ttcttttaaaa aatttgaagc tgatttagcc agtgttgcca ttggttcttt tggccctatt    480
gatattgatc aaaattcaga cacttatggt tacattactt caacaccaaa gccaaactgg    540
gctaacgttg attttgtcgg cttaatttct aaagatttta aaattccatt ttactttacg    600
acagatgtta attcttctgc ttatggggaa acaattgctc gttcaaatgt taaaagtctg    660
gtttattata ctattggaac aggcattgga gcaggggcta ttcaaaatgg cgaattcatt    720
ggcggtatgg gacatacgga agctggacac gtttacatgg ctccgcatcc caatgatgtt    780
catcatggtt ttgtaggcac ctgtcctttc cataaaggct gtttagaagg acttgcagcg    840
ggtcctagct tagaggctcg tactggtatt cgtggtgagt taattgagca aaactcagaa    900
gtttgggata ttcaggcata ctacattgct caggcggcta ttcaagcgac tgtccttttat    960 cgtccgcaag tcattgtatt tggcggaggc gttatggcac aagaacatat gctcaatcgg   1020
gttcgtgaaa aatttacttc acttttgaat gactatcttc cagttccaga tgttaaagat   1080
tatattgtga caccagctgt tgcagaaaat ggttcagcaa cattgggaaa tctcgcttta   1140
gctaaaaaga tagcagcgcg ttaattaaaa atgaattgga agattaaagc accttctaat   1200
attcaatatt aaactgttag aatttacgtg aacgaaattt tcattttatg aggataatga   1260
agtgaatata attactcttg atttcctctg aaactagata gtggtatatt gaaaaacaga   1320
aaggagaaca ctatggaagg acctttgttt ttacaatcac aaatgcataa aaaaatctgg   1380
ggcggcaatc ggctcagaaa agaa                                           1404

<210> SEQ ID NO 63
<211> LENGTH: 293
<212> TYPE: PRT
<213> ORGANISM: Streptococcus mutans

<400> SEQUENCE: 63
```

| | | | | | | | | | | | | | | |
|---|---|---|---|---|---|---|---|---|---|---|---|---|---|---|
| Met | Ser | Lys | Leu | Tyr | Gly | Ser | Ile | Glu | Ala | Gly | Gly | Thr | Lys | Phe | Val |
| 1 | | | | 5 | | | | | 10 | | | | | 15 |
| Cys | Ala | Val | Gly | Asp | Glu | Asn | Phe | Gln | Ile | Leu | Glu | Lys | Val | Gln | Phe |
| | | | 20 | | | | | 25 | | | | | 30 | |
| Pro | Thr | Thr | Thr | Pro | Tyr | Glu | Thr | Ile | Glu | Lys | Thr | Val | Ala | Phe | Phe |
| | | 35 | | | | | 40 | | | | | 45 | | |
| Lys | Lys | Phe | Glu | Ala | Asp | Leu | Ala | Ser | Val | Ala | Ile | Gly | Ser | Phe | Gly |
| | 50 | | | | | 55 | | | | | 60 | | | | |
| Pro | Ile | Asp | Ile | Asp | Gln | Asn | Ser | Asp | Thr | Tyr | Gly | Tyr | Ile | Thr | Ser |
| 65 | | | | | 70 | | | | | 75 | | | | | 80 |
| Thr | Pro | Lys | Pro | Asn | Trp | Ala | Asn | Val | Asp | Phe | Val | Gly | Leu | Ile | Ser |
| | | | | 85 | | | | | 90 | | | | | 95 | |
| Lys | Asp | Phe | Lys | Ile | Pro | Phe | Tyr | Phe | Thr | Thr | Asp | Val | Asn | Ser | Ser |
| | | | 100 | | | | | 105 | | | | | 110 | | |
| Ala | Tyr | Gly | Glu | Thr | Ile | Ala | Arg | Ser | Asn | Val | Lys | Ser | Leu | Val | Tyr |
| | | 115 | | | | | 120 | | | | | 125 | | | |
| Tyr | Thr | Ile | Gly | Thr | Gly | Ile | Gly | Ala | Gly | Ala | Ile | Gln | Asn | Gly | Glu |
| | 130 | | | | | 135 | | | | | 140 | | | | |
| Phe | Ile | Gly | Gly | Met | Gly | His | Thr | Glu | Ala | Gly | His | Val | Tyr | Met | Ala |
| 145 | | | | | 150 | | | | | 155 | | | | | 160 |
| Pro | His | Pro | Asn | Asp | Val | His | His | Gly | Phe | Val | Gly | Thr | Cys | Pro | Phe |
| | | | | 165 | | | | | 170 | | | | | 175 | |
| His | Lys | Gly | Cys | Leu | Glu | Gly | Leu | Ala | Ala | Gly | Pro | Ser | Leu | Glu | Ala |
| | | | 180 | | | | | 185 | | | | | 190 | | |
| Arg | Thr | Gly | Ile | Arg | Gly | Glu | Leu | Ile | Glu | Gln | Asn | Ser | Glu | Val | Trp |
| | | 195 | | | | | 200 | | | | | 205 | | | |
| Asp | Ile | Gln | Ala | Tyr | Tyr | Ile | Ala | Gln | Ala | Ala | Ile | Gln | Ala | Thr | Val |
| | 210 | | | | | 215 | | | | | 220 | | | | |
| Leu | Tyr | Arg | Pro | Gln | Val | Ile | Val | Phe | Gly | Gly | Val | Met | Ala | Gln |
| 225 | | | | | 230 | | | | | 235 | | | | | 240 |
| Glu | His | Met | Leu | Asn | Arg | Val | Arg | Glu | Lys | Phe | Thr | Ser | Leu | Leu | Asn |
| | | | | 245 | | | | | 250 | | | | | 255 | |
| Asp | Tyr | Leu | Pro | Val | Pro | Asp | Val | Lys | Asp | Tyr | Ile | Val | Thr | Pro | Ala |
| | | | 260 | | | | | 265 | | | | | 270 | | |
| Val | Ala | Glu | Asn | Gly | Ser | Ala | Thr | Leu | Gly | Asn | Leu | Ala | Leu | Ala | Lys |
| | | 275 | | | | | 280 | | | | | 285 | | | |
| Lys | Ile | Ala | Ala | Arg |
| | 290 | | | |

<210> SEQ ID NO 64
<211> LENGTH: 915
<212> TYPE: DNA
<213> ORGANISM: Escherichia coli

<400> SEQUENCE: 64

| | | | | | |
|---|---|---|---|---|---|
| atgtcagcca | aagtatgggt | tttaggggat | gcggtcgtag | atctcttgcc | agaatcagac | 60 |
| gggcgcctac | tgccttgtcc | tggcggcgcg | ccagctaacg | ttgcggtggg | aatcgccaga | 120 |
| ttaggcggaa | caagtgggtt | tataggtcgg | gtggggatg | atccttttgg | tgcgttaatg | 180 |
| caaagaacgc | tgctaactga | gggagtcgat | atcacgtatc | tgaagcaaga | tgaatggcac | 240 |
| cggacatcca | cggtgcttgt | cgatctgaac | gatcaagggg | aacgttcatt | tacgtttatg | 300 |
| gtccgcccca | gtgccgatct | tttttagag | acgacagact | tgccctgctg | gcacatggc | 360 |
| gaatggttac | atctctgttc | aattgcgttg | tctgccgagc | cttcgcgtac | cagcgcattt | 420 |

```
actgcgatga cggcgatccg gcatgccgga ggttttgtca gcttcgatcc taatattcgt    480
gaagatctat ggcaagacga gcatttgctc cgcttgtgtt tgcggcaggc gctacaactg    540
gcggatgtcg tcaagctctc ggaagaagaa tggcgactta tcagtggaaa acacagaac     600 gatcaggata tatgcgccct ggcaaaagag tatgagatcg ccatgctgtt ggtgactaaa    660
ggtgcagaag gggtggtggt ctgttatcga ggacaagttc accattttgc tggaatgtct    720
gtgaattgtg tcgatagcac ggggcggga gatgcgttcg ttgccgggtt actcacaggt     780
ctgtcctcta cgggattatc tacagatgag agagaaatgc gacgaattat cgatctcgct    840
caacgttgcg gagcgcttgc agtaacggcg aaggggcaa tgacagcgct gccatgtcga     900
caagaactgg aatag                                                     915
```

<210> SEQ ID NO 65
<211> LENGTH: 304
<212> TYPE: PRT
<213> ORGANISM: Escherichia coli

<400> SEQUENCE: 65

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Gln Asp Ile Cys Ala Leu Ala
    195                 200                 205

Lys Glu Tyr Glu Ile Ala Met Leu Leu Val Thr Lys Gly Ala Glu Gly
        210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285
```

```
Thr Ala Lys Gly Ala Met Thr Ala Leu Pro Cys Arg Gln Glu Leu Glu
        290                 295                 300
```

<210> SEQ ID NO 66
<211> LENGTH: 924
<212> TYPE: DNA
<213> ORGANISM: Klebsiella pneumoniae

<400> SEQUENCE: 66

```
atgaatggaa aaatctgggt actcggcgat gcggtcgtcg atctcctgcc cgatggagag    60
ggccgcctgc tgcaatgccc cggcggcgcg ccggccaacg tggcggtcgg cgtggcgcgg   120
ctcggcggtg acagcgggtt tatcggccgc gtcggcgaca tcccttcgg ccgttttatg    180
cgtcacaccc tggcgcagga gcaagtggat gtgaactata tgcgcctcga tgcggcgcag   240
cgcacctcca cggtggtggt cgatctcgat agccacgggg agcgcacctt taccttttatg  300
gtccgtccga cgccgacct gttccttcag cccgaggatc tcccgccgtt tgccgccggt    360
cagtggctgc acgtctgctc catcgctctc agcgcggagc cgagccgcag cacgacattc   420
gcggcgatgg aggcgataaa gcgcgccggg ggctatgtca gcttcgaccc caatatccgc   480
agcgacctgt ggcaggatcc gcaggacctt cgcgactgtc tcgaccgggc gctggccctc   540
gccgacgcca taaaactttc ggaagaggag ctggcgttta tcagcggcag cgacgacatc   600
gtcagcggca cgcccggct gaacgcccgc ttccagccga cgctactgct ggtgacccag   660
ggtaaagcgg gggtccaggc cgcccctgcgc gggcaggtta gccacttccc tgcccgcccg   720
gtggtggccc tcgataccac cggcgccggc gatgcctttg tcgccgggct actcgccggc   780
ctcgccgccc acggtatccc ggacaacctc gcagccctgg ctcccgacct cgcgctggcg   840
caaacctgcg cgcccctggc caccaccgcc aaaggcgcca tgaccgccct gccctacagg   900
gacgatcttc agcgctcgct gtga                                          924
```

<210> SEQ ID NO 67
<211> LENGTH: 307
<212> TYPE: PRT
<213> ORGANISM: Klebsiella pneumoniae

<400> SEQUENCE: 67

```
Met Asn Gly Lys Ile Trp Val Leu Gly Asp Ala Val Val Asp Leu Leu
1               5                   10                  15

Pro Asp Gly Glu Gly Arg Leu Leu Gln Cys Pro Gly Gly Ala Pro Ala
            20                  25                  30

Asn Val Ala Val Gly Val Ala Arg Leu Gly Gly Asp Ser Gly Phe Ile
        35                  40                  45

Gly Arg Val Gly Asp Asp Pro Phe Gly Arg Phe Met Arg His Thr Leu
    50                  55                  60

Ala Gln Glu Gln Val Asp Val Asn Tyr Met Arg Leu Asp Ala Ala Gln
65                  70                  75                  80

Arg Thr Ser Thr Val Val Asp Leu Asp Ser His Gly Glu Arg Thr
                85                  90                  95

Phe Thr Phe Met Val Arg Pro Ser Ala Asp Leu Phe Leu Gln Pro Glu
                100                 105                 110

Asp Leu Pro Pro Phe Ala Ala Gly Gln Trp Leu His Val Cys Ser Ile
            115                 120                 125

Ala Leu Ser Ala Glu Pro Ser Arg Ser Thr Thr Phe Ala Ala Met Glu
130                 135                 140

Ala Ile Lys Arg Ala Gly Gly Tyr Val Ser Phe Asp Pro Asn Ile Arg
145                 150                 155                 160
```

Ser Asp Leu Trp Gln Asp Pro Gln Asp Leu Arg Asp Cys Leu Asp Arg
            165                 170                 175

Ala Leu Ala Leu Ala Asp Ala Ile Lys Leu Ser Glu Glu Glu Leu Ala
        180                 185                 190

Phe Ile Ser Gly Ser Asp Asp Ile Val Ser Gly Thr Ala Arg Leu Asn
    195                 200                 205

Ala Arg Phe Gln Pro Thr Leu Leu Val Thr Gln Gly Lys Ala Gly
210                 215                 220

Val Gln Ala Ala Leu Arg Gly Gln Val Ser His Phe Pro Ala Arg Pro
225                 230                 235                 240

Val Val Ala Val Asp Thr Thr Gly Ala Gly Asp Ala Phe Val Ala Gly
                245                 250                 255

Leu Leu Ala Gly Leu Ala Ala His Gly Ile Pro Asp Asn Leu Ala Ala
            260                 265                 270

Leu Ala Pro Asp Leu Ala Leu Ala Gln Thr Cys Gly Ala Leu Ala Thr
        275                 280                 285

Thr Ala Lys Gly Ala Met Thr Ala Leu Pro Tyr Arg Asp Asp Leu Gln
    290                 295                 300

Arg Ser Leu
305

<210> SEQ ID NO 68
<211> LENGTH: 915
<212> TYPE: DNA
<213> ORGANISM: Escherichia coli

<400> SEQUENCE: 68
atgtcagcca aagtatgggt tttaggggat gcggtcgtag atctcttgcc agaatcagac        60
gggcgcctac tgccttgtcc tggcggcgcg ccagctaacg ttgcggtggg aatcgccaga       120
ttaggcggaa caagtgggtt tataggtcgg gtggggatg atccttttgg tgcgttaatg        180
caaagaacgc tgctaactga gggagtcgat atcacgtatc tgaagcaaga tgaatggcac       240
cggacatcca cggtgcttgt cgatctgaac gatcaagggg aacgttcatt tacgtttatg       300
gtccgcccca gtgccgatct ttttttagag acgacagact tgccctgctg gcgacatggc       360
gaatggttac atctctgttc aattgcgttg tctgccgagc cttcgcgtac cagcgcattt       420
actgcgatga cggcgatccg gcatgccgga ggttttgtca gcttcgatcc taatattcgt       480
gaagatctat ggcaagacga gcatttgctc cgcttgtgtt tgcggcaggc gctacaactg       540
gcggatgtcg tcaagctctc ggaagaagaa tggcgactta tcagtggaaa acacagaac       600 gatcaggata tatgcgccct ggcaaaagag tatgagatcg ccatgctgtt ggtgactaaa       660
ggtgcagaag gggtggtggt ctgttatcga ggacaagttc accattttgc tggaatgtct       720
gtgaattgtg tcgatagcac ggggcggga gatgcgttcg ttgccgggtt actcacaggt       780
ctgtcctcta cgggattatc tacagatgag agagaaatgc gacgaattat cgatctcgct       840
caacgttgcg gagcgcttgc agtaacggcg aaagggcaa tgacagcgct gccatgtcga       900
caagaactgg aatag                                                       915

<210> SEQ ID NO 69
<211> LENGTH: 304
<212> TYPE: PRT
<213> ORGANISM: Escherichia coli

<400> SEQUENCE: 69

Met Ser Ala Lys Val Trp Val Leu Gly Asp Ala Val Val Asp Leu Leu

```
                 1               5                  10                 15
Pro Glu Ser Asp Gly Arg Leu Leu Pro Cys Pro Gly Gly Ala Pro Ala
            20                  25                 30

Asn Val Ala Val Gly Ile Ala Arg Leu Gly Gly Thr Ser Gly Phe Ile
            35                  40                 45

Gly Arg Val Gly Asp Asp Pro Phe Gly Ala Leu Met Gln Arg Thr Leu
 50                  55                  60

Leu Thr Glu Gly Val Asp Ile Thr Tyr Leu Lys Gln Asp Glu Trp His
 65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
                100                 105                110

Asp Leu Pro Cys Trp Arg His Gly Glu Trp Leu His Leu Cys Ser Ile
            115                 120                125

Ala Leu Ser Ala Glu Pro Ser Arg Thr Ser Ala Phe Thr Ala Met Thr
            130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Gln Asp Ile Cys Ala Leu Ala
            195                 200                 205

Lys Glu Tyr Glu Ile Ala Met Leu Leu Val Thr Lys Gly Ala Glu Gly
 210                215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
            245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
            290                 295                 300

<210> SEQ ID NO 70
<211> LENGTH: 879
<212> TYPE: DNA
<213> ORGANISM: Enterococcus faecalis

<400> SEQUENCE: 70
atgacagaaa aacttttagg aagtatcgaa gccggtggca caaaatttgt atgtggcgtt      60
gggacagatg atttgaccat cgtagaacgt gtcagttttc ccacaacaac cccagaagaa     120
acaatgaaaa agtaatagaa atttttccaa caatatcctt taaaagcgat tgggattggt     180
tcatttggtc cgattgatat tcacgttgat tctcctacgt atggttatat cacttctaca     240
ccaaaattag cttggcgtaa cttttgacttg ttaggaacta tgaaacaaca ttttgatgtg     300
ccaatggctt ggacaacgga tgtgaatgct gcggcatatg gtgagtatgt tgctggaaat     360
gggcaacata catctagttg tgtatattat acaattggaa ctggtgttgg cgctggagcg     420
attcaaaacg gtgagtttat tgaaggcttt agccacccag aaatggggca tgcgttagtt     480
```

-continued

```
cgtcgtcatc ctgaagatac gtatgcagga aattgtcctt atcatggaga ttgtttagaa      540
gggattgcag caggaccagc agttgaaggt cgttctggta aaaaaggaca tttattggaa      600
gaggatcata aaacttggga attagaagct tattatttag cgcaagcggc gtacaatacg      660
actttattat tagcgccaga agtgatcatt ttaggtggcg gcgtcatgaa acaacgtcat      720
ttgatgccga aagttcgtga aaaatttgct gaattagtca atggatatgt ggaaacaccg      780
cctttagaaa aatacttggt gacgcctctt ttagaagata atccaggaac aatcggttgc      840
tttgccttgg caaaaaaagc tttaatggct caaaaataa                             879
```

<210> SEQ ID NO 71
<211> LENGTH: 292
<212> TYPE: PRT
<213> ORGANISM: Enterococcus faecalis

<400> SEQUENCE: 71

```
Met Thr Glu Lys Leu Leu Gly Ser Ile Glu Ala Gly Gly Thr Lys Phe
  1               5                  10                  15

Val Cys Gly Val Gly Thr Asp Asp Leu Thr Ile Val Glu Arg Val Ser
                 20                  25                  30

Phe Pro Thr Thr Thr Pro Glu Glu Thr Met Lys Lys Val Ile Glu Phe
             35                  40                  45

Phe Gln Gln Tyr Pro Leu Lys Ala Ile Gly Ile Gly Ser Phe Gly Pro
         50                  55                  60

Ile Asp Ile His Val Asp Ser Pro Thr Tyr Gly Tyr Ile Thr Ser Thr
 65                  70                  75                  80

Pro Lys Leu Ala Trp Arg Asn Phe Asp Leu Leu Gly Thr Met Lys Gln
                 85                  90                  95

His Phe Asp Val Pro Met Ala Trp Thr Thr Asp Val Asn Ala Ala Ala
            100                 105                 110

Tyr Gly Glu Tyr Val Ala Gly Asn Gly Gln His Thr Ser Ser Cys Val
        115                 120                 125

Tyr Tyr Thr Ile Gly Thr Gly Val Gly Ala Gly Ala Ile Gln Asn Gly
    130                 135                 140

Glu Phe Ile Glu Gly Phe Ser His Pro Glu Met Gly His Ala Leu Val
145                 150                 155                 160

Arg Arg His Pro Glu Asp Thr Tyr Ala Gly Asn Cys Pro Tyr His Gly
                165                 170                 175

Asp Cys Leu Glu Gly Ile Ala Ala Gly Pro Ala Val Glu Gly Arg Ser
            180                 185                 190

Gly Lys Lys Gly His Leu Leu Glu Glu Asp His Lys Thr Trp Glu Leu
        195                 200                 205

Glu Ala Tyr Tyr Leu Ala Gln Ala Ala Tyr Asn Thr Thr Leu Leu Leu
    210                 215                 220

Ala Pro Glu Val Ile Ile Leu Gly Gly Gly Val Met Lys Gln Arg His
225                 230                 235                 240

Leu Met Pro Lys Val Arg Glu Lys Phe Ala Glu Leu Val Asn Gly Tyr
                245                 250                 255

Val Glu Thr Pro Pro Leu Glu Lys Tyr Leu Val Thr Pro Leu Leu Glu
            260                 265                 270

Asp Asn Pro Gly Thr Ile Gly Cys Phe Ala Leu Ala Lys Lys Ala Leu
        275                 280                 285

Met Ala Gln Lys
    290
```

<210> SEQ ID NO 72
<211> LENGTH: 1458
<212> TYPE: DNA
<213> ORGANISM: Saccharomyces cerevisiae

<400> SEQUENCE: 72

```
atggttcatt taggtccaaa gaaaccacag gctagaaagg gttccatggc tgatgtgccc      60
aaggaattga tggatgaaat tcatcagttg gaagatatgt ttacagttga cagcgagacc     120
ttgagaaagg ttgttaagca ctttatcgac gaattgaata aaggtttgac aaagaaggga     180
ggtaacattc caatgattcc cggttgggtc atggaattcc caacaggtaa agaatctggt     240
aactatttgg ccattgattt gggtggtact aacttaagag tcgtgttggt caagttgagc     300
ggtaaccata cctttgacac cactcaatcc aagtataaac taccacatga catgagaacc     360
actaagcacc aagaggagtt atggtccttt attgccgact ctttgaagga ctttatggtc     420
gagcaagaat tgctaaacac caaggacacc ttaccattag gtttcacctt ctcgtaccca     480
gcttcccaaa acaagattaa cgaaggtatt ttgcaaagat ggaccaaggg tttcgatatt     540
ccaaatgtcg aaggccacga tgtcgtccca ttgctacaaa cgaaatttc aagagagag      600
ttgcctattg aaattgtagc attgattaat gatactgttg gtactttaat tgcctcatac     660
tacactgacc cagagactaa gatgggtgtg attttcggta ctggtgtcaa cggtgctttc     720
tatgatgttg tttccgatat cgaaaagttg gagggcaaat tagcagacga tattccaagt     780
aactctccaa tggctatcaa ttgtgaatat ggttccttcg ataatgaaca tttggtcttg     840
ccaagaacca agtacgatgt tgctgtcgac gaacaatctc aagacctgg tcaacaagct     900
tttgaaaaga tgacctccgg ttactacttg ggtgaattgt tgcgtctagt gttacttgaa     960
ttaaacgaga agggcttgat gttgaaggat caagatctaa gcaagttgaa acaaccatac    1020
atcatggata cctcctaccc agcaagaatc gaggatgatc catttgaaaa cttggaagat    1080
actgatgaca tcttccaaaa ggactttggt gtcaagacca ctctgccaga acgtaagttg    1140
attagaagac tttgtgaatt gatcggtacc agagctgcta gattagctgt tgtggtatt    1200
gccgctattt gccaaaagag aggttacaag actggtcaca ttgccgctga cggttctgtc    1260
tataacaaat acccaggttt caaggaagcc gccgctaagg gtttgagaga tatctatgga    1320
tggactggtg acgcaagcaa agatccaatt acgattgttc cagctgagga tggttcaggt    1380
gcaggtgctg ctgttattgc tgcattgtcc gaaaaaagaa ttgccgaagg taagtctctt    1440
ggtatcattg gcgcttaa                                                 1458
```

<210> SEQ ID NO 73
<211> LENGTH: 485
<212> TYPE: PRT
<213> ORGANISM: Saccharomyces cerevisiae

<400> SEQUENCE: 73

```
Met Val His Leu Gly Pro Lys Lys Pro Gln Ala Arg Lys Gly Ser Met
  1               5                  10                  15

Ala Asp Val Pro Lys Glu Leu Met Asp Glu Ile His Gln Leu Glu Asp
                 20                  25                  30

Met Phe Thr Val Asp Ser Glu Thr Leu Arg Lys Val Val Lys His Phe
             35                  40                  45

Ile Asp Glu Leu Asn Lys Gly Leu Thr Lys Lys Gly Gly Asn Ile Pro
         50                  55                  60

Met Ile Pro Gly Trp Val Met Glu Phe Pro Thr Gly Lys Glu Ser Gly
 65                  70                  75                  80
```

```
Asn Tyr Leu Ala Ile Asp Leu Gly Gly Thr Asn Leu Arg Val Val Leu
                85                  90                  95
Val Lys Leu Ser Gly Asn His Thr Phe Asp Thr Thr Gln Ser Lys Tyr
            100                 105                 110
Lys Leu Pro His Asp Met Arg Thr Thr Lys His Gln Glu Glu Leu Trp
        115                 120                 125
Ser Phe Ile Ala Asp Ser Leu Lys Asp Phe Met Val Glu Gln Glu Leu
    130                 135                 140
Leu Asn Thr Lys Asp Thr Leu Pro Leu Gly Phe Thr Phe Ser Tyr Pro
145                 150                 155                 160
Ala Ser Gln Asn Lys Ile Asn Glu Gly Ile Leu Gln Arg Trp Thr Lys
                165                 170                 175
Gly Phe Asp Ile Pro Asn Val Glu Gly His Asp Val Val Pro Leu Leu
            180                 185                 190
Gln Asn Glu Ile Ser Lys Arg Glu Leu Pro Ile Glu Ile Val Ala Leu
        195                 200                 205
Ile Asn Asp Thr Val Gly Thr Leu Ile Ala Ser Tyr Tyr Thr Asp Pro
    210                 215                 220
Glu Thr Lys Met Gly Val Ile Phe Gly Thr Gly Val Asn Gly Ala Phe
225                 230                 235                 240
Tyr Asp Val Val Ser Asp Ile Glu Lys Leu Glu Gly Lys Leu Ala Asp
                245                 250                 255
Asp Ile Pro Ser Asn Ser Pro Met Ala Ile Asn Cys Glu Tyr Gly Ser
            260                 265                 270
Phe Asp Asn Glu His Leu Val Leu Pro Arg Thr Lys Tyr Asp Val Ala
        275                 280                 285
Val Asp Glu Gln Ser Pro Arg Pro Gly Gln Gln Ala Phe Glu Lys Met
    290                 295                 300
Thr Ser Gly Tyr Tyr Leu Gly Glu Leu Leu Arg Leu Val Leu Leu Glu
305                 310                 315                 320
Leu Asn Glu Lys Gly Leu Met Leu Lys Asp Gln Asp Leu Ser Lys Leu
                325                 330                 335
Lys Gln Pro Tyr Ile Met Asp Thr Ser Tyr Pro Ala Arg Ile Glu Asp
            340                 345                 350
Asp Pro Phe Glu Asn Leu Glu Asp Thr Asp Ile Phe Gln Lys Asp
        355                 360                 365
Phe Gly Val Lys Thr Thr Leu Pro Glu Arg Lys Leu Ile Arg Arg Leu
    370                 375                 380
Cys Glu Leu Ile Gly Thr Arg Ala Ala Arg Leu Ala Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Lys Tyr Pro Gly Phe Lys Glu Ala Ala Ala
            420                 425                 430
Lys Gly Leu Arg Asp Ile Tyr Gly Trp Thr Gly Asp Ala Ser Lys Asp
        435                 440                 445
Pro Ile Thr Ile Val Pro Ala Glu Asp Gly Ser Gly Ala Gly Ala Ala
    450                 455                 460
Val Ile Ala Ala Leu Ser Glu Lys Arg Ile Ala Glu Gly Lys Ser Leu
465                 470                 475                 480
Gly Ile Ile Gly Ala
                485

<210> SEQ ID NO 74
```

-continued

```
<211> LENGTH: 1461
<212> TYPE: DNA
<213> ORGANISM: Saccharomyces cerevisiae

<400> SEQUENCE: 74
atggttcatt taggtccaaa aaaccacaa gccagaaagg gttccatggc cgatgtgcca      60
aaggaattga tgcaacaaat tgagaatttt gaaaaatttt tcactgttcc aactgaaact     120
ttacaagccg ttaccaagca cttcatttcc gaattggaaa agggtttgtc caagaagggt     180
ggtaacattc caatgattcc aggttgggtt atggatttcc caactggtaa ggaatccggt     240
gatttcttgg ccattgattt gggtggtacc aacttgagag ttgtcttagt caagttgggc     300
ggtgaccgta ccttttgacac cactcaatct aagtacagat taccagatgc tatgagaact     360
actcaaaatc cagacgaatt gtgggaattt attgccgact cttttgaaagc ttttattgat     420
gagcaattcc cacaaggtat ctctgagcca attccattgg gtttcacctt ttcttttcca     480
gcttctcaaa acaaaatcaa tgaaggtatc ttgcaaagat ggactaaagg ttttgatatt     540
ccaaacattg aaaaccacga tgttgttcca atgttgcaaa agcaaatcac taagaggaat     600
atcccaattg aagttgttgc tttgataaac gacactaccg gtactttggt tgcttcttac     660
tacactgacc cagaaactaa gatgggtgtt atcttcggta ctggtgtcaa tggtgcttac     720
tacgatgttt gttccgatat cgaaaagcta caaggaaaac tatctgatga cattccacca     780
tctgctccaa tggccatcaa ctgtgaatac ggttccttcg ataatgaaca tgtcgttttg     840
ccaagaacta aatacgatat caccattgat gaagaatctc caagaccagg ccaacaaacc     900
tttgaaaaaa tgtcttctgg ttactactta ggtgaaattt tgcgtttggc cttgatggac     960
atgtacaaac aaggtttcat cttcaagaac caagacttgt ctaagttcga caagcctttc    1020
gtcatggaca cttcttaccc agccagaatc gaggaagatc cattcgagaa cctagaagat    1080
accgatgact gtgttcaaaa tgagttcggt atcaacacta ctgttcaaga acgtaaattg    1140
atcagacgtt tatctgaatt gattggtgct agagctgcta gattgtccgt ttgtggtatt    1200
gctgctatct gtcaaagag aggttacaag accggtcaca tcgctgcaga cggttccgtt    1260
tacaacagat acccaggttt caagaaaag gctgccaatg ctttgaagga catttacggc    1320
tggactcaaa cctcactaga cgactaccca atcaagattg ttcctgctga agatggttcc    1380
ggtgctggtg ccgctgttat tgctgctttg gcccaaaaaa gaattgctga aggtaagtcc    1440
gttggtatca tcggtgctta a                                               1461

<210> SEQ ID NO 75
<211> LENGTH: 486
<212> TYPE: PRT
<213> ORGANISM: Saccharomyces cerevisiae

<400> SEQUENCE: 75

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
```

```
                    85                  90                  95
Val Lys Leu Gly Gly Asp Arg Thr Phe Asp Thr Thr Gln Ser Lys Tyr
                100                 105                 110
Arg Leu Pro Asp Ala Met Arg Thr Thr Gln Asn Pro Asp Glu Leu Trp
                115                 120                 125
Glu Phe Ile Ala Asp Ser Leu Lys Ala Phe Ile Asp Glu Gln Phe Pro
            130                 135                 140
Gln Gly Ile Ser Glu Pro Ile Pro Leu Gly Phe Thr Phe Ser Phe Pro
145                 150                 155                 160
Ala Ser Gln Asn Lys Ile Asn Glu Gly Ile Leu Gln Arg Trp Thr Lys
                165                 170                 175
Gly Phe Asp Ile Pro Asn Ile Glu Asn His Asp Val Val Pro Met Leu
                180                 185                 190
Gln Lys Gln Ile Thr Lys Arg Asn Ile Pro Ile Glu Val Val Ala Leu
                195                 200                 205
Ile Asn Asp Thr Thr Gly Thr Leu Val Ala Ser Tyr Tyr Thr Asp Pro
            210                 215                 220
Glu Thr Lys Met Gly Val Ile Phe Gly Thr Gly Val Asn Gly Ala Tyr
225                 230                 235                 240
Tyr Asp Val Cys Ser Asp Ile Glu Lys Leu Gln Gly Lys Leu Ser Asp
                245                 250                 255
Asp Ile Pro Pro Ser Ala Pro Met Ala Ile Asn Cys Glu Tyr Gly Ser
                260                 265                 270
Phe Asp Asn Glu His Val Val Leu Pro Arg Thr Lys Tyr Asp Ile Thr
            275                 280                 285
Ile Asp Glu Glu Ser Pro Arg Pro Gly Gln Gln Thr Phe Glu Lys Met
            290                 295                 300
Ser Ser Gly Tyr Tyr Leu Gly Glu Ile Leu Arg Leu Ala Leu Met Asp
305                 310                 315                 320
Met Tyr Lys Gln Gly Phe Ile Phe Lys Asn Gln Asp Leu Ser Lys Phe
                325                 330                 335
Asp Lys Pro Phe Val Met Asp Thr Ser Tyr Pro Ala Arg Ile Glu Glu
            340                 345                 350
Asp Pro Phe Glu Asn Leu Glu Asp Thr Asp Asp Leu Phe Gln Asn Glu
            355                 360                 365
Phe Gly Ile Asn Thr Thr Val Gln Glu Arg Lys Leu Ile Arg Arg Leu
            370                 375                 380
Ser Glu Leu Ile Gly Ala Arg Ala Ala Arg Leu Ser Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Arg Tyr Pro Gly Phe Lys Glu Lys Ala Ala
                420                 425                 430
Asn Ala Leu Lys Asp Ile Tyr Gly Trp Thr Gln Thr Ser Leu Asp Asp
                435                 440                 445
Tyr Pro Ile Lys Ile Val Pro Ala Glu Asp Gly Ser Gly Ala Gly Ala
            450                 455                 460
Ala Val Ile Ala Ala Leu Ala Gln Lys Arg Ile Ala Glu Gly Lys Ser
465                 470                 475                 480
Val Gly Ile Ile Gly Ala
            485

<210> SEQ ID NO 76
<211> LENGTH: 1164
```

<212> TYPE: DNA
<213> ORGANISM: Klebsiella pneumoniae

<400> SEQUENCE: 76

```
atgagctatc gtatgtttga ttatctggtg ccaaacgtta acttttttgg ccccaacgcc      60
atttccgtag tcggcgaacg ctgccagctg ctggggggga aaaagccct gctggtcacc      120
gacaaaggcc tgcgggcaat taagatggc gcagtggaca aaaccctgca ttatctgcgg      180
gaggccggga tcgaggtggc gatctttgac ggcgtcgagc cgaacccgaa agacaccaac      240
gtgcgcgacg gcctcgccgt gtttcgccgc gaacagtgcg acatcatcgt caccgtgggc      300
ggcggcagcc cgcacgattg cggcaaaggc atcggcatcg ccgccaccca tgagggcgat      360
ctgtaccagt atgccggaat cgagaccctg accaacccgc tgccgcctat cgtcgcggtc      420
aataccaccg ccggcaccgc cagcgaggtc acccgccact gcgtcctgac caacaccgaa      480
accaaagtga agtttgtgat cgtcagctgg cgcaacctgc cgtcggtctc tatcaacgat      540
ccgctgctga tgatcggtaa accggccgcc ctgaccgcgg cgaccgggat ggatgccctg      600
acccacgccg tagaggccta tatctccaaa gacgctaacc ggtgacgga cgccgccgcc      660
atgcaggcga tccgcctcat cgcccgcaac ctgcgccagg ccgtggccct cggcagcaat      720
ctgcaggcgc gggaaaacat ggcctatgcc tctctgctgg ccgggatggc tttcaataac      780
gccaacctcg gctacgtgca cgccatggcc accagctgg gcggcctgta cgacatgccg      840
cacggcgtgg ccaacgctgt cctgctgccg catgtggccc gctacaacct gatcgccaac      900
ccggagaaat cgccgatat cgctgaactg atgggcgaaa atatcaccgg actgtccact      960
ctcgacgcgg cggaaaaagc catcgccgct atcacgcgtc tgtcgatgga tatcggtatt     1020
ccgcagcatc tgcgcgatct gggagtaaaa gaggccgact tcccctacat ggcggagatg     1080
gctctgaaag acggcaatgc gttctcgaac ccgcgtaaag caacgagca ggagattgcc     1140
gcgattttcc gccaggcatt ctga                                            1164
```

<210> SEQ ID NO 77
<211> LENGTH: 387
<212> TYPE: PRT
<213> ORGANISM: Klebsiella pneumoniae

<400> SEQUENCE: 77

```
Met Ser Tyr Arg Met Phe Asp Tyr Leu Val Pro Asn Val Asn Phe Phe
 1               5                  10                  15
Gly Pro Asn Ala Ile Ser Val Val Gly Glu Arg Cys Gln Leu Leu Gly
                20                  25                  30
Gly Lys Lys Ala Leu Leu Val Thr Asp Lys Gly Leu Arg Ala Ile Lys
            35                  40                  45
Asp Gly Ala Val Asp Lys Thr Leu His Tyr Leu Arg Glu Ala Gly Ile
        50                  55                  60
Glu Val Ala Ile Phe Asp Gly Val Glu Pro Asn Pro Lys Asp Thr Asn
 65                  70                  75                  80
Val Arg Asp Gly Leu Ala Val Phe Arg Arg Glu Gln Cys Asp Ile Ile
                85                  90                  95
Val Thr Val Gly Gly Gly Ser Pro His Asp Cys Gly Lys Gly Ile Gly
               100                 105                 110
Ile Ala Ala Thr His Glu Gly Asp Leu Tyr Gln Tyr Ala Gly Ile Glu
           115                 120                 125
Thr Leu Thr Asn Pro Leu Pro Pro Ile Val Ala Val Asn Thr Thr Ala
       130                 135                 140
```

```
Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
            165                 170                 175

Ser Ile Asn Asp Pro Leu Leu Met Ile Gly Lys Pro Ala Ala Leu Thr
        180                 185                 190

Ala Ala Thr Gly Met Asp Ala Leu Thr His Ala Val Glu Ala Tyr Ile
    195                 200                 205

Ser Lys Asp Ala Asn Pro Val Thr Asp Ala Ala Met Gln Ala Ile
210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
            245                 250                 255

Ala Phe Asn Asn Ala Asn Leu Gly Tyr Val His Ala Met Ala His Gln
        260                 265                 270

Leu Gly Gly Leu Tyr Asp Met Pro His Gly Val Ala Asn Ala Val Leu
    275                 280                 285

Leu Pro His Val Ala Arg Tyr Asn Leu Ile Ala Asn Pro Glu Lys Phe
290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
            325                 330                 335

Asp Ile Gly Ile Pro Gln His Leu Arg Asp Leu Gly Val Lys Glu Ala
        340                 345                 350

Asp Phe Pro Tyr Met Ala Glu Met Ala Leu Lys Asp Gly Asn Ala Phe
    355                 360                 365

Ser Asn Pro Arg Lys Gly Asn Glu Gln Glu Ile Ala Ala Ile Phe Arg
370                 375                 380

Gln Ala Phe
385

<210> SEQ ID NO 78
<211> LENGTH: 1824
<212> TYPE: DNA
<213> ORGANISM: Klebsiella pneumoniae
<220> FEATURE:
<221> NAME/KEY: CDS
<222> LOCATION: (1)..(1824)

<400> SEQUENCE: 78 atg ccg tta ata gcc ggg att gat atc ggc aac gcc acc acc gag gtg      48
Met Pro Leu Ile Ala Gly Ile Asp Ile Gly Asn Ala Thr Thr Glu Val
1               5                   10                  15 gcg ctg gcg tcc gac tac ccg cag gcg agg gcg ttt gtt gcc agc ggg      96
Ala Leu Ala Ser Asp Tyr Pro Gln Ala Arg Ala Phe Val Ala Ser Gly
            20                  25                  30 atc gtc gcg acg acg ggc atg aaa ggg acg cgg gac aat atc gcc ggg     144
Ile Val Ala Thr Thr Gly Met Lys Gly Thr Arg Asp Asn Ile Ala Gly
        35                  40                  45 acc ctc gcc gcg ctg gag cag gcc ctg gcg aaa aca ccg tgg tcg atg     192
Thr Leu Ala Ala Leu Glu Gln Ala Leu Ala Lys Thr Pro Trp Ser Met
    50                  55                  60 agc gat gtc tct cgc atc tat ctt aac gaa gcc gcg ccg gtg att ggc     240
Ser Asp Val Ser Arg Ile Tyr Leu Asn Glu Ala Ala Pro Val Ile Gly
65                  70                  75                  80 gat gtg gcg atg gag acc atc acc gag acc att atc acc gaa tcg acc     288
```

```
                  Asp Val Ala Met Glu Thr Ile Thr Glu Thr Ile Ile Thr Glu Ser Thr
                                  85                  90                  95 atg atc ggt cat aac ccg cag acg ccg ggg gtg ggc gtt ggc gtg               336
Met Ile Gly His Asn Pro Gln Thr Pro Gly Gly Val Gly Val Gly Val
            100                 105                 110 ggg acg act atc gcc ctc ggg cgg ctg gcg acg ctg ccg gcg gcg cag           384
Gly Thr Thr Ile Ala Leu Gly Arg Leu Ala Thr Leu Pro Ala Ala Gln
            115                 120                 125 tat gcc gag ggg tgg atc gta ctg att gac gac gcc gtc gat ttc ctt           432
Tyr Ala Glu Gly Trp Ile Val Leu Ile Asp Asp Ala Val Asp Phe Leu
130                 135                 140 gac gcc gtg tgg tgg ctc aat gag gcg ctc gac cgg ggg atc aac gtg           480
Asp Ala Val Trp Trp Leu Asn Glu Ala Leu Asp Arg Gly Ile Asn Val
145                 150                 155                 160 gtg gcg gcg atc ctc aaa aag gac gac ggc gtg ctg gtg aac aac cgc           528
Val Ala Ala Ile Leu Lys Lys Asp Asp Gly Val Leu Val Asn Asn Arg
                165                 170                 175 ctg cgt aaa acc ctg ccg gtg gtg gat gaa gtg acg ctg ctg gag cag           576
Leu Arg Lys Thr Leu Pro Val Val Asp Glu Val Thr Leu Leu Glu Gln
                180                 185                 190 gtc ccc gag ggg gta atg gcg gcg gtg gaa gtg gcc gcg ccg ggc cag           624
Val Pro Glu Gly Val Met Ala Ala Val Glu Val Ala Ala Pro Gly Gln
            195                 200                 205 gtg gtg cgg atc ctg tcg aat ccc tac ggg atc gcc acc ttc ttc ggg           672
Val Val Arg Ile Leu Ser Asn Pro Tyr Gly Ile Ala Thr Phe Phe Gly
210                 215                 220 cta agc ccg gaa gag acc cag gcc atc gtc ccc atc gcc cgc gcc ctg           720
Leu Ser Pro Glu Glu Thr Gln Ala Ile Val Pro Ile Ala Arg Ala Leu
225                 230                 235                 240 att ggc aac cgt tcc gcg gtg gtg ctc aag acc ccg cag ggg gat gtg           768
Ile Gly Asn Arg Ser Ala Val Val Leu Lys Thr Pro Gln Gly Asp Val
                245                 250                 255 cag tcg cgg gtg atc ccg gcg ggc aac ctc tac att agc ggc gaa aag           816
Gln Ser Arg Val Ile Pro Ala Gly Asn Leu Tyr Ile Ser Gly Glu Lys
            260                 265                 270 cgc cgc gga gag gcc gat gtc gcc gag ggc gcg gaa gcc atc atg cag           864
Arg Arg Gly Glu Ala Asp Val Ala Glu Gly Ala Glu Ala Ile Met Gln
        275                 280                 285 gcg atg agc gcc tgc gct ccg gta cgc gac atc cgc ggc gaa ccg ggc           912
Ala Met Ser Ala Cys Ala Pro Val Arg Asp Ile Arg Gly Glu Pro Gly
290                 295                 300 acc cac gcc ggc ggc atg ctt gag cgg gtg cgc aag gta atg gcg tcc           960
Thr His Ala Gly Gly Met Leu Glu Arg Val Arg Lys Val Met Ala Ser
305                 310                 315                 320 ctg acc ggc cat gag atg agc gcg ata tac atc cag gat ctg ctg gcg          1008
Leu Thr Gly His Glu Met Ser Ala Ile Tyr Ile Gln Asp Leu Leu Ala
                325                 330                 335 gtg gat acg ttt att ccg cgc aag gtg cag ggc ggg atg gcc ggc gag          1056
Val Asp Thr Phe Ile Pro Arg Lys Val Gln Gly Gly Met Ala Gly Glu
            340                 345                 350 tgc gcc atg gag aat gcc gtc ggg atg gcg gcg atg gtg aaa gcg gat          1104
Cys Ala Met Glu Asn Ala Val Gly Met Ala Ala Met Val Lys Ala Asp
        355                 360                 365 cgt ctg caa atg cag gtt atc gcc cgc gaa ctg agc gcc cga ctg cag          1152
Arg Leu Gln Met Gln Val Ile Ala Arg Glu Leu Ser Ala Arg Leu Gln
370                 375                 380 acc gag gtg gtg gtg ggc ggc gtg gag gcc aac atg gcc atc gcc ggg          1200
Thr Glu Val Val Val Gly Gly Val Glu Ala Asn Met Ala Ile Ala Gly
385                 390                 395                 400 gcg tta acc act ccc ggc tgt gcg gcg ccg ctg gcg atc ctc gac ctc          1248
```

-continued

```
              Ala Leu Thr Thr Pro Gly Cys Ala Ala Pro Leu Ala Ile Leu Asp Leu
                              405                 410                 415 ggc gcc ggc tcg acg gat gcg gcg atc gtc aac gcg gag ggg cag ata      1296
Gly Ala Gly Ser Thr Asp Ala Ala Ile Val Asn Ala Glu Gly Gln Ile
            420                 425                 430 acg gcg gtc cat ctc gcc ggg gcg ggg aat atg gtc agc ctg ttg att      1344
Thr Ala Val His Leu Ala Gly Ala Gly Asn Met Val Ser Leu Leu Ile
        435                 440                 445 aaa acc gag ctg ggc ctc gag gat ctt tcg ctg gcg gaa gcg ata aaa      1392
Lys Thr Glu Leu Gly Leu Glu Asp Leu Ser Leu Ala Glu Ala Ile Lys
    450                 455                 460 aaa tac ccg ctg gcc aaa gtg gaa agc ctg ttc agt att cgt cac gag      1440
Lys Tyr Pro Leu Ala Lys Val Glu Ser Leu Phe Ser Ile Arg His Glu
465                 470                 475                 480 aat ggc gcg gtg gag ttc ttt cgg gaa gcc ctc agc ccg gcg gtg ttc      1488
Asn Gly Ala Val Glu Phe Phe Arg Glu Ala Leu Ser Pro Ala Val Phe
                485                 490                 495 gcc aaa gtg gtg tac atc aag gag ggc gaa ctg gtg ccg atc gat aac      1536
Ala Lys Val Val Tyr Ile Lys Glu Gly Glu Leu Val Pro Ile Asp Asn
            500                 505                 510 gcc agc ccg ctg gaa aaa att cgt ctc gtg cgc cgg cag gcg aaa gag      1584
Ala Ser Pro Leu Glu Lys Ile Arg Leu Val Arg Arg Gln Ala Lys Glu
        515                 520                 525 aaa gtg ttt gtc acc aac tgc ctg cgc gcg ctg cgc cag gtc tca ccc      1632
Lys Val Phe Val Thr Asn Cys Leu Arg Ala Leu Arg Gln Val Ser Pro
    530                 535                 540 ggc ggt tcc att cgc gat atc gcc ttt gtg gtg ctg gtg ggc ggc tca      1680
Gly Gly Ser Ile Arg Asp Ile Ala Phe Val Val Leu Val Gly Gly Ser
545                 550                 555                 560 tcg ctg gac ttt gag atc ccg cag ctt atc acg gaa gcc ttg tcg cac      1728
Ser Leu Asp Phe Glu Ile Pro Gln Leu Ile Thr Glu Ala Leu Ser His
                565                 570                 575 tat ggc gtg gtc gcc ggg cag ggc aat att cgg gga aca gaa ggg ccg      1776
Tyr Gly Val Val Ala Gly Gln Gly Asn Ile Arg Gly Thr Glu Gly Pro
            580                 585                 590 cgc aat gcg gtc gcc acc ggg ctg cta ctg gcc ggt cag gcg aat taa      1824
Arg Asn Ala Val Ala Thr Gly Leu Leu Leu Ala Gly Gln Ala Asn
        595                 600                 605

<210> SEQ ID NO 79
<211> LENGTH: 607
<212> TYPE: PRT
<213> ORGANISM: Klebsiella pneumoniae

<400> SEQUENCE: 79

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
                20                  25                  30

Ile Val Ala Thr Thr Gly Met Lys Gly Thr Arg Asp Asn Ile Ala Gly
            35                  40                  45

Thr Leu Ala Ala Leu Glu Gln Ala Leu Ala Lys Thr Pro Trp Ser Met
        50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110
```

-continued

```
Gly Thr Thr Ile Ala Leu Gly Arg Leu Ala Thr Leu Pro Ala Ala Gln
            115                 120                 125

Tyr Ala Glu Gly Trp Ile Val Leu Ile Asp Asp Ala Val Asp Phe Leu
130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
                180                 185                 190

Val Pro Glu Gly Val Met Ala Ala Val Glu Val Ala Ala Pro Gly Gln
                195                 200                 205

Val Val Arg Ile Leu Ser Asn Pro Tyr Gly Ile Ala Thr Phe Phe Gly
                210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
                260                 265                 270

Arg Arg Gly Glu Ala Asp Val Ala Glu Gly Ala Glu Ala Ile Met Gln
                275                 280                 285

Ala Met Ser Ala Cys Ala Pro Val Arg Asp Ile Arg Gly Glu Pro Gly
290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
                340                 345                 350

Cys Ala Met Glu Asn Ala Val Gly Met Ala Ala Met Val Lys Ala Asp
                355                 360                 365

Arg Leu Gln Met Gln Val Ile Ala Arg Glu Leu Ser Ala Arg Leu Gln
370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
                420                 425                 430

Thr Ala Val His Leu Ala Gly Ala Gly Asn Met Val Ser Leu Leu Ile
                435                 440                 445

Lys Thr Glu Leu Gly Leu Glu Asp Leu Ser Leu Ala Glu Ala Ile Lys
450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
                500                 505                 510

Ala Ser Pro Leu Glu Lys Ile Arg Leu Val Arg Arg Gln Ala Lys Glu
                515                 520                 525

Lys Val Phe Val Thr Asn Cys Leu Arg Ala Leu Arg Gln Val Ser Pro
530                 535                 540
```

-continued

Gly Gly Ser Ile Arg Asp Ile Ala Phe Val Val Leu Val Gly Ser
545                 550                 555                 560

Ser Leu Asp Phe Glu Ile Pro Gln Leu Ile Thr Glu Ala Leu Ser His
            565                 570                 575

Tyr Gly Val Val Ala Gly Gln Gly Asn Ile Arg Gly Thr Glu Gly Pro
        580                 585                 590

Arg Asn Ala Val Ala Thr Gly Leu Leu Leu Ala Gly Gln Ala Asn
    595                 600                 605

<210> SEQ ID NO 80
<211> LENGTH: 13669
<212> TYPE: DNA
<213> ORGANISM: Artificial Sequence
<220> FEATURE:
<223> OTHER INFORMATION: Plasmid

<400> SEQUENCE: 80

| | | |
|---|---|---|
| tagtaaagcc ctcgctagat tttaatgcgg atgttgcgat tacttcgcca actattgcga | 60 |
| taacaagaaa aagccagcct ttcatgatat atctcccaat ttgtgtaggg cttattatgc | 120 |
| acgcttaaaa ataataaaag cagacttgac ctgatagttt ggctgtgagc aattatgtgc | 180 |
| ttagtgcatc taacgcttga gttaagccgc gccgcgaagc ggcgtcggct tgaacgaatt | 240 |
| gttagacatt atttgccgac taccttggtg atctcgcctt tcacgtagtg acaaattct | 300 |
| tccaactgat ctgcgcgcga ggccaagcga tcttcttctt gtccaagata agcctgtcta | 360 |
| gcttcaagta tgacgggctg atactgggcc ggcaggcgct ccattgccca gtcggcagcg | 420 |
| acatccttcg gcgcgatttt gccggttact gcgctgtacc aaatgcggga caacgtaagc | 480 |
| actacatttc gctcatcgcc agcccagtcg ggcggcgagt tccatagcgt taaggtttca | 540 |
| tttagcgcct caaatagatc ctgttcagga accggatcaa agagttcctc cgccgctgga | 600 |
| cctaccaagg caacgctatg ttctcttgct tttgtcagca agatagccag atcaatgtcg | 660 |
| atcgtggctg gctcgaagat acctgcaaga atgtcattgc gctgccattc tccaaattgc | 720 |
| agttcgcgct tagctggata cgccacgga atgatgtcgt cgtgcacaac aatggtgact | 780 |
| tctacagcgc ggagaatctc gctctctcca ggggaagccg aagtttccaa aaggtcgttg | 840 |
| atcaaagctc gccgcgttgt ttcatcaagc cttacggtca ccgtaaccag caaatcaata | 900 |
| tcactgtgtg gcttcaggcc gccatccact gcggagccgt acaaatgtac ggccagcaac | 960 |
| gtcggttcga gatggcgctc gatgacgcca actacctctg atagttgagt cgatacttcg | 1020 |
| gcgatcaccg cttccctcat gatgtttaac tttgttttag ggcgactgcc ctgctgcgta | 1080 |
| acatcgttgc tgctccataa catcaaacat cgacccacgg cgtaacgcgc ttgctgcttg | 1140 |
| gatgcccgag gcatagactg tacccaaaa aaacagtcat aacaagccat gaaaaccgcc | 1200 |
| actgcgccgt taccaccgct gcgttcggtc aaggttctgg accagttgcg tgagcgcata | 1260 |
| cgctacttgc attacagctt acgaaccgaa caggcttatg tccactgggt tcgtgccttc | 1320 |
| atccgtttcc acggtgtgcg tcacccggca accttgggca gcagcgaagt cgaggcattt | 1380 |
| ctgtcctggc tggcgaacga gcgcaaggtt tcggtctcca cgcatcgtca ggcattggcg | 1440 |
| gccttgctgt tcttctacgg caaggtgctg tgcacggatc tgccctggct tcaggagatc | 1500 |
| ggaagacctc ggccgtcgcg gcgcttgccg gtggtgctga cccggatga agtggttcgc | 1560 |
| atcctcggtt ttctggaagg cgagcatcgt ttgttcgccc agcttctgta tggaacgggc | 1620 |
| atgcggatca gtgagggttt gcaactgcgg gtcaaggatc tggatttcga tcacggcacg | 1680 |
| atcatcgtgc gggagggcaa gggctccaag gatcgggcct tgatgttacc cgagagcttg | 1740 |

```
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgatttttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt  tacaccgttt tcatctgtgc atatggacag ttttcccttt gatatgtaac    2220
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta atctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttttcgct tgagaacttg    2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctt    3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata    3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag    4140
```

```
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860
ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcaccttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga    6300
tgcgtgcccg ccgacccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
```

```
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc acctgatgc     6960 agatgctgcc gggcaccgac tttattttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacgcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctacc    7980 ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700 cgggatcgtc gcgacgacgg gcatgaaagg gacgcggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
```

```
cgtggggacg actatcgccc tcgggcggct ggcgacgctg ccggcggcgc agtatgccga  9000
ggggtggatc gtactgattg acgacgccgt cgatttcctt gacgccgtgt ggtggctcaa  9060
tgaggcgctc gaccggggga tcaacgtggt ggcggcgatc ctcaaaaagg acgacggcgt  9120
gctggtgaac aaccgcctgc gtaaaaccct gccggtggtg gatgaagtga cgctgctgga  9180
gcaggtcccc gagggggtaa tggcggcggt ggaagtggcc gcgccgggcc aggtggtgcg  9240
gatcctgtcg aatccctacg ggatcgccac cttcttcggg ctaagcccgg aagagaccca  9300
ggccatcgtc cccatcgccc gcgccctgat tggcaaccgt tccgcggtgg tgctcaagac  9360
cccgcagggg gatgtgcagt cgcgggtgat cccggcgggc aacctctaca ttagcggcga  9420
aaagcgccgc ggagaggccg atgtcgccga gggcgcggaa gccatcatgc aggcgatgag  9480
cgcctgcgct ccggtacgcg acatccgcgg cgaaccgggc acccacgccg gcggcatgct  9540
tgagcgggtg cgcaaggtaa tggcgtccct gaccggccat gagatgagcg cgatatacat  9600
ccaggatctg ctggcggtgg atacgtttat tccgcgcaag gtgcagggcg ggatggccgg  9660
cgagtgcgcc atggagaatg ccgtcgggat ggcggcgatg gtgaaagcgg atcgtctgca  9720
aatgcaggtt atcgcccgcg aactgagcgc ccgactgcag accgaggtgg tggtgggcgg  9780
cgtggaggcc aacatggcca tcgccggggc gttaaccact cccggctgtg cggcgccgct  9840
ggcgatcctc gacctcggcg ccggctcgac ggatgcggcg atcgtcaacg cggaggggca  9900
gataacggcg gtccatctcg ccggggcggg gaatatggtc agcctgttga ttaaaaccga  9960
gctgggcctc gaggatcttt cgctggcgga agcgataaaa aaatacccgc tggccaaagt 10020
ggaaagcctg ttcagtattc gtcacgagaa tggcgcggtg gagttctttc gggaagccct 10080
cagcccggcg tgttcgcca aagtggtgta catcaaggag ggcgaactgg tgccgatcga 10140
taacgccagc ccgctggaaa aaattcgtct cgtgcgccgg caggcgaaag agaaagtgtt 10200
tgtcaccaac tgcctgcgcg cgctgcgcca ggtctcaccc ggcggttcca ttcgcgatat 10260
cgcctttgtg gtgctggtgg gcggctcatc gctggacttt gagatcccgc agcttatcac 10320
ggaagccttg tcgcactatg gcgtggtcgc cgggcagggc aatattcggg gaacagaagg 10380
gccgcgcaat gcggtcgcca ccgggctgct actggccggt caggcgaatt aaacgggcgc 10440
tcgcgccagc ctctaggtac aaataaaaaa ggcacgtcag atgacgtgcc ttttttcttg 10500
tctagagtac tggcgaaagg gggatgtgct gcaaggcgat taagttgggt aacgccaggg 10560
ttttcccagt cacgacgttg taaaacgacg gccagtgaat tcgagctcgg tacccggggc 10620
ggccgcgcta gcgcccgatc cagctggagt ttgtagaaac gcaaaaggc catccgtcag 10680
gatgccttc tgcttaattt gatgcctggc agtttatggc gggcgtcctg cccgccaccc 10740
tccgggccgt tgcttcgcaa cgttcaaatc cgctcccggc ggatttgtcc tactcaggag 10800
agcgttcacc gacaaacaac agataaaacg aaaggcccag tctttcgact gagcctttcg 10860
ttttatttga tgcctggcag ttccctactc tcgcatgggg agaccccaca ctaccatcgg 10920
cgctacggcg tttcacttct gagttcggca tggggtcagg tgggaccacc gcgctactgc 10980
cgccaggcaa attctgtttt atcagaccgc ttctgcgttc tgatttaatc tgtatcaggc 11040
tgaaaatctt ctctcatccg ccaaaacagc caagcttgca tgcctgcagc ccgggttacc 11100
atttcaacag atcgtcctta gcatataagt agtcgtcaaa aatgaattca acttcgtctg 11160
tttcggcatt gtagccgcca actctgatgg attcgtggtt tttgacaatg atgtcacagc 11220
cttttttcctt taggaagtcc aagtcgaaag tagtggcaat accaatgatc ttacaaccgg 11280
cggcttttcc ggcggcaata cctgctggag cgtcttcaaa tactactacc ttagatttgg 11340
```

```
aagggtcttg ctcattgatc ggatatccta agccattcct gcccttcaga tatggttctg   11400
gatgaggctt accctgtttg acatcattag cggtaatgaa gtactttggt ctcctgattc   11460
ccagatgctc gaaccatttt tgtgccatat cacgggtacc ggaagttgcc acagcccatt   11520
tctcttttgg tagagcgttc aaagcgttgc acagcttaac tgcacctggg acttcaatgg   11580 attttcacc gtacttgacc ggaatttcag cttctaattt gttaacatac tcttcattgg    11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gccacatgtt   12000
tccaaccatt cgtgaacttc tttgcaggta attaaacctt gagcggattg gccattcaac   12060 aactccttt cacattccca ggcgtcctta ccagaagtag ccattagcct agcaaccttg    12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttaccccagc ctagaccttc gacgaaacca   12300
caacctaagg caacaacgtt cttcaaagca ccacagatgg atataccagc aacatcttcg   12360 atgcactaa cgtggaagta aggtctgtgg aacaaggcct ttagaacctt atggtcgacg    12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt tagcaccaac ttcaaaaccc   12600
tttagacagg agatagctct gacgtgtgaa tcaacatgac ctttcaattg gctacagata   12660
cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttcac cattgatctc ttcttcgaac    12840
acccacattt gtactattgg agcgaaaact tctgggtatc ccttacaatt ttcggcaacc   12900
accttggcaa tagtagtacc ccagttacca gatccaatca cagtaaccct gaaaggcttt    12960
tcggcagcct tcaaagaaac agaagaggaa cttctcttc taccagcatt caagtggccg     13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgcacg aattatgcag tgatttacga     13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tccccctttc gccagctggc gtaatagcga agaggcccgc accgatcgcc   13500
cttcccaaca gttgcgcagc ctgaatggcg aatggcgcct gatgcggtat tttctcctta   13560
cgcatctgtg cggtatttca caccgcatat ggtgcactct cagtacaatc tgctctgatg   13620
ccgcatagtt aagccagccc cgacacccgc caacacccgc tgacgagct               13669
```

<210> SEQ ID NO 81
<211> LENGTH: 13543
<212> TYPE: DNA
<213> ORGANISM: Artificial Sequence
<220> FEATURE:
<223> OTHER INFORMATION: Plasmid

<400> SEQUENCE: 81

| | | | | | |
|---|---|---|---|---|---|
| tagtaaagcc | ctcgctagat | tttaatgcgg | atgttgcgat | tacttcgcca | actattgcga | 60 |
| taacaagaaa | aagccagcct | ttcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |
| tccaactgat | ctgcgcgcga | ggccaagcga | tcttcttctt | gtccaagata | agcctgtcta | 360 |
| gcttcaagta | tgacgggctg | atactgggcc | ggcaggcgct | ccattgccca | gtcggcagcg | 420 |
| acatccttcg | gcgcgatttt | gccggttact | gcgctgtacc | aaatgcggga | caacgtaagc | 480 |
| actacatttc | gctcatcgcc | agcccagtcg | ggcggcgagt | tccatagcgt | taaggtttca | 540 |
| tttagcgcct | caaatagatc | ctgttcagga | accggatcaa | agagttcctc | cgccgctgga | 600 |
| cctaccaagg | caacgctatg | ttctcttgct | tttgtcagca | agatagccag | atcaatgtcg | 660 |
| atcgtggctg | gctcgaagat | acctgcaaga | atgtcattgc | gctgccattc | tccaaattgc | 720 |
| agttcgcgct | tagctggata | acgccacgga | atgatgtcgt | cgtgcacaac | aatggtgact | 780 |
| tctacagcgc | ggagaatctc | gctctctcca | ggggaagccg | aagtttccaa | aaggtcgttg | 840 |
| atcaaagctc | gccgcgttgt | ttcatcaagc | cttacggtca | ccgtaaccag | caaatcaata | 900 |
| tcactgtgtg | gcttcaggcc | gccatccact | gcggagccgt | acaaatgtac | ggccagcaac | 960 |
| gtcggttcga | gatggcgctc | gatgacgcca | actacctctg | atagttgagt | cgatacttcg | 1020 |
| gcgatcaccg | cttccctcat | gatgtttaac | tttgttttag | ggcgactgcc | ctgctgcgta | 1080 |
| acatcgttgc | tgctccataa | catcaaacat | cgacccacgg | cgtaacgcgc | ttgctgcttg | 1140 |
| gatgcccgag | gcatagactg | taccccaaaa | aaacagtcat | aacaagccat | gaaaaccgcc | 1200 |
| actgcgccgt | taccaccgct | gcgttcggtc | aaggttctgg | accagttgcg | tgagcgcata | 1260 |
| cgctacttgc | attacagctt | acgaaccgaa | caggcttatg | tccactgggt | tcgtgccttc | 1320 |
| atccgtttcc | acggtgtgcg | tcacccggca | accttgggca | gcagcgaagt | cgaggcattt | 1380 |
| ctgtcctggc | tggcgaacga | gcgcaaggtt | tcggtctcca | cgcatcgtca | ggcattggcg | 1440 |
| gccttgctgt | tcttctacgg | caaggtgctg | tgcacggatc | tgccctggct | tcaggagatc | 1500 |
| ggaagacctc | ggccgtcgcg | gcgcttgccg | gtggtgctga | ccccggatga | agtggttcgc | 1560 |
| atcctcggtt | ttctggaagg | cgagcatcgt | ttgttcgccc | agcttctgta | tggaacgggc | 1620 |
| atgcggatca | gtgagggttt | gcaactgcgg | gtcaaggatc | tggatttcga | tcacggcacg | 1680 |
| atcatcgtgc | gggagggcaa | gggctccaag | gatcgggcct | tgatgttacc | cgagagcttg | 1740 |
| gcacccagcc | tgcgcgagca | ggggaattaa | ttcccacggg | ttttgctgcc | cgcaaacggg | 1800 |
| ctgttctggt | gttgctagtt | tgttatcaga | atcgcagatc | cggcttcagc | cggtttgccg | 1860 |
| gctgaaagcg | ctatttcttc | cagaattgcc | atgattttt | ccccacggga | ggcgtcactg | 1920 |
| gctcccgtgt | tgtcggcagc | tttgattcga | taagcagcat | cgcctgtttc | aggctgtcta | 1980 |
| tgtgtgactg | ttgagctgta | acaagttgtc | tcaggtgttc | aatttcatgt | tctagttgct | 2040 |
| ttgttttact | ggtttcacct | gttctattag | gtgttacatg | ctgttcatct | gttacattgt | 2100 |
| cgatctgttc | atggtgaaca | gctttgaatg | caccaaaaac | tcgtaaaagc | tctgatgtat | 2160 |

```
ctatctttt  tacaccgttt  tcatctgtgc  atatggacag  ttttcccttt  gatatgtaac   2220
ggtgaacagt  tgttctactt  tgtttgtta   gtcttgatgc  ttcactgata  gatacaagag   2280
ccataagaac  ctcagatcct  tccgtattta  gccagtatgt  tctctagtgt  ggttcgttgt   2340
ttttgcgtga  gccatgagaa  cgaaccattg  agatcatact  tactttgcat  gtcactcaaa   2400
aattttgcct  caaaactggt  gagctgaatt  tttgcagtta  aagcatcgtg  tagtgttttt   2460
cttagtccgt  tatgtaggta  ggaatctgat  gtaatggttg  ttggtatttt  gtcaccattc   2520 attttatct   ggttgttctc  aagttcggtt  acgagatcca  tttgtctatc  tagttcaact   2580
tggaaaatca  acgtatcagt  cgggcggcct  cgcttatcaa  ccaccaattt  catattgctg   2640
taagtgttta  aatctttact  tattggtttc  aaaacccatt  ggttaagcct  tttaaactca   2700
tggtagttat  tttcaagcat  taacatgaac  ttaaattcat  caaggctaat  ctctatattt   2760
gccttgtgag  ttttcttttg  tgttagttct  tttaataacc  actcataaat  cctcatagag   2820
tatttgtttt  caaaagactt  aacatgttcc  agattatatt  ttatgaattt  ttttaactgg   2880
aaaagataag  gcaatatctc  ttcactaaaa  actaattcta  attttcgct   tgagaacttg   2940 gcatagtttg  tccactggaa  aatctcaaag  cctttaacca  aaggattcct  gatttccaca   3000
gttctcgtca  tcagctctct  ggttgcttta  gctaatacac  cataagcatt  ttccctactg   3060
atgttcatca  tctgagcgta  ttggttataa  gtgaacgata  ccgtccgttc  tttccttgta   3120
gggttttcaa  tcgtggggtt  gagtagtgcc  acacagcata  aaattagctt  ggtttcatgc   3180
tccgttaagt  catagcgact  aatcgctagt  tcatttgctt  tgaaaacaac  taattcagac   3240
atacatctca  attggtctag  gtgattttaa  tcactatacc  aattgagatg  ggctagtcaa   3300
tgataattac  tagtccttt   cctttgagtt  gtgggtatct  gtaaattctg  ctagacctt    3360 gctggaaaac  ttgtaaattc  tgctagaccc  tctgtaaatt  ccgctagacc  tttgtgtgtt   3420 tttttgttt   atattcaagt  ggttataatt  tatagaataa  agaagaata   aaaaagata    3480 aaagaatag   atcccagccc  tgtgtataac  tcactacttt  agtcagttcc  gcagtattac   3540
aaaaggatgt  cgcaaacgct  gtttgctcct  ctacaaaaca  gaccttaaaa  ccctaaaggc   3600
ttaagtagca  ccctcgcaag  ctcgggcaaa  tcgctgaata  ttccttttgt  ctccgaccat   3660
caggcacctg  agtcgctgtc  ttttcgtga   cattcagttc  gctgcgctca  cggctctggc   3720
agtgaatggg  ggtaaatggc  actacaggcg  cctttatgg   attcatgcaa  ggaaactacc   3780
cataatacaa  gaaaagcccg  tcacgggctt  ctcaggcgt   tttatggcgg  gtctgctatg   3840
tggtgctatc  tgactttttg  ctgttcagca  gttcctgccc  tctgattttc  cagtctgacc   3900
acttcggatt  atcccgtgac  aggtcattca  gactggctaa  tgcacccagt  aaggcagcgg   3960
tatcatcaac  aggcttaccc  gtcttactgt  cgggaattca  tttaaatagt  caaaagcctc   4020
cgaccggagg  cttttgactg  ctaggcgatc  tgtgctgttt  gccacggtat  gcagcaccag   4080
cgcgagatta  tgggctcgca  cgctcgactg  tcggacgggg  gcactggaac  gagaagtcag   4140
gcgagccgtc  acgcccttga  ctatgccaca  tcctgagcaa  ataattcaac  cactaaacaa   4200
atcaaccgcg  tttcccggag  gtaaccaagc  ttgcgggaga  gaatgatgaa  caagagccaa   4260
caagttcaga  caatcaccct  ggccgccgcc  cagcaaatgg  cggcggcggt  ggaaaaaaaa   4320
gccactgaga  tcaacgtggc  ggtggtgttt  tccgtagttg  accgcggagg  caacacgctg   4380
cttatccagc  ggatggacga  ggccttcgtc  tccagctgcg  atatttccct  gaataaagcc   4440
tggagcgcct  gcagctgaa   gcaaggtacc  catgaaatta  cgtcagcggt  ccagccagga   4500
caatctctgt  acggtctgca  gctaaccaac  caacagcgaa  ttattatttt  tggcggcggc   4560
```

```
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg gctggagga gcaggggtc ccctgccaga    4860 ccataaccta tgacggaggc ggtgacgccg ctgcgctggg cgcccggcg gccagaagct   4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacgcggca   5160 gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg   5760
tcggacgggg gcactggaac gagaagtcag gcgagccgtc acgcccttga ctatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000 acagccccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgtta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagacttc tcccactcgg atattcgccg caccgcgcgc accctgatgc    6960
```

```
agatgctgcc gggcaccgac tttattttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct tgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620 tgaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgccgtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgccttg tccgggagtc ggcggaagtg tatcagcagc ggcataagct   8580
gcgtaaagga agctaagcgg aggtcagcat gccgttaata gccggattg atatcggcaa   8640 cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagccggg aagagaccca   9300
ggccatcgtc cccatcgccc gcgccctgat tggcaaccgt tccgcggtgg tgctcaagac   9360
```

```
cccgcaggqq gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagcccc   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620
ttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctgggggact actattgcca   10920
aggtggttgc cgaaaattgt aagggatacc agaagttttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgtttttca cattccacat caattttgc    11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
```

| | | | | | |
|---|---|---|---|---|---|
| agttgttgaa | tggccaatcc | gctcaaggtt | taattacctg | caaagaagtt | cacgaatggt | 11820 |
| tggaaacatg | tggctctgtc | gaagacttcc | cattatttga | agccgtatac | caaatcgttt | 11880 |
| acaacaacta | cccaatgaag | aacctgccgg | acatgattga | agaattagat | ctacatgaag | 11940 |
| attagattta | ttggatccag | gaaacagact | agaattatgg | gattgactac | taaacctcta | 12000 |
| tctttgaaag | ttaacgccgc | tttgttcgac | gtcgacggta | ccattatcat | ctctcaacca | 12060 |
| gccattgctg | cattctggag | ggatttcggt | aaggacaaac | cttatttcga | tgctgaacac | 12120 |
| gttatccaag | tctcgcatgg | ttggagaacg | tttgatgcca | ttgctaagtt | cgctccagac | 12180 |
| tttgccaatg | aagagtatgt | taacaaatta | gaagctgaaa | ttccggtcaa | gtacggtgaa | 12240 |
| aaatccattg | aagtcccagg | tgcagttaag | ctgtgcaacg | ctttgaacgc | tctaccaaaa | 12300 |
| gagaaatggg | ctgtggcaac | ttccggtacc | cgtgatatgg | cacaaaaatg | gttcgagcat | 12360 |
| ctgggaatca | ggagaccaaa | gtacttcatt | accgctaatg | atgtcaaaca | gggtaagcct | 12420 |
| catccagaac | catatctgaa | gggcaggaat | ggcttaggat | atccgatcaa | tgagcaagac | 12480 |
| ccttccaaat | ctaaggtagt | agtatttgaa | gacgctccag | caggtattgc | cgccggaaaa | 12540 |
| gccgccggtt | gtaagatcat | tggtattgcc | actactttcg | acttggactt | cctaaaggaa | 12600 |
| aaaggctgtg | acatcattgt | caaaaaccac | gaatccatca | gagttggcgg | ctacaatgcc | 12660 |
| gaaacagacg | aagttgaatt | cattttttgac | gactacttat | atgctaagga | cgatctgttg | 12720 |
| aaatggtaac | ccgggctgca | ggcatgcaag | cttggctgtt | ttggcggatg | agagaagatt | 12780 |
| ttcagcctga | tacagattaa | atcagaacgc | agaagcggtc | tgataaaaca | gaatttgcct | 12840 |
| ggcggcagta | gcgcggtggt | cccacctgac | cccatgccga | actcagaagt | gaaacgccgt | 12900 |
| agcgccgatg | gtagtgtggg | gtctccccat | gcgagagtag | ggaactgcca | ggcatcaaat | 12960 |
| aaaacgaaag | gctcagtcga | aagactgggc | ctttcgtttt | atctgttgtt | tgtcggtgaa | 13020 |
| cgctctcctg | agtaggacaa | atccgccggg | agcggatttg | aacgttgcga | agcaacggcc | 13080 |
| cggagggtgg | cgggcaggac | gcccgccata | aactgccagg | catcaaatta | agcagaaggc | 13140 |
| catcctgacg | gatggccttt | ttgcgtttct | acaaactcca | gctggatcgg | gcgctagagt | 13200 |
| atacatttaa | atggtaccct | ctagtcaagg | ccttaagtga | gtcgtattac | ggactggccg | 13260 |
| tcgttttaca | acgtcgtgac | tgggaaaacc | ctggcgttac | ccaacttaat | cgccttgcag | 13320 |
| cacatccccc | tttcgccagc | tggcgtaata | gcgaagaggc | ccgcaccgat | cgcccttccc | 13380 |
| aacagttgcg | cagcctgaat | ggcgaatggc | gcctgatgcg | gtattttctc | cttacgcatc | 13440 |
| tgtgcggtat | ttcacaccgc | atatggtgca | ctctcagtac | aatctgctct | gatgccgcat | 13500 |
| agttaagcca | gccccgacac | ccgccaacac | ccgctgacga | gct | | 13543 |

<210> SEQ ID NO 82
<211> LENGTH: 13543
<212> TYPE: DNA
<213> ORGANISM: Artificial Sequence
<220> FEATURE:
<223> OTHER INFORMATION: Plasmid

<400> SEQUENCE: 82

| | | | | | |
|---|---|---|---|---|---|
| tagtaaagcc | ctcgctagat | tttaatgcgg | atgttgcgat | tacttcgcca | actattgcga | 60 |
| taacaagaaa | aagccagcct | ttcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |

```
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320 atccgttttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggttttccg   1860
gctgaaagcg ctatttcttc cagaattgcc atgattttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040 ttgtttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta agcatcgtg tagtgttttt   2460 cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
```

```
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420 tttttgttt atattcaagt ggttataatt tatagaataa agaaagaata aaaaagata   3480 aaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg ccagaaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
```

```
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880 ttcaccttt gagccgatga acaatgaaaa gatcaaaacg atttgcagta ctggcccagc   5940
gccccgtcaa tcaggacggg ctgattggcg agtggcctga agaggggctg atcgccatgg   6000 acagccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatgcg ctgcagaaga   6300 tgcgtgcccg ccggacccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttatttttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct tgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
```

```
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gagtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtgtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtgctcaa    9060
tgaggcgctc gaccgggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg catccgcgcg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgcggggc gttaaccact cccggctgtg cggcgccgct    9840
ggcgatcctc gacctcggcg ccggctcgac ggatgcggcg atcgtcaacg cggaggggca    9900
```

```
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagcgtgc accaatgctt ctggcgtcag gcagccatcg gaagctgtgg tatggctgtg  10560
caggtcgtaa atcactgcat aattcgtgtc gctcaaggcg cactcccgtt ctggataatg  10620
ttttttgcgc cgacatcata acggttctgg caaatattct gaaatgagct gttgacaatt  10680
aatcatccgg ctcgtataat gtgtggaatt gtgagcggat aacaatttca cacaggaaac  10740
agaccatgac tagtaaggag gacaattcca tggctgctgc tgctgataga ttaaacttaa  10800
cttccggcca cttgaatgct ggtagaaaga gaagttcctc ttctgtttct ttgaaggctg  10860
ccgaaaagcc tttcaaggtt actgtgattg gatctggtaa ctggggtact actattgcca  10920
aggtggttgc cgaaaattgt aagggatacc agaagttttt cgctccaata gtacaaatgt  10980
gggtgttcga agaagagatc aatggtgaaa aattgactga aatcataaat actagacatc  11040
aaaacgtgaa atacttgcct ggcatcactc tacccgacaa tttggttgct aatccagact  11100
tgattgattc agtcaaggat gtcgacatca tcgttttcaa cattccacat caattttttgc  11160
cccgtatctg tagccaattg aaaggtcatg ttgattcaca cgtcagagct atctcctgtc  11220
taaagggttt tgaagttggt gctaaaggtg tccaattgct atcctcttac atcactgagg  11280
aactaggtat tcaatgtggt gctctatctg gtgctaacat tgccaccgaa gtcgctcaag  11340
aacactggtc tgaaacaaca gttgcttacc acattccaaa ggatttcaga ggcgagggca  11400
aggacgtcga ccataaggtt ctaaaggcct tgttccacag accttacttc cacgttagtg  11460
tcatcgaaga tgttgctggt atctccatct gtggtgcttt gaagaacgtt gttgccttag  11520
gttgtggttt cgtcgaaggt ctaggctggg gtaacaacgc ttctgctgcc atccaaagag  11580
tcggttgggg tgagatcatc agattcggtc aaatgttttt cccagaatct agagaagaaa  11640
catactacca agagtctgct ggtgttgctg atttgatcac cacctgcgct ggtggtagaa  11700
acgtcaaggt tgctaggcta atggctactt ctggtaagga cgcctgggaa tgtgaaaagg  11760
agttgttgaa tggccaatcc gctcaaggtt taattacctg caaagaagtt cacgaatggt  11820
tggaaacatg tggctctgtc gaagacttcc cattatttga agccgtatac caaatcgttt  11880
acaacaacta cccaatgaag aacctgccgg acatgattga agaattagat ctacatgaag  11940
attagattta ttggatccag gaaacagact agaattatgg gattgactac taaacctcta  12000
tctttgaaag ttaacgccgc tttgttcgac gtcgacggta ccattatcat ctctcaacca  12060
gccattgctg cattctggag ggatttcggt aaggacaaac cttatttcga tgctgaacac  12120
gttatccaag tctcgcatgg ttggagaacg tttgatgcca ttgctaagtt cgctccagac  12180
tttgccaatg aagagtatgt taacaaatta gaagctgaaa ttccggtcaa gtacggtgaa  12240
aaatccattg aagtcccagg tgcagttaag ctgtgcaacg ctttgaacgc tctaccaaaa  12300
```

```
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttgac gactacttat atgctaagga cgatctgttg     12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag gaactgccag gcatcaaat     12960 aaaacgaaag gctcagtcga aagactgggc ctttcgtttt atctgttgtt tgtcggtgaa    13020
cgctctcctg agtaggacaa atccgccggg agcggatttg aacgttgcga agcaacggcc    13080
cggagggtgg cgggcaggac gcccgccata aactgccagg catcaaatta gcagaaggc     13140 catcctgacg gatggccttt ttgcgtttct acaaactcca gctggatcgg cgctagagt     13200 atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543

<210> SEQ ID NO 83
<211> LENGTH: 13402
<212> TYPE: DNA
<213> ORGANISM: Artificial Sequence
<220> FEATURE:
<223> OTHER INFORMATION: Plamid

<400> SEQUENCE: 83
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct      300 tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga    600
cctaccaagg caacgctatg ttctcttgct tttgtcagca agatagccag atcaatgtcg     660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
```

```
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatctttt tacaccgttt tcatctgtgc atatggacag ttttcccttt gatatgtaac   2220
ggtgaacagt tgttctactt tgtttgtta gtccttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaagacttt aacatgttcc agattatatt ttatgaattt ttttaactgg   2880
aaaagataag gcaatatctc ttcactaaaa actaattcta attttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
```

```
atacatctca attggtctag gtgattttaa tcactatacc aattgagatg ggctagtcaa    3300
tgataattac tagtccttt  cctttgagtt gtgggtatct gtaaattctg ctagacctt     3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata     3480 aaagaatag  atcccagccc tgtgtataac tcactacttt agtcagttcc gcagtattac    3540 aaaggatgt  cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg cctttttatgg attcatgcaa ggaaactacc   3780
cataatacaa gaaaagcccg tcacgggctt ctcagggcgt tttatggcgg gtctgctatg    3840
tggtgctatc tgacttttg  ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt ccacggtat  gcagcaccag    4080 cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttccggag  gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttaatga  gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc  ccctgccaga    4860 ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacgcggca    5160 gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
```

```
agaagtcagg cgagccgtca cgcccttgac aatgccacat cctgagcaaa taattcaacc   5700
actaaacaaa tcaaccgcgt ttcccggagg taaccaagct tcacctttg agccgatgaa    5760 caatgaaaag atcaaaacga tttgcagtac tggcccagcg ccccgtcaat caggacgggc   5820
tgattggcga gtggcctgaa gagggctga tcgccatgga cagccccttt gacccggtct    5880
cttcagtaaa agtggacaac ggtctgatcg tcgaactgga cggcaaacgc cgggaccagt   5940
ttgacatgat cgaccgattt atcgccgatt acgcgatcaa cgttgagcgc acagagcagg   6000
caatgcgcct ggaggcggtg gaaatagccc gtatgctggt ggatattcac gtcagccggg   6060
aggagatcat tgccatcact accgccatca cgccggccaa agcggtcgag gtgatggcgc   6120
agatgaacgt ggtggagatg atgatggcgc tgcagaagat gcgtgcccgc cggacccccct  6180 ccaaccagtg ccacgtcacc aatctcaaag ataatccggt gcagattgcc gctgacgccg   6240
ccgaggccgg gatccgcggc ttctcagaac aggagaccac ggtcggtatc gcgcgctacg   6300
cgccgtttaa cgccctggcg ctgttggtcg gttcgcagtg cggccgcccc ggcgtgttga   6360
cgcagtgctc ggtggaagag gccaccgagc tggagctggg catgcgtggc ttaaccagct   6420
acgccgagac ggtgtcggtc tacggcaccg aagcggtatt taccgacggc gatgatacgc   6480
cgtggtcaaa ggcgttcctc gcctcggcct acgcctcccg cggggttgaaa atgcgctaca  6540 cctccggcac cggatccgaa gcgctgatgg gctattcgga gagcaagtcg atgctctacc   6600
tcgaatcgcg ctgcatcttc attactaaag gcgccggggt tcagggactg caaaacggcg   6660
cggtgagctg tatcggcatg accggcgctg tgccgtcggg cattcgggcg gtgctggcgg   6720
aaaacctgat cgcctctatg ctcgacctcg aagtggcgtc cgccaacgac cagactttct   6780
cccactcgga tattcgccgc accgcgcgca ccctgatgca gatgctgccg ggcaccgact   6840
ttattttctc cggctacagc gcggtgccga actacgacaa catgttcgcc ggctcgaact   6900
tcgatgcgga agattttgat gattacaaca tcctgcagcg tgacctgatg gttgacggcg   6960
gcctgcgtcc ggtgaccgag gcggaaacca ttgccattcg ccagaaagcg cgcgggcga   7020 tccaggcggt ttccgcgag ctgggctgc cgccaatcgc cgacgaggag gtggaggccg     7080
ccacctacgc gcacggcagc aacgagatgc cgccgcgtaa cgtggtggag gatctgagtg   7140
cggtggaaga gatgatgaag cgcaacatca ccggcctcga tattgtcggc gcgctgagcc   7200
gcagcggctt tgaggatatc gccagcaata ttctcaatat gctgcgccag cgggtcaccg   7260
gcgattacct gcagacctcg gccattctcg atcggcagtt cgaggtggtg agtgcggtca   7320
acgacatcaa tgactatcag gggccgggca ccggctatcg catctctgcc gaacgctggg   7380
cggagatcaa aaatattccg ggcgtggttc agcccgacac cattgaataa gcggtattc   7440 ctgtgcaaca gacaacccaa attcagccct ctttacccct gaaaacccgc gagggcgggg   7500
tagcttctgc cgatgaacgc gccgatgaag tggtgatcgg cgtcggccct gccttcgata   7560
aacaccagca tcacactctg atcgatatgc cccatggcgc gatcctcaaa gagctgattg   7620
ccggggtgga agaagagggg cttcacgccc gggtggtgcg cattctgcgc acgtccgacg   7680
tctcctttat ggcctgggat gcggccaacc tgagcggctc ggggatcggc atcggtatcc   7740
agtcgaaggg gaccacggtc atccatcagc gcgatctgct gccgctcagc aacctggagc   7800
tgttctccca ggcgccgctg ctgacgctgg agacctaccg gcagattggc aaaaacgctg   7860
cgcgctatgc gcgcaaagag tcaccttcgc cggtgccggt ggtgaacgat cagatggtgc   7920
ggccgaaatt tatggccaaa gccgcgctat ttcatatcaa agagaccaaa catgtggtgc   7980
aggacgccga gcccgtcacc ctgcacatcg acttagtaag ggagtgacca tgagcgagaa   8040
```

```
aaccatgcgc gtgcaggatt atccgttagc cacccgctgc ccggagcata tcctgacgcc   8100
taccggcaaa ccattgaccg atattaccct cgagaaggtg ctctctggcg aggtgggccc   8160
gcaggatgtg cggatctccc gccagaccct tgagtaccag gcgcagattg ccagcagat   8220 gcagcgccat gcggtggcgc gcaatttccg ccgcgcggcg gagcttatcg ccattcctga   8280
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggg acgcgggaca atatcgccgg gaccctcgcc gcgctggagc aggccctggc   8640
gaaaacaccg tggtcgatga gcgatgtctc tcgcatctat cttaacgaag ccgcgccggt   8700
gattggcgat gtggcgatgg agaccatcac cgagaccatt atcaccgaat cgaccatgat   8760
cggtcataac ccgcagacgc cgggcggggt gggcgttggc gtggggacga ctatcgccct   8820
cgggcggctg gcgacgctgc cggcggcgca gtatgccgag gggtggatcg tactgattga   8880
cgacgccgtc gatttccttg acgccgtgtg gtggctcaat gaggcgctcg accgggggat   8940
caacgtggtg gcgcgcgatcc tcaaaaagga cgacggcgtg ctggtgaaca accgcctgcg   9000 taaaccctg ccggtggtgg atgaagtgac gctgctggag caggtccccg aggggtaat   9060 ggcggcggtg gaagtggccg cgccgggcca ggtggtgcgg atcctgtcga atccctacgg   9120
gatcgccacc ttcttcgggc taagcccgga agagacccag gccatcgtcc ccatcgcccg   9180
cgccctgatt ggcaaccgtt ccgcggtggt gctcaagacc ccgcagggggg atgtgcagtc   9240 gcgggtgatc ccggcgggca acctctacat tagcggcgaa aagcgccgcg gagaggccga   9300
tgtcgccgag ggcgcggaag ccatcatgca ggcgatgagc gcctgcgctc cggtacgcga   9360
catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg cgaactggt gccgatcgat aacgccagcc cgctggaaaa   10020
aattcgtctc gtgcgccggc aggcgaaaga gaaagtgttt gtcaccaact gcctgcgcgc   10080
gctgcgccag gtctcacccg gcggttccat tcgcgatatc gcctttgtgg tgctggtggg   10140
cggctcatcg ctggactttg agatcccgca gcttatcacg gaagccttgt cgcactatgg   10200
cgtggtcgcc gggcagggca atattcgggg aacagaaggg ccgcgcaatg cggtcgccac   10260
cgggctgcta ctggccggtc aggccgaatta acgggcgct cgcgccagcc tctaggtaca   10320
aataaaaaag gcacgtcaga tgacgtgcct ttttcttgt ctagcgtgca ccaatgcttc   10380
tggcgtcagg cagccatcgg aagctgtggt atggctgtgc aggtcgtaaa tcactgcata   10440
```

```
attcgtgtcg ctcaaggcgc actcccgttc tggataatgt tttttgcgcc gacatcataa    10500
cggttctggc aaatattctg aaatgagctg ttgacaatta atcatccggc tcgtataatg    10560
tgtggaattg tgagcggata acaatttcac acaggaaaca gaccatgact agtaaggagg    10620
acaattccat ggctgctgct gctgatagat taaacttaac ttccggccac ttgaatgctg    10680
gtagaaagag aagttcctct tctgtttctt gaaggctgc cgaaaagcct ttcaaggtta     10740
ctgtgattgg atctggtaac tggggtacta ctattgccaa ggtggttgcc gaaaattgta    10800
agggataccc agaagttttc gctccaatag tacaaatgtg ggtgttcgaa gaagagatca    10860
atggtgaaaa attgactgaa atcataaata ctagacatca aaacgtgaaa tacttgcctg    10920
gcatcactct acccgacaat ttggttgcta atccagactt gattgattca gtcaaggatg    10980
tcgacatcat cgttttcaac attccacatc aattttttgcc ccgtatctgt agccaattga   11040
aaggtcatgt tgattcacac gtcagagcta tctcctgtct aaagggtttt gaagttggtg    11100
ctaaaggtgt ccaattgcta tcctcttaca tcactgagga actaggtatt caatgtggtg    11160
ctctatctgg tgctaacatt gccaccgaag tcgctcaaga acactggtct gaaacaacag    11220
ttgcttacca cattccaaag gatttcagag gcgagggcaa ggacgtcgac cataaggttc    11280
taaaggcctt gttccacaga ccttacttcc acgttagtgt catcgaagat gttgctggta    11340
tctccatctg tggtgctttg aagaacgttg ttgccttagg ttgtggtttc gtcgaaggtc    11400
taggctgggg taacaacgct tctgctgcca tccaaagagt cggtttgggt gagatcatca    11460
gattcggtca aatgttttc ccagaatcta gagaagaaac atactaccaa gagtctgctg     11520
gtgttgctga tttgatcacc acctgcgctg gtggtagaaa cgtcaaggtt gctaggctaa    11580
tggctacttc tggtaaggac gcctgggaat gtgaaaagga gttgttgaat ggccaatccg    11640
ctcaaggttt aattacctgc aaagaagttc acgaatggtt ggaaacatgt ggctctgtcg    11700
aagacttccc attatttgaa gccgtatacc aaatcgttta caacaactac ccaatgaaga    11760
acctgccgga catgattgaa gaattagatc tacatgaaga ttagatttat tggatccagg    11820
aaacagacta gaattatggg attgactact aaacctctat ctttgaaagt taacgccgct    11880
ttgttcgacg tcgacggtac cattatcatc tctcaaccag ccattgctgc attctggagg    11940
gatttcggta aggacaaacc ttatttcgat gctgaacacg ttatccaagt ctcgcatggt    12000
tggagaacgt ttgatgccat tgctaagttc gctccagact ttgccaatga agagtatgtt    12060
aacaaattag aagctgaaat tccggtcaag tacggtgaaa aatccattga agtcccaggt    12120
gcagttaagc tgtgcaacgc tttgaacgct ctaccaaaag agaaatgggc tgtggcaact    12180
tccggtaccc gtgatatggc acaaaaatgg ttcgagcatc tgggaatcag agaccaaaag    12240
tacttcatta ccgctaatga tgtcaaacag ggtaagcctc atccagaacc atatctgaag    12300
ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540 attttgacg actacttata tgctaaggac gatctgttga atggtaacc cgggctgcag      12600 gcatgcaagc ttggctgttt tggcggatga gagaagattt tcagcctgat acagattaaa    12660
tcagaacgca gaagcggtct gataaaacag aatttgcctg gcggcagtag cgcggtggtc    12720
ccacctgacc ccatgccgaa ctcagaagtg aaacgccgta gcgccgatgg tagtgtgggg    12780
tctccccatg cgagagtagg gaactgccag gcatcaaata aaacgaaagg ctcagtcgaa    12840
```

-continued

| | |
|---|---|
| agactgggcc tttcgtttta tctgttgttt gtcggtgaac gctctcctga gtaggacaaa | 12900 |
| tccgccggga gcggatttga acgttgcgaa gcaacggccc ggagggtggc gggcaggacg | 12960 |
| cccgccataa actgccaggc atcaaattaa gcagaaggcc atcctgacgg atggcctttt | 13020 |
| tgcgtttcta caaactccag ctggatcggg cgctagagta tacatttaaa tggtaccctc | 13080 |
| tagtcaaggc cttaagtgag tcgtattacg gactggccgt cgttttacaa cgtcgtgact | 13140 |
| gggaaaaccc tggcgttacc caacttaatc gccttgcagc acatccccct ttcgccagct | 13200 |
| ggcgtaatag cgaagaggcc cgcaccgatc gcccttccca cagttgcgc agcctgaatg | 13260 |
| gcgaatggcg cctgatgcgg tattttctcc ttacgcatct gtgcggtatt tcacaccgca | 13320 |
| tatggtgcac tctcagtaca atctgctctg atgccgcata gttaagccag ccccgacacc | 13380 |
| cgccaacacc cgctgacgag ct | 13402 |

<210> SEQ ID NO 84
<211> LENGTH: 14443
<212> TYPE: DNA
<213> ORGANISM: Artificial Sequence
<220> FEATURE:
<223> OTHER INFORMATION: Plasmid

<400> SEQUENCE: 84

| | |
|---|---|
| ttctgataac aaactagcaa caccagaaca gcccgtttgc gggcagcaaa acccgtggga | 60 |
| attaattccc ctgctcgcgc aggctgggtg ccaagctctc gggtaacatc aaggcccgat | 120 |
| ccttggagcc cttcttacag agatgaaaaa caaaccgcga cgccaggcgg catcgcggtc | 180 |
| tcagagatat gtttacgtag atcgaagagc accggtgttt aaacgcccct tgacgatgcca | 240 |
| catcctgagc aaataattca accactaaac aaatcaaccg cgtttcccgg aggtaaccga | 300 |
| gctcatgatc ctgtgttgtg gtgaagccct gatcgacatg ctgccccggc agacgacgct | 360 |
| gggtgaggcg gctttgccc cttacgcagg cggagcggtc ttcaacacgg caattgcgct | 420 |
| ggggcgtctt ggcgtcccctt cagccttttt taccggtctt tccgacgaca tgatgggcga | 480 |
| tatcctgcgg gagaccctgc gggccagcaa ggtggatttc agctattgcg ccaccctgtc | 540 |
| gcgcccacc accattgcgt tcgttaagct ggttgatggc catgcgacct acgctttta | 600 |
| cgacgagaac accgccggcc ggatgatcac cgaggccgaa cttccggcct tgggagcgga | 660 |
| ttgcgaagcg ctgcatttcg gcgccatcag ccttattccc gaaccctgcg gcagcaccta | 720 |
| tgaggcgctg atgacgcgcg agcatgagac ccgcgtcatc tcgctcgatc gaacattcg | 780 |
| tccccggcttc atccagaaca agcagtcgca catggcccgc atccgccgca tggcggcgat | 840 |
| gtctgacatc gtcaagttct cggatgagga cctggcgtgg ttcggtctgg aaggcgacga | 900 |
| ggacacgctt gcccgccact ggctgcacca cggtgcaaaa ctcgtcgttg tcacccgtgg | 960 |
| cgccaagggt gccgtggtt acagcgccaa tctcaaggtg gaagtggcct ccgagcgcgt | 1020 |
| cgaagtggtc gatacggtcg cgccggcga tacgttcgat gccggcattc ttgcttcgct | 1080 |
| gaaaatgcag ggcctgctga ccaaagcgca ggtggcttcg ctgagcgaag agcagatcag | 1140 |
| aaaagctttg gcgcttggcg cgaaagccgc tgcggtcact gtctcgcggg ctggcgcaaa | 1200 |
| tccgcctttc gcgcatgaaa tcggtttgtg attaattaaa gcacgcagtc aaacaaaaaa | 1260 |
| cccgcgccat tgcgcgggtt ttttatgcc cgaaggcgcg ccagcacgca gtcaaacaaa | 1320 |
| aaacccgcgc cattgcgcgg gttttttttat gcccgaacgg ccgaggtctt ccgatctcct | 1380 |
| gaagccaggg cagatccgtg cacagcacct tgccgtagaa gacagcaag gccgccaatg | 1440 |
| cctgacgatg cgtggagacc gaaaccttgc gctcgttcgc cagccaggac agaaatgcct | 1500 |

```
cgacttcgct gctgcccaag gttgccgggt gacgcacacc gtggaaacgg atgaaggcac    1560
gaacccagtg gacataagcc tgttcggttc gtaagctgta atgcaagtag cgtatgcgct    1620
cacgcaactg gtccagaacc ttgaccgaac gcagcggtgg taacggcgca gtggcggttt    1680
tcatggcttg ttatgactgt ttttttgggg tacagtctat gcctcgggca tccaagcagc    1740
aagcgcgtta cgccgtgggt cgatgtttga tgttatggag cagcaacgat gttacgcagc    1800
agggcagtcg ccctaaaaca aagttaaaca tcatgaggga agcggtgatc gccgaagtat    1860
cgactcaact atcagaggta gttggcgtca tcgagcgcca tctcgaaccg acgttgctgg    1920
ccgtacattt gtacggctcc gcagtggatg gcggcctgaa gccacacagt gatattgatt    1980
tgctggttac ggtgaccgta aggcttgatg aaacaacgcg gcgagctttg atcaacgacc    2040
ttttggaaac ttcggcttcc cctggagaga gcgagattct ccgcgctgta gaagtcacca    2100
ttgttgtgca cgacgacatc attccgtggc gttatccagc taagcgcgaa ctgcaatttg    2160
gagaatggca gcgcaatgac attcttgcag gtatcttcga gccagccacg atcgacattg    2220
atctggctat cttgctgaca aaagcaagag aacatagcgt tgccttggta ggtccagcgg    2280
cggaggaact ctttgatccg gttcctgaac aggatctatt tgaggcgcta atgaaacct    2340 taacgctatg gaactcgccg cccgactggg ctggcgatga gcgaaatgta gtgcttacgt    2400
tgtcccgcat ttggtacagc gcagtaaccg gcaaaatcgc gccgaaggat gtcgctgccg    2460
actgggcaat ggagcgcctg ccggcccagt atcagcccgt catacttgaa gctagacagg    2520
cttatcttgg acaagaagaa gatcgcttgg cctcgcgcgc agatcagttg gaagaatttg    2580
tccactacgt gaaaggcgag atcaccaagg tagtcggcaa ataatgtcta acaattcgtt    2640
caagccgacg ccgcttcgcg cgcggcctta actcaagcgt tagatgcact aagcacataa    2700
ttgctcacag ccaaactatc aggtcaagtc tgcttttatt attttttaagc gtgcataata    2760 agccctacac aaattgggag atatatcatg aaaggctggc ttttttcttgt tatcgcaata    2820 gttggcgaag taatcgcaac atccgcatta aaatctagcg agggctttac taagctcgtc    2880
agcgggtgtt ggcgggtgtc ggggctggct taactatgcg gcatcagagc agattgtact    2940
gagagtgcac catatgcggt gtgaaatacc gcacagatgc gtaaggagaa aataccgcat    3000
caggcgccat tcgccattca ggctgcgcaa ctgttgggaa gggcgatcgg tgcgggcctc    3060
ttcgctatta cgccagctgg cgaaagggggg atgtgctgca aggcgattaa gttgggtaac    3120
gccagggttt tcccagtcac gacgttgtaa aacgacggcc agtccgtaat acgactcact    3180
taaggccttg actagagggt accatttaaa tgtatactct agcgcccgat ccagctggag    3240
tttgtagaaa cgcaaaaagg ccatccgtca ggatggcctt ctgcttaatt tgatgcctgg    3300
cagtttatgg cgggcgtcct gcccgccacc ctccgggccg ttgcttcgca acgttcaaat    3360
ccgctcccgg cggatttgtc ctactcagga gagcgttcac cgacaaacaa cagataaaac    3420
gaaaggccca gtctttcgac tgagcctttc gttttatttg atgcctggca gttccctact    3480
ctcgcatggg gagaccccac actaccatcg gcgctacggc gtttcacttc tgagttcggc    3540
atggggtcag gtgggaccac cgcgctactg ccgccaggca aattctgttt tatcagaccg    3600
cttctgcgtt ctgatttaat ctgtatcagg ctgaaaatct tctctcatcc gccaaaacag    3660
ccaagcttgc atgcctgcag cccgggttac catttcaaca gatcgtcctt agcatataag    3720
tagtcgtcaa aaatgaattc aacttcgtct gtttcggcat tgtagccgcc aactctgatg    3780
gattcgtggt ttttgacaat gatgtcacag ccttttttcct ttaggaagtc caagtcgaaa    3840
gtagtggcaa taccaatgat cttacaaccg gcggcttttc cggcggcaat acctgctgga    3900
```

```
gcgtcttcaa atactactac cttagatttg gaagggtctt gctcattgat cggatatcct   3960
aagccattcc tgcccttcag atatggttct ggatgaggct taccctgttt gacatcatta   4020
gcggtaatga agtactttgg tctcctgatt cccagatgct cgaaccattt ttgtgccata   4080
tcacgggtac cggaagttgc cacagcccat ttctcttttg gtagagcgtt caaagcgttg   4140
cacagcttaa ctgcacctgg gacttcaatg gattttttcac cgtacttgac cggaatttca   4200
gcttctaatt tgttaacata ctcttcattg gcaaagtctg gagcgaactt agcaatggca   4260
tcaaacgttc tccaaccatg cgagacttgg ataacgtgtt cagcatcgaa ataaggtttg   4320
tccttaccga aatccctcca gaatgcagca atggctggtt gagagatgat aatggtaccg   4380
tcgacgtcga acaaagcggc gttaactttc aaagatagag gtttagtagt caatcccata   4440
attctagtct gtttcctgga tccaataaat ctaatcttca tgtagatcta attcttcaat   4500
catgtccggc aggttcttca ttgggtagtt gttgtaaacg atttggtata cggcttcaaa   4560
taatgggaag tcttcgacag agccacatgt ttccaaccat tcgtgaactt ctttgcaggt   4620
aattaaacct tgagcggatt ggccattcaa caactccttt tcacattccc aggcgtcctt   4680
accagaagta gccattagcc tagcaacctt gacgtttcta ccaccagcgc aggtggtgat   4740
caaatcagca acaccagcag actcttggta gtatgtttct tctctagatt ctgggaaaaa   4800
catttgaccg aatctgatga tctcacccaa accgactctt tggatggcag cagaagcgtt   4860
gttaccccag cctagacctt cgacgaaacc acaacctaag gcaacaacgt tcttcaaagc   4920
accacagatg gagataccag caacatcttc gatgacacta acgtggaagt aaggtctgtg   4980
gaacaaggcc tttagaacct tatggtcgac gtccttgccc tcgcctctga aatcctttgg   5040
aatgtggtaa gcaactgttg tttcagacca gtgttcttga gcgacttcgg tggcaatgtt   5100
agcaccagat agagcaccac attgaatacc tagttcctca gtgatgtaag aggatagcaa   5160
ttggacacct ttagcaccaa cttcaaaacc ctttagacag gagatagctc tgacgtgtga   5220
atcaacatga cctttcaatt ggctacagat acggggcaaa aattgatgtg gaatgttgaa   5280
aacgatgatg tcgacatcct tgactgaatc aatcaagtct ggattagcaa ccaaattgtc   5340
gggtagagtg atgccaggca agtatttcac gttttgatgt ctagtattta tgatttcagt   5400
caatttttca ccattgatct cttcttcgaa cacccacatt tgtactattg gagcgaaaac   5460
ttctgggtat cccttacaat tttcggcaac caccttggca atagtagtac cccagttacc   5520
agatccaatc acagtaacct tgaaaggctt ttcggcagcc ttcaaagaaa cagaagagga   5580
acttctcttt ctaccagcat tcaagtggcc ggaagttaag tttaatctat cagcagcagc   5640
agccatggaa ttgtcctcct tactagtcat ggtctgtttc ctgtgtgaaa ttgttatccg   5700
ctcacaattc cacacattat acgagccgga tgattaattg tcaacagctc atttcagaat   5760
atttgccaga accgttatga tgtcggcgca aaaaacatta tccagaacgg gagtgcgcct   5820
tgagcgacac gaattatgca gtgatttacg acctgcacag ccataccaca gcttccgatg   5880
gctgcctgac gccagaagca ttggtgcacg ctagacaaga aaaaaggcac gtcatctgac   5940
gtgccttttt tatttgtacc tagaggctgg cgcgagcgcc cgtttaattc gcctgaccgg   6000
ccagtagcag cccggtggcg accgcattgc gcggcccttc tgttccccga atattgccct   6060
gcccggcgac cacgccatag tgcgacaagg cttccgtgat aagctgcggg atctcaaagt   6120
ccagcgatga gccgcccacc agcaccacaa aggcgatatc gcgaatggaa ccgccgggtg   6180
agacctggcg cagcgcgcgc aggcagttgg tgacaaacac tttctctttc gcctgccggc   6240
gcacgagacg aatttttccc agcgggctgg cgttatcgat cggcaccagt tcgccctcct   6300
```

```
tgatgtacac cactttggcg aacaccgccg ggctgagggc ttcccgaaag aactccaccg    6360
cgccattctc gtgacgaata ctgaacaggc tttccacttt ggccagcggg tattttttta    6420
tcgcttccgc cagcgaaaga tcctcgaggc ccagctcggt tttaatcaac aggctgacca    6480
tattccccgc cccggcgaga tggaccgccg ttatctgccc ctccgcgttg acgatcgccg    6540
catccgtcga gccggcgccg aggtcgagga tcgccagcgg cgccgcacag ccggagtgg    6600 ttaacgcccc ggcgatggcc atgttggcct ccacgccgcc caccaccacc tcggtctgca    6660
gtcgggcgct cagttcgcgg gcgataacct gcatttgcag acgatccgct ttcaccatcg    6720
ccgccatccc gacggcattc tccatggcgc actcgcggc catcccgccc tgcaccttgc    6780
gcggaataaa cgtatccacc gccagcagat cctggatgta tatcgcgctc atctcatggc    6840
cggtcaggga cgccattacc ttgcgcaccc gctcaagcat gccgccggcg tgggtgcccg    6900
gttcgccgcg gatgtcgcgt accggagcgc aggcgctcat cgcctgcatg atggcttccg    6960
cgccctcggc gacatcggcc tctccgcggc gcttttcgcc gctaatgtag aggttgcccg    7020
ccgggatcac ccgcgactgc acatccccct gcgggtgtct gagcaccacc gcggaacggt    7080
tgccaatcag ggcgcgggcg atggggacga tggcctgggc tcttccggg cttagcccga    7140 agaaggtggc gatcccgtag ggattcgaca ggatccgcac cacctggccc ggcgcggcca    7200
cttccaccgc cgccattacc ccctcgggga cctgctccag cagcgtcact tcatccacca    7260
ccggcagggt tttacgcagg cggttgttca ccagcacgcc gtcgtccttt ttgaggatcg    7320
ccgccaccac gttgatcccc cggtcagcg cctcattgag ccaccacacg cgtcaagga     7380 aatcgacggc gtcgtcaatc agtacgatcc accctcggc atactgcgcc gccggcagcg    7440
tcgccagccg cccgagggcg atagtcgtcc ccacgccaac gcccaccccg cccggcgtct    7500
gcgggttatg accgatcatg gtcgattcgg tgataatggt ctcggtgatg gtctccatcg    7560
ccacatcgcc aatcaccggc gcggcttcgt taagatagat gcgagagaca tcgctcatcg    7620
accacggtgt tttcgccagg gcctgctcca gcgcggcgag ggtcccggcg atattgtccc    7680
gcgtcccttt catgcccgtc gtcgcgacga tcccgctggc aacaaacgcc ctcgcctgcg    7740
ggtagtcgga cgccagcgcc acctcggtgg tggcgttgcc gatatcaatc ccggctatta    7800
acggcatgct gacctccgct tagcttcctt tacgcagctt atgccgctgc tgatacactt    7860
ccgccgactc ccggacaaag gcggcattca ctgtcgcatg ccaggtgtgc tccagctcgt    7920
cggcgatcgc cagcagctcc gcctgcgagg agcggaacgg gcgcagcgcg ttatagatag    7980
ccagaatgcg ctcgtcagga atggcgataa gctccgccgc gcggcggaaa ttgcgcgcca    8040
ccgcatggcg ctgcatctgc tcggcaatct gcgcctggta ctcaagggtc tggcgggaga    8100
tccgcacatc ctgcgggccc acctcgccag agagcacctt tcgagggta atatcggtca    8160 atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg cggctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520 ggtcccttc gactggatac cgatgccgat ccccgagccg ctcaggttgg ccgcatccca    8580
ggccataaag gagacgtcgg acgtgcgcag aatgcgcacc acccgggcgt gaagcccctc    8640
ttcttccacc ccggcaatca gctctttgag gatcgcgcca tggggcatat cgatcagagt    8700
```

```
gtgatgctgg tgtttatcga aggcagggcc gacgccgatc accacttcat cggcgcgttc   8760
atcggcagaa gctacccgc cctcgcgggt tttcagggta aaagagggct gaatttgggt   8820
tgtctgttgc acaggaatac cgccttgttc aatggtgtcg ggctgaacca cgcccggaat   8880 attttgatc tccgcccagc gttcggcaga gatgcgatag ccggtgcccg gcccctgata   8940
gtcattgatg tcgttgaccg cactcaccac ctcgaactgc cgatcgaaaa tggccgaggt   9000
ctgcaggtaa tcgccggtga cccgctggcg cagcatattg agaatattgc tggcgatatc   9060
ctcaaagccg ctgcggctca gcgcgccgac aatatcgagg ccggtgatgt tgcgcttcat   9120
catctcttcc accgcactca gatcctccac cacgttacgc ggcggcatct cgttgctgcc   9180
gtgcgcgtag gtggcggcct ccacctcctc gtcggcgatt ggcggcagcc ccagctcgcg   9240
gaaaaccgcc tggatcgccc gcgccgcttt ctggcgaatg caatggtttt ccgcctcggt   9300
caccggacgc aggccgccgt caaccatcag gtcacgctgc aggatgttgt aatcatcaaa   9360
atcttccgca tcgaagttcg agccggcgaa catgttgtcg tagttcggca ccgcgctgta   9420 gccgagaaa ataaagtcgg tgcccggcag catctgcatc agggtgcgcg cggtgcggcg   9480
aatatccgag tgggagaaag tctggtcgtt ggcggacgcc acttcgaggt cgagcataga   9540
ggcgatcagg ttttccgcca gcaccgcccg aatgcccgac ggcacagcgc cggtcatgcc   9600
gatacagctc accgcgccgt tttgcagtcc ctgaaccccg cgccctttag taatgaagat   9660
gcagcgcgat tcgaggtaga gcatcgactt gctctccgaa tagcccatca gcgcttcgga   9720
tccggtgccg gaggtgtagc gcattttcaa cccgcgggag gcgtaggccg aggcgaggaa   9780
cgcctttgac cacggcgtat catcgccgtc ggtaaatacc gcttcggtgc cgtagaccga   9840
caccgtctcg gcgtagctgg ttaagccacg catgcccagc tccagctcgg tggcctcttc   9900
caccgagcac tgcgtcaaca cgccggggcg gccgcactgc gaaccgacca acagcgccag   9960
ggcgttaaac ggcgcgtagc gcgcgatacc gaccgtggtc tcctgttctg agaagccgcg  10020
gatcccggcc tcggcggcgt cagcggcaat ctgcaccgga ttatctttga gattggtgac  10080
gtggcactgg ttggagggg tccggcgggc acgcatcttc tgcagcgcca tcatcatctc  10140
caccacgttc atctgcgcca tcacctcgac cgctttggcc ggcgtgatgg cggtagtgat  10200
ggcaatgatc tcctcccggc tgacgtgaat atccaccagc atacgggcta tttccaccgc  10260
ctccaggcgc attgcctgct ctgtgcgctc aacgttgatc gcgtaatcgg cgataaatcg  10320
gtcgatcatg tcaaactggt cccggcgttt gccgtccagt tcgacgatca gaccgttgtc  10380
cacttttact gaagagaccg ggtcaaaggg gctgtccatg gcgatcagcc cctcttcagg  10440
ccactcgcca atcagcccgt cctgattgac ggggcgctgg gccagtactg caaatcgttt  10500
tgatcttttc attgttcatc ggctcaaaag gtgaagcttg gttacctccg ggaaacgcgg  10560
ttgatttgtt tagtggttga attatttgct caggatgtgg cattgtcaag ggcgtgacgg  10620
ctcgcctgac ttctcgttcc agtgcccccg tccgacagtc gagcgtgcga gcccataatc  10680
tcgcgctggt gctgcatacc gtggcaaaca gcacagatcg cctaggaaaa aaaaagcccg  10740
cactgtcagg tgcgggcttt tttctgtgtt tgctaggcca gttcaagcgc aagcatcagg  10800
gtgcagctgg gcagaggcga gattcctccc cgggatcacg aactgtttta acgggccgct  10860
ctcggccata ttgcggtcga taagccgctc cagggcggta atctcctctt cgccgatcgt  10920
ctggctcagg cgggtcaggc cccgcgcatc gctggccagt tcagccccca gcacgaacag  10980
cgtctgctga atatggtgca ggcttttccg cagcccggcg tcgcgggtcg tggcgtagca  11040
gacgcccagc tgggatatca gttcatcgac ggtgccgtag gcctcgacgc gaatatggtc  11100
```

```
tttctcgatg cggctgccgc cgtacagggc ggtggtgcct ttatccccgg tgcgggtata    11160
gatacgatac attcagtttc tctcacttaa cggcaggact ttaaccagct gcccggcgtt    11220
ggcgccgagc gtacgcagtt gatcgtcgct atcggtgacg tgtccggtag ccagcggcgc    11280
gtccgccggc agctgggcat gagtgagggc tatctcgccg gacgcgctga gcccgatacc    11340
cacccgcagg ggcgagcttc tggccgccag ggcgcccagc gcagcggcgt caccgcctcc    11400
gtcataggtt atggtctggc aggggacccc ctgctcctcc agcccccagc acagctcatt    11460
gatggcgccg gcatggtgcc cgcgcggatc gtaaaacagg cgtacgcctg gcggtgaaag    11520
cgacatgacg gtcccctcgt taacactcag aatgcctggc ggaacatacg atagctcata    11580
atataccttc tcgcttcagg ttataatgcg gaaaaacaat ccaggcgcca ctgggctaat    11640
aattgatcct gctcgaccgt accgccgcta acgccgacgg cgccaattac ctgctcatta    11700
aaaataactg gcaggccgcc gccaaaaata taattcgct gttggttggt tagctgcaga    11760
ccgtacagag attgtcctgg ctggaccgct gacgtaattt catgggtacc ttgcttcagg    11820
ctgcaggcgc tccaggcttt attcagggaa atatcgcagc tggagacgaa ggcctcgtcc    11880
atccgctgga taagcagcgt gttgcctccg cggtcaacta cggaaaacac caccgccacg    11940
ttgatctcag tggcttttttt ttccaccgcc gccgccattt gctgggcggc ggccagggtg    12000
attgtctgaa cttgttggct cttgttcatc attctctccc gcaagcttgg ttacctccgg    12060
gaaacgcggt tgatttgttt agtggttgaa ttatttgctc aggatgtggc attgtcaagg    12120
gcgtgacgga tcgcctgact tctcgttcca gtgcccccgt ccgacagtcg agcgtgcgag    12180
cccataatct cgcgctggtg ctgcataccg tggcaaacag cacagatcgc ctagcagtca    12240
aaagcctccg gtcggaggct tttgactatt taaatgaatt cccgacagta agacgggtaa    12300
gcctgttgat gataccgctg ccttactggg tgcattagcc agtctgaatg acctgtcacg    12360
ggataatccg aagtggtcag actggaaaat cagagggcag gaactgctga acagcaaaaa    12420
gtcagatagc accacatagc agacccgcca taaaacgccc tgagaagccc gtgacgggct    12480
tttcttgtat tatgggtagt ttccttgcat gaatccataa aaggcgcctg tagtgccatt    12540
taccccattt cactgccaga gccgtgagcg cagcgaactg aatgtcacga aaaagacagc    12600
gactcaggtg cctgatggtc ggagacaaaa ggaatattca gcgatttgcc cgagcttgcg    12660
agggtgctac ttaagccttt agggttttaa ggtctgtttt gtagaggagc aaacagcgtt    12720
tgcgacatcc ttttgtaata ctgcggaact gactaaagta gtgagttata cacagggctg    12780
ggatctattc tttttatctt tttttattct ttctttattc tataaattat aaccacttga    12840
atataaacaa aaaaaacaca caaaggtcta gcggaattta cagagggtct agcagaattt    12900
acaagttttc cagcaaaggt ctagcagaat ttacagatac ccacaactca aggaaaagg    12960 actagtaatt atcattgact agcccatctc aattggtata gtgattaaaa tcacctagac    13020
caattgagat gtatgtctga attagttgtt ttcaaagcaa atgaactagc gattagtcgc    13080
tatgacttaa cggagcatga accaagcta atttatgct gtgtggcact actcaaccc    13140 acgattgaaa accctacaag gaaagaacgg acggtatcgt tcacttataa ccaatacgct    13200
cagatgatga acatcagtag ggaaaatgct tatggtgtat tagctaaagc aaccagagag    13260
ctgatgacga gaactgtgga aatcaggaat cctttggtta aaggctttga gattttccag    13320 tggacaaaact atgccaagtt ctcaagcgaa aaattagaat tagttttag tgaagagata    13380 ttgccttatc ttttccagtt aaaaaaattc ataaatata atctggaaca tgttaagtct    13440
tttgaaaaca aatactctat gaggatttat gagtggttat taaaagaact aacacaaaag    13500
```

-continued

```
aaaactcaca aggcaaatat agagattagc cttgatgaat ttaagttcat gttaatgctt    13560
gaaaataact accatgagtt taaaaggctt aaccaatggg ttttgaaacc aataagtaaa    13620
gatttaaaca cttacagcaa tatgaaattg gtggttgata agcgaggccg cccgactgat    13680
acgttgattt tccaagttga actagataga caaatggatc tcgtaaccga acttgagaac    13740
aaccagataa aaatgaatgg tgacaaaata ccaacaacca ttacatcaga ttcctaccta    13800
cataacggac taagaaaaac actacacgat gctttaactg caaaaattca gctcaccagt    13860
tttgaggcaa aattttttgag tgacatgcaa agtaagtatg atctcaatgg ttcgttctca    13920
tggctcacgc aaaaacaacg aaccacacta gagaacatac tggctaaata cggaaggatc    13980
tgaggttctt atggctcttg tatctatcag tgaagcatca agactaacaa acaaaagtag    14040
aacaactgtt caccgttaca tatcaaaggg aaaactgtcc atatgcacag atgaaaacgg    14100
tgtaaaaaag atagatacat cagagctttt acgagttttt ggtgcattca aagctgttca    14160
ccatgaacag atcgacaatg taacagatga acagcatgta acacctaata gaacaggtga    14220
aaccagtaaa acaaagcaac tagaacatga aattgaacac ctgagacaac ttgttacagc    14280
tcaacagtca cacatagaca gcctgaaaca ggcgatgctg cttatcgaat caaagctgcc    14340
gacaacacgg gagccagtga cgcctcccgt ggggaaaaaa tcatggcaat tctggaagaa    14400
atagcgcttt cagccggcaa accggctgaa gccggatctg cga                     14443
```

<210> SEQ ID NO 85
<211> LENGTH: 60
<212> TYPE: DNA
<213> ORGANISM: Artificial Sequence
<220> FEATURE:
<223> OTHER INFORMATION: Primer

<400> SEQUENCE: 85

```
tagacgtgaa acaggagtca taatgaattt tcatcatctg ggatcccttg cccgctgttg    60
```

<210> SEQ ID NO 86
<211> LENGTH: 60
<212> TYPE: DNA
<213> ORGANISM: Artificial Sequence
<220> FEATURE:
<223> OTHER INFORMATION: Primer

<400> SEQUENCE: 86

```
catttcaggc ctccaggctt atccagatgg ttttcagttc gaattcgcag gaccgtgata    60
```

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87

```
tgagcgaatc ccgatgagct tact                                           24
```

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88

```
atacgttcgc ggatgatctc acca                                           24
```

<210> SEQ ID NO 89
<211> LENGTH: 60
<212> TYPE: DNA
<213> ORGANISM: Artificial Sequence
<220> FEATURE:
<223> OTHER INFORMATION: Primer

<400> SEQUENCE: 89
accattgtgg cgatgggttg cttctacagc ctgaacgaga ggatcccttg cccgctgttg    60

<210> SEQ ID NO 90
<211> LENGTH: 60
<212> TYPE: DNA
<213> ORGANISM: Artificial Sequence
<220> FEATURE:
<223> OTHER INFORMATION: Primer

<400> SEQUENCE: 90
ttacgggctt ctatctcttc cacaatgcgg acatacatct gaattcgcag gaccgtgata    60

<210> SEQ ID NO 91
<211> LENGTH: 60
<212> TYPE: DNA
<213> ORGANISM: Artificial Sequence
<220> FEATURE:
<223> OTHER INFORMATION: Primer

<400> SEQUENCE: 91
attaggtaca ctttattcgg tcaaccagtt taccagcatt cgtcttgagc gattgtgtag    60

<210> SEQ ID NO 92
<211> LENGTH: 60
<212> TYPE: DNA
<213> ORGANISM: Artificial Sequence
<220> FEATURE:
<223> OTHER INFORMATION: Primer

<400> SEQUENCE: 92
tcggcgttga agcagcaca atcccaagcg aactggcaat tgaatatcct ccttagttcc    60

<210> SEQ ID NO 93
<211> LENGTH: 21
<212> TYPE: DNA
<213> ORGANISM: Artificial Sequence
<220> FEATURE:
<223> OTHER INFORMATION: Primer

<400> SEQUENCE: 93
atggcactga atattccatt c                                              21

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ctatattgct gaaggtacag                                                20

<210> SEQ ID NO 95
<211> LENGTH: 60
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: n is g or t

<400> SEQUENCE: 95
attaggtaca ctttattcgg tcaaccagtt taccagcatt nnntttatga tgttctacgg    60

<210> SEQ ID NO 96
<211> LENGTH: 60
<212> TYPE: DNA
<213> ORGANISM: Artificial Sequence
<220> FEATURE:
<223> OTHER INFORMATION: Primer

<400> SEQUENCE: 96
tcggcgttga aagcagcaca atcccaagcg aactggcaat ttgaaaacca atcagaaaga    60

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
atctagggtt gacagggacg gaat                                           24

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
aagctatcaa gcaaaccgca tccc                                           24

<210> SEQ ID NO 99
<211> LENGTH: 100
<212> TYPE: DNA
<213> ORGANISM: Artificial Sequence
<220> FEATURE:
<223> OTHER INFORMATION: Primer

<400> SEQUENCE: 99
cgtctaccct tgttatacct cacaccgcaa ggagacgatc atgaccaata atccccttc     60 agcacagatt aagcccggcg gtgtaggctg gagctgcttc                         100

<210> SEQ ID NO 100
<211> LENGTH: 100
<212> TYPE: DNA
<213> ORGANISM: Artificial Sequence
<220> FEATURE:
<223> OTHER INFORMATION: Primer

<400> SEQUENCE: 100
gcatcaggca atgaataccc aatgcgacca gcttcttata tcagaacagc cccaacggtt    60
tatccgagta gctcaccagc catatgaata tcctccttag                         100

<210> SEQ ID NO 101
<211> LENGTH: 22
```

```
<212> TYPE: DNA
<213> ORGANISM: Artificial Sequence
<220> FEATURE:
<223> OTHER INFORMATION: Primer

<400> SEQUENCE: 101
atgaccaata atcccccttc ag                                              22

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
gcttcttata tcagaacagc c                                               21

<210> SEQ ID NO 103
<211> LENGTH: 9317
<212> TYPE: DNA
<213> ORGANISM: Artificial Sequence
<220> FEATURE:
<223> OTHER INFORMATION: Plasmid

<400> SEQUENCE: 103
tcgaggaatt cgcaggaccg tgatacacgg gacaggtcac tgaatgacga caatgtcctg      60
gaaatcagcg aaccgcgcat ctgaagtaca tttgagcgac tgtaccagaa catgaatgag     120
gcgtttggat taggcgatta ttagcagggc taagcatttt actattatta ttttccggtt     180
gagggatata gagctatcga caacaaccgg aaaaagttta cgtctatatt gctgaaggta     240
caggcgtttc cataactatt tgctcgcgtt ttttactcaa gaagaaaatg ccaaatagca     300
acatcaggca gacaataccc gaaattgcga agaaaactgt ctggtagcct gcgtggtcaa     360
agagtatccc agtcggcgtt gaaagcagca caatcccaag cgaactggca atttgaaaac     420
caatcagaaa gatcgtcgac gacaggcgct tatcaaagtt tgccacgctg tatttgaaga     480
cggatatgac acaaagtgga acctcaatgg catgtaacaa cttcactaat gaataatcc      540 aggggttaac gaacagcgcg caggaaagga tacgcaacgc cataatcaca actccgataa     600
gtaatgcatt ttttggccct acccgattca caaagaaagg aataatcgcc atgcacagcg     660
cttcgagtac cacctggaat gagttgagat aaccatacag gcgcgttcct acatcgtgtg     720
attcgaataa acctgaataa aagacaggaa aaagttgttg atcaaaaatg ttatagaaag     780
accacgtccc cacaataaat atgacgaaaa cccagaagtt tcgatccttg aaaactgcga     840
taaaatcctc ttttttttacc cctcccgcat ctgccgctac gcactggtga tccttatctt     900
taaaacgcat gttgatcatc ataaatacag cgccaaatag cgagaccaac cagaagttga     960
tatggggact gatactaaaa aatatgccgg caaagaacgc gccaatagca tagccaaaag    1020
atccccaggc gcgcgctgtt ccatattcga atgaaaatt tcgcgccatt ttttcggtga     1080
agctatcaag caaaccgcat cccgccagat accccaagcc aaaaaatagc gcccccagaa    1140
ttagacctac agaaaaattg ctttgcagta acggttcata acgtaaatc ataacggtc      1200 cggtcaagac caggatgaaa ctcatacacc agatgagcgg tttcttcaga ccgagtttat    1260
cctgaacgat gccgtagaac atcataaata gaatgctggt aaactggttg accgaataaa    1320
gtgtacctaa ttccgtccct gtcaacccta gatgtccttt cagccaaata gcgtataacg    1380
accaccacag cgaccaggaa ataaaaaaga gaaatgagta actggatgca aaacgatagt    1440
acgcatttct gaatggaata ttcagtgcca taattacctg cctgtcgtta aaaaattcac    1500
```

```
gtcctatttta gagataagag cgacttcgcc gtttacttct cactattcca gttcttgtcg   1560
acatggcagc gctgtcattg ccccttcgc cgttactgca agcgctccgc aacgttgagc    1620
gagatcgata attcgtcgca tttctctctc atctgtagat aatcccgtag aggacagacc   1680
tgtgagtaac ccggcaacga acgcatctcc cgcccccgtg ctatcgacac aattcacaga   1740
cattccagca aaatggtgaa cttgtcctcg ataacagacc accacccctt ctgcaccttt   1800
agtcaccaac agcatggcga tctcatactc ttttgccagg gcgcatatat cctgatcgtt   1860
ctgtgttttt ccactgataa gtcgccattc ttcttccgag agcttgacga catccgccag   1920
ttgtagcgcc tgccgcaaac acaagcggag caaatgctcg tcttgccata gatcttcacg   1980
aatattagga tcgaagctga caaaacctcc ggcatgccgg atcgccgtca tcgcagtaaa   2040
tgcgctggta cgcgaaggct cggcagacaa cgcaattgaa cagagatgta accattcgcc   2100
atgtcgccag cagggcaagt ctgtcgtctc taaaaaaga tcggcactgg ggcggaccat    2160
aaacgtaaat gaacgttccc cttgatcgtt cagatcgaca agcaccgtgg atgtccggtg   2220
ccattcatct tgcttcagat acgtgatatc gactccctca gttagcagcg ttctttgcat   2280
taacgcacca aaaggatcat cccccacccg acctataaac ccacttgttc cgcctaatct   2340
ggcgattccc accgcaacgt tagctggcgc gccgccagga caaggcagta ggcgcccgtc   2400
tgattctggc aagagatcta cgaccgcatc ccctaaaacc catactttgg ctgacatttt   2460
tttcccttaa attcatctga gttacgcata gtgataaacc tcttttcgc aaaatcgtca    2520 tggatttact aaaacatgca tattcgatca caaaacgtca tagttaacgt taacatttgt    2580
gatattcatc gcatttatga aagtaaggga ctttattttt ataaaagtta acgttaacaa   2640
ttcaccaaat ttgcttaacc aggatgatta aaatgacgca atctcgattg catgcggcgc   2700
aaaacgccct agcaaaactt catgagcacc ggggtaacac tttctatccc cattttcacc   2760
tcgcgcctcc tgccgggtgg atgaacgatc caaacggcct gatctggttt aacgatcgtt   2820
atcacgcgtt ttatcaacat catccgatga gcgaacactg ggggccaatg cactggggac   2880
atgccaccag cgacgatatg atccactggc agcatgagcc tattgcgcta gcgccaggag   2940
acgataatga caaagacggg tgttttttcag gtagtgctgt cgatgacaat ggtgtcctct   3000
cacttatcta caccggacac gtctggctcg atggtgcagg taatgacgat gcaattcgcg   3060
aagtacaatg tctggctacc agtcgggatg gtattcattt cgagaaacag ggtgtgatcc   3120
tcactccacc agaaggaatc atgcacttcc gcgatcctaa agtgtggcgt gaagccgaca   3180
catggtggat ggtagtcggg gcgaaagatc caggcaacac ggggcagatc ctgctttatc   3240
gcggcagttc gttgcgtgaa tggaccttcg atcgcgtact ggcccacgct gatgcgggtg   3300
aaagctatat gtgggaatgt ccggactttt tcagccttgg cgatcagcat tatctgatgt   3360
tttccccgca gggaatgaat gccgagggat acagttaccg aaatcgcttt caaagtggcg   3420
taatacccgg aatgtggtcg ccaggacgac tttttgcaca atccgggcat tttactgaac   3480
ttgataacgg gcatgacttt tatgcaccac aaagcttttt agcgaaggat ggtcggcgta   3540
ttgttatcgg ctggatggat atgtgggaat cgccaatgcc ctcaaaacgt gaaggatggg   3600
caggctgcat gacgctggcg cgcgagctat cagagagcaa tggcaaactt ctacaacgcc   3660
cggtacacga agctgagtcg ttacgccagc agcatcaatc tgtctctccc cgcacaatca   3720
gcaataaata tgttttgcag gaaaacgcgc aagcagttga gattcagttg cagtgggcgc   3780
tgaagaacag tgatgccgaa cattacggat tacagctcgg cactggaatg cggctgtata   3840
ttgataacca atctgagcga cttgttttgt ggcggtatta cccacacgag aatttagacg   3900
```

```
gctaccgtag tattcccctc ccgcagcgtg acacgctcgc cctaaggata tttatcgata    3960
catcatccgt ggaagtattt attaacgacg gggaagcggt gatgagtagt cgaatctatc    4020
cgcagccaga agaacgggaa ctgtcgcttt atgcctccca cggagtggct gtgctgcaac    4080
atggagcact ctggctactg ggttaacata atatcaggtg gaacaacgga tcaacagcgg    4140
gcaagggatc cacgaagctt cccatggtga cgtcaccggt aaaccagcaa tagacataag    4200
cggctattta acgaccctgc cctgaaccga cgaccgggtc gaatttgctt tcgaatttct    4260
gccattcatc cgcttattat acttattcag gcgtagcacc aggcgtttaa gggcaccaat    4320
aactgcctta aaaaaattac gccccgccct gccactcatc gcagtactgt tgtaattcat    4380
taagcattct gccgacatgg aagccatcac agacggcatg atgaacctga atcgccagcg    4440
gcatcagcac cttgtcgcct tgcgtataat atttgcccat ggtgaaaacg ggggcgaaga    4500
agttgtccat attggccacg tttaaatcaa aactggtgaa actcacccag ggattggctg    4560
agacgaaaaa catattctca ataaacccct tagggaaata ggccaggttt tcaccgtaac    4620
acgccacatc ttgcgaatat atgtgtagaa actgccggaa atcgtcgtgg tattcactcc    4680
agagcgatga aaacgtttca gtttgctcat ggaaaacggt gtaacaaggg tgaacactat    4740
cccatatcac cagctcaccg tctttcattg ccatacggaa ttccggatga gcattcatca    4800
ggcgggcaag aatgtgaata aaggccggat aaaacttgtg cttattttc tttacggtct    4860 ttaaaaaggc cgtaatatcc agctgaacgg tctggttata ggtacattga caactgact    4920 gaaatgcctc aaaatgttct ttacgatgcc attgggatat atcaacgtg gtatatccag    4980 tgattttttt ctccatttta gcttccttag ctcctgaaaa tctcgataac tcaaaaaata    5040
cgcccggtag tgatcttatt tcattatggt gaaagttgga acctcttacg tgccgatcaa    5100
cgtctcattt tcgccaaaag ttggcccagg gcttcccggt atcaacaggg acaccaggat    5160
ttatttattc tgcgaagtga tcttccgtca caggtattta ttcggcgcaa agggcctcgt    5220
gatacgccta tttttatagg ttaatgtcat gataataatg gtttcttaga cgtcaggtgg    5280
cacttttcgg ggaaatgtgc gcgcccgcgt tcctgctggc gctgggcctg tttctggcgc    5340
tggacttccc gctgttccgt cagcagcttt tcgcccacgg ccttgatgat cgcggcggcc    5400
ttggcctgca tatcccgatt caacggcccc agggcgtcca gaacgggctt caggcgctcc    5460
cgaaggtctc gggccgtctc ttgggcttga tcggccttct tgcgcatctc acgcgctcct    5520
gcggcggcct gtagggcagg ctcataccc tgccgaaccg cttttgtcag ccggtcggcc    5580
acggcttccg gcgtctcaac gcgctttgag attcccagct tttcggccaa tccctgcggt    5640
gcataggcgc gtggctcgac cgcttgcggg ctgatggtga cgtggcccac tggtggccgc    5700
tccagggcct cgtagaacgc ctgaatgcgc gtgtgacgtg ccttgctgcc ctcgatgccc    5760
cgttgcagcc ctagatcggc cacagcggcc gcaaacgtgg tctggtcgcg ggtcatctgc    5820
gctttgttgc cgatgaactc cttggccgac agcctgccgt cctgcgtcag cggcaccacg    5880
aacgcggtca tgtgcgggct ggtttcgtca cggtggatgc tggccgtcac gatgcgatcc    5940
gccccgtact tgtccgccag ccacttgtgc gccttctcga agaacgccgc ctgctgttct    6000
tggctggccg acttccacca ttccgggctg gccgtcatga cgtactcgac cgccaacaca    6060
gcgtccttgc gccgcttctc tggcagcaac tcgcgcagtc ggcccatcgc ttcatcggtg    6120
ctgctggccg cccagtgctc gttctctggc gtcctgctgg cgtcagcgtt gggcgtctcg    6180
cgctcgcggt aggcgtgctt gagactggcc gccacgttgc ccattttcgc cagcttcttg    6240
catcgcatga tcgcgtatgc cgccatgcct gcccctccct tttggtgtcc aaccggctcg    6300
```

```
acgggggcag cgcaaggcgg tgcctccggc gggccactca atgcttgagt atactcacta    6360
gactttgctt cgcaaagtcg tgaccgccta cggcggctgc ggcgccctac gggcttgctc    6420
tccgggcttc gccctgcgcg gtcgctgcgc tcccttgcca gcccgtggat atgtggacga    6480
tggccgcgag cggccaccgg ctggctcgct tcgctcggcc cgtggacaac cctgctggac    6540
aagctgatgg acaggctgcg cctgcccacg agcttgacca cagggattgc ccaccggcta    6600
cccagccttc gaccacatac ccaccggctc caactgcgcg gcctgcggcc ttgccccatc    6660
aattttttta atttctctg gggaaaagcc tccggcctgc ggcctgcgcg cttcgcttgc     6720
cggttggaca ccaagtggaa ggcgggtcaa ggctcgcgca gcgaccgcgc agcggcttgg    6780
ccttgacgcg cctggaacga cccaagccta tgcgagtggg ggcagtcgaa ggcgaagccc    6840
gcccgcctgc cccccgagac ctgcaggggg ggggggcgc tgaggtctgc ctcgtgaaga     6900
aggtgttgct gactcatacc aggcctgaat cgccccatca tccagccaga aagtgaggga    6960
gccacggttg atgagagctt tgttgtaggt ggaccagttg gtgattttga acttttgctt    7020
tgccacggaa cggtctgcgt tgtcgggaag atgcgtgatc tgatccttca actcagcaaa    7080
agttcgattt attcaacaaa gccgccgtcc cgtcaagtca gcgtaatgct ctgccagtgt    7140
tacaaccaat taaccaattc tgattagaaa aactcatcga gcatcaaatg aaactgcaat    7200
ttattcatat caggattatc aataccatat ttttgaaaaa gccgtttctg taatgaagga    7260
gaaaactcac cgaggcagtt ccataggatg gcaagatcct ggtatcggtc tgcgattccg    7320
actcgtccaa catcaataca acctattaat ttcccctcgt caaaataag gttatcaagt      7380
gagaaatcac catgagtgac gactgaatcc ggtgagaatg gcaaaagctt atgcatttct    7440
ttccagactt gttcaacagg ccagccatta cgctcgtcat caaaatcact cgcatcaacc    7500
aaaccgttat tcattcgtga ttgcgcctga gcagacgaa atacgcgatc gctgttaaaa      7560
ggacaattac aaacaggaat cgaatgcaac cggcgcagga acactgccag cgcatcaaca    7620
atattttcac ctgaatcagg atattcttct aatacctgga atgctgtttt cccggggatc    7680
gcagtggtga gtaaccatgc atcatcagga gtacggataa aatgcttgat ggtcggaaga    7740
ggcataaatt ccgtcagcca gtttagtctg accatctcat ctgtaacatc attggcaacg    7800
ctacctttgc catgtttcag aaacaactct ggcgcatcgg gcttcccata caatcgatag    7860
attgtcgcac ctgattgccc gacattatcg cgagcccatt tacccata taaatcagca       7920
tccatgttgg aatttaatcg cggcctcgag caagacgttt cccgttgaat atggctcata    7980
acacccctg tattactgtt tatgtaagca gacagttta ttgttcatga tgatatattt        8040
ttatcttgtg caatgtaaca tcagagattt tgagacacaa cgtggctttc cccccccccc    8100
ctgcaggtcc cgagcctcac ggcggcgagt gcggggttc caaggggca gcgccacctt      8160
gggcaaggcc gaaggccgcg cagtcgatca acaagcccg gaggggccac ttttgccgg       8220
aggggggagcc gcgccgaagg cgtgggggaa ccccgcaggg gtgcccttct ttgggcacca   8280
aagaactaga tatagggcga aatgcgaaag acttaaaaat caacaactta aaaaggggg     8340
gtacgcaaca gctcattgcg gcacccccg caatagctca ttgcgtaggt taaagaaaat      8400
ctgtaattga ctgccacttt tacgcaacgc ataattgttg tcgcgctgcc gaaaagttgc    8460
agctgattgc catggtgcc gcaaccgtgc ggcaccctac cgcatggaga taagcatggc      8520
cacgcagtcc agagaaatcg gcattcaagc caagaacaag cccggtcact gggtgcaaac    8580
ggaacgcaaa gcgcatgagg cgtgggccgg gcttattgcg aggaaaccca cggcggcaat    8640
gctgctgcat cacctcgtgg cgcagatggg ccaccagaac gccgtggtgg tcagccagaa    8700
```

```
gacactttcc aagctcatcg gacgttcttt gcggacggtc caatacgcag tcaaggactt    8760
ggtggccgag cgctggatct ccgtcgtgaa gctcaacggc cccggcaccg tgtcggccta    8820
cgtggtcaat gaccgcgtgg cgtggggcca gccccgcgac cagttgcgcc tgtcggtgtt    8880
cagtgccgcc gtggtggttg atcacgacga ccaggacgaa tcgctgttgg ggcatggcga    8940
cctgcgccgc atcccgaccc tgtatccggg cgagcagcaa ctaccgaccg gcccggcga    9000 ggagccgccc agccagcccg gcattccggg catggaacca gacctgccag ccttgaccga    9060
aacggaggaa tgggaacggc gcgggcagca gcgcctgccg atgcccgatg agccgtgttt    9120
tctggacgat ggcgagccgt tggagccgcc gacacgggtc acgctgccgc gccggtagca    9180
cttgggttgc gcagcaaccc gtaagtgcgc tgttccagac tatcggctgt agccgcctcg    9240
ccgccctata ccttgtctgc ctccccgcgt tgcgtcgcgg tgcatggagc cgggccacct    9300
cgacctgaat ggaagcc                                                   9317
```

<210> SEQ ID NO 104
<211> LENGTH: 415
<212> TYPE: PRT
<213> ORGANISM: Artificial Sequence
<220> FEATURE:
<223> OTHER INFORMATION: variant CscB sequence with L61A substitution

<400> SEQUENCE: 104

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Ala Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255
```

```
Arg Leu Tyr Gly Tyr Leu Asn Ser Phe Gln Val Val Leu Glu Ala Leu
            260                 265                 270

Cys Met Ala Ile Ile Pro Phe Val Asn Arg Val Gly Pro Arg Asn
        275                 280                 285

Ala Leu Leu Ile Gly Val Val Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 105
<211> LENGTH: 415
<212> TYPE: PRT
<213> ORGANISM: Artificial Sequnce
<220> FEATURE:
<223> OTHER INFORMATION: CscB variant with L61D substitution

<400> SEQUENCE: 105

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
                20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Asp Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205
```

```
Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
            245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
            275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 106
<211> LENGTH: 415
<212> TYPE: PRT
<213> ORGANISM: Artificial Sequence
<220> FEATURE:
<223> OTHER INFORMATION: CscB variant with L61E substitution

<400> SEQUENCE: 106

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Glu Phe Met Met
50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
            85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
            130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
```

```
                      165                 170                 175
Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 107
<211> LENGTH: 415
<212> TYPE: PRT
<213> ORGANISM: Artificial Sequence
<220> FEATURE:
<223> OTHER INFORMATION: CscB variant with L61G substitution

<400> SEQUENCE: 107

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val

```
Asp Ser Phe Thr Glu Lys Met Ala Arg Asn Phe His Phe Glu Tyr Gly
        130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 108
<211> LENGTH: 415
<212> TYPE: PRT
<213> ORGANISM: Artificial Sequence
<220> FEATURE:
<223> OTHER INFORMATION: CscB variant with L61I substitution

<400> SEQUENCE: 108

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Ile Phe Met Met
    50                  55                  60

Phe Tyr Gly Ile Val Gln Asp Lys Leu Gly Leu Lys Lys Pro Leu Ile
65                  70                  75                  80
```

Trp Cys Met Ser Phe Ile Leu Val Leu Thr Gly Pro Phe Met Ile Tyr
            85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
            130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
                180                 185                 190

Lys Asp His Gln Cys Val Ala Ala Asp Ala Gly Gly Val Lys Lys Glu
                195                 200                 205

Asp Phe Ile Ala Val Phe Lys Asp Arg Asn Phe Trp Val Phe Val Ile
                210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
                260                 265                 270

Cys Met Ala Ile Ile Pro Phe Val Asn Arg Val Gly Pro Lys Asn
                275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
                370                 375                 380

Gly Ile Val Cys Leu Met Leu Leu Phe Gly Ile Phe Leu Ser Lys
385                 390                 395                 400

Lys Arg Glu Gln Ile Val Met Glu Thr Pro Val Pro Ser Ala Ile
                405                 410                 415

<210> SEQ ID NO 109
<211> LENGTH: 415
<212> TYPE: PRT
<213> ORGANISM: Artificial Sequence
<220> FEATURE:
<223> OTHER INFORMATION: CscB variant with L61K substitution

<400> SEQUENCE: 109

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
                20                  25                  30

Tyr Ala Ile Trp Leu Lys Gly His Leu Gly Leu Thr Gly Thr Glu Leu

```
                35                  40                  45
Gly Thr Leu Tyr Ser Val Asn Gln Phe Thr Ser Ile Lys Phe Met Met
 50                  55                  60

Phe Tyr Gly Ile Val Gln Asp Lys Leu Gly Leu Lys Lys Pro Leu Ile
 65                  70                  75                  80

Trp Cys Met Ser Phe Ile Leu Val Leu Thr Gly Pro Phe Met Ile Tyr
                 85                  90                  95

Val Tyr Glu Pro Leu Leu Gln Ser Asn Phe Ser Val Gly Leu Ile Leu
                100                 105                 110

Gly Ala Leu Phe Phe Gly Leu Gly Tyr Leu Ala Gly Cys Gly Leu Leu
                115                 120                 125

Asp Ser Phe Thr Glu Lys Met Ala Arg Asn Phe His Phe Glu Tyr Gly
130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
                180                 185                 190

Lys Asp His Gln Cys Val Ala Ala Asp Ala Gly Gly Val Lys Lys Glu
                195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
                260                 265                 270

Cys Met Ala Ile Ile Pro Phe Phe Val Asn Arg Val Gly Pro Lys Asn
                275                 280                 285

Ala Leu Leu Ile Gly Val Val Ile Met Ala Leu Arg Ile Leu Ser Cys
                290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 110
<211> LENGTH: 415
<212> TYPE: PRT
<213> ORGANISM: Artificial Sequence
<220> FEATURE:
<223> OTHER INFORMATION: CscB variant with L61Q substitution

<400> SEQUENCE: 110
```

-continued

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Gln Phe Met Met
    50                  55                      60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415
```

```
<210> SEQ ID NO 111
<211> LENGTH: 415
<212> TYPE: PRT
<213> ORGANISM: Artificial Sequence
<220> FEATURE:
<223> OTHER INFORMATION: CscB variant with L61S substitution

<400> SEQUENCE: 111

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Ser Phe Met Met
50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380
```

```
Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415
```

<210> SEQ ID NO 112
<211> LENGTH: 415
<212> TYPE: PRT
<213> ORGANISM: Artificial Sequence
<220> FEATURE:
<223> OTHER INFORMATION: CscB vaiant with L61T substitution

<400> SEQUENCE: 112

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Thr Phe Met Met
50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335
```

```
Ala Asn Phe Asp Lys Arg Leu Ser Ser Thr Ile Phe Leu Ile Gly Phe
                340                 345                 350

-continued

```
            290                 295                 300
Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
            370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415
```